US007018799B2

(12) United States Patent
McCarthy et al.

(10) Patent No.: US 7,018,799 B2
(45) Date of Patent: *Mar. 28, 2006

(54) METHODS FOR IDENTIFYING INHIBITORS OF NEURONAL DEGENERATION

(75) Inventors: Justin McCarthy, Mountain View, CA (US); Barbara Cordell, Palo Alto, CA (US)

(73) Assignee: Scios, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/417,422

(22) Filed: Apr. 14, 2003

(65) Prior Publication Data

US 2003/0219720 A1 Nov. 27, 2003

Related U.S. Application Data

(63) Continuation of application No. 09/754,949, filed on Jan. 4, 2001.

(60) Provisional application No. 60/175,200, filed on Jan. 10, 2000.

(51) Int. Cl.
*C12Q 1/68* (2006.01)
*G01N 33/53* (2006.01)
*C12N 15/63* (2006.01)
*C12N 15/85* (2006.01)

(52) U.S. Cl. ............................ 435/6; 435/7.1; 435/7.2; 435/7.21; 435/455

(58) Field of Classification Search .................... 435/4, 435/7.2, 7.21, 244, 6, 455; 514/1; 424/93.2, 424/93.21
See application file for complete search history.

(56) References Cited

U.S. PATENT DOCUMENTS

| 4,816,567 A | 3/1989 | Cabilly et al. |
| 5,908,750 A | 6/1999 | Reed et al. |
| 6,111,075 A * | 8/2000 | Xu et al. ..................... 530/350 |

FOREIGN PATENT DOCUMENTS

EP WO 98/13494 2/1998

OTHER PUBLICATIONS

Annaert et al., "Presenilins: molecular switches between proteolysis and signal transduction," *TINS*, vol. 22, No. 10, pp. 439-443 (1999).
Ashkenazi et al., "Death Receptors: Signaling and Modulation," *Science*, vol. 281, pp. 1305-1308 (Aug. 28, 1998).
Barradas et al., "The downregulation of the pro-apoptotic protein Par-4 is critical for Ras-induced survival and tumor progression," *EMBO J.*, vol. 18, No. 22, pp. 6362-6369 (1999).

Baumeister et al., "Human presenilin-1, but not familial Alzheimer's disease (FAD) mutants, facilitate Caenorhabditis elegans Notch signaling independently of proteolytic processing," *Genes & Function*, vol. 1, pp. 149-159 (1997).
Beaucage et al., "Deoxynucleaside Phosphoramidities A New Class of Key Intermediates for Deoxypolynucleotide Synthesis," *Tetrahedron Letters*, vol. 22, No. 20, pp. 1859-1862 (1981).
Beg et al., "An Essential Role for NF-κB in Preventing TNF-α-Induced Cell Death," *Science*, vol. 274, pp. 782-784 (Nov. 1, 1996).
Behl et al., "Glucocorticoids Enhance Oxidative Stress-Induced Cell Death in Hippocampal Neurons *in Vitro*," *Endocrinology*, vol. 138, No. 1, pp. 101-106 (1997).
Berra et al., "Positioning Atypical Protein Kinase C Isoforms in the UV-Induced Appoptotic Signaling Cascade," *Mol. Cell. Biol.*, vol. 17, No. 8, pp. 4346-4354 (1997).
Boussif et al., "A versatile vector for gene and oligonucleotide transfer into cells in culture and *in vivo*: Polyethylenimine," *Proc. Natl. Acad. Sci. USA*, vol. 92, pp. 7297-7301 (Aug. 1995).
Chui et al., "Transgenic mice with Alzheimer presenilin 1 mutations show accelerated naurodegeneration without amyloid plaque formation," *Nature Med.*, vol. 5, No. 5, pp. 560-564 (May 1999).
Deng et al., "Alzheimer-associated presenilin-2 confers increased sensitivity to appoptosis in PC12 cells," *FEBS Letters*, vol. 397, pp. 50-54 (1996).
DeStrooper et al., "A presenilin-1-dependent γ-secretase-like protease mediates release of Notch intracellular domain," *Nature*, vol. 398, pp. 518-522 (Apr. 8, 1999).
Devin et al., "The Distinct Roles of TRAF2 and RIP in IKK Activation by TNF-R1: TRAF2 Recruits IKK to TNF-R1 While RIP Mediates IKK Activation," *Immunity*, vol. 12, pp. 419-429 (Apr. 2000).
Diaz-Meco et al., "ζPKC induces phosphorylation and inactivation of IκB-α *in vitro*," *EMBO J.*, vol. 13, No. 12, pp. 2842-2848 (1994).
Diaz-Meco et al., "Lambda-Interacting Protein, a Novel Protein That Specifically Interacts with the Zinc Finger Domain of the Atypical Protein Kinase C Isotype λ/ι and Stimulates its Kinase Activity In Vitro and In Vivo," *Mol. Cell Biol.*, vol. 16, No. 1, pp. 105-114 (1996).
Diaz-Meco et al., "Inactivation of the Inhibitory κB Protein Kinase/Nuclear Factor κB Pathway by Par-4 Expression Potentiates Tumor Necrosis Factor α-induced Apoptosis," *J. Biol. Chem.*, vol. 274, No. 28, pp. 19606-19612 (Jul. 1999).

(Continued)

*Primary Examiner*—Olga N. Chernyshev
(74) *Attorney, Agent, or Firm*—Morrison & Foerster LLP

(57) ABSTRACT

Disclosed herein are methods for identifying inhibitors of neuronal degeneration, and their use in the treatment of neurodegenerative disorders. In particular methods methods are disclosed for identifying inhibitors of neuronal degeneration or cell death by taking advantage of the involvement of presenilin (PS) and Par-4 in NF-κB activation.

24 Claims, 33 Drawing Sheets

OTHER PUBLICATIONS

Diaz-Meco et al., "The Product of par-4, a Gene Induced during Apoptosis, Interacts Selectivety with the Atypical Isoforms of Protein Kinase C," *Cell*, vol. 86, pp. 777-786 (1996).

Fiers et al., "Complete nucleotide sequence of SV40 DNA," *Nature*, vol. 273, pp. 113-120 (May 11, 1978).

Frengen et al., "A Modular, Positive Selection Bacterial Artificial Chromosome Vector with Multiple Cloning Sites," *Genomics*, vol. 58, pp. 250-253 (1999).

"Methods in Enzymology," *Gene Expression Technology*, vol. 185, Goeddel, D.V. Ed. (1990).

Graham et al., "Characteristics of a Human Cell Line Transformed by DNA from Human Adenovirus Type 5," *J. Gen. Virol.*, vol. 36, pp. 59-72 (1977).

Guo et al., "Increased vulnerability of hippocampal neurons to excitotoxic necrosis in presenilin-1 mutant knock-in mice," *Nature Med.*, vol. 5, No. 1, pp. 101-106 (Jan. 1999).

Guo et al., "Alzheimer's Presenilin Mutation Sensitizes Neural Cells to Apoptosis Induced by Trophic Factor Withdrawal and Amyloid β-Peptide: Involvement of Calcium and Oxyradicals," *J. Neurosci.*, vol. 17, No. 11, pp. 4212-4222 (Jun. 1, 1997).

Guo et al., "Par-4 is a mediator of neuronal degeneration associated with the pathogenesis of Alzheimer disease," *Nature Med.*, vol. 4, No. 8, pp. 957-962 (Aug. 1998).

Guo et al., "Alzheimer's PS-1 mutation perturbs calcium homeostasis and sensitizes PC12 cells to death induced by amyloid β-peptide," *NeuroReport*, vol. 8, No. 1, pp. 379-383 (Dec. 20, 1996).

Haass, "Presenilins: Genes for Life and Death," *Neuron*, vol. 18, pp. 687-690 (1997).

Heck et al., "Insulin-like Growth Factor-1-mediated Neuroprotection against Oxidative Stress is Associated with Activation of Nuclear Factor κB," *J. Biol. Chem.*, vol. 274, No. 14, pp. 9828-9835 (Apr. 2, 1999).

Herreman et al., "Presenilin 2 deficiency causes a mild pulmonary phenotype and no changes in amyloid precursor protein processing but enhances the embryonic lethal phenotype of presenilin 1 deficiency," *Proc. Natl. Acad. Sci. USA*, vol. 96, No. 21, pp. 11872-11877 (Oct. 12, 1999).

Hsu et al., "TNF-Dependent Recruitment of the Protein Kinase RIP to the TNF Receptor-1 Signaling Complex," *Immunity*, vol. 4, pp. 387-396 (Apr. 1996).

Ito et al., "Solid phase synthesis of polynucleotides. VI. Further studies on polystyrene copolymers for the solid support," *Nucleic Acids Res.*, vol. 10, No. 5, pp. 1755-1769 (1982).

Jones et al., "Replacing the complementarity-determining regions in a human antibody with those from a mouse," *Nature*, vol. 321, pp. 522-525 (May 29, 1986).

Kaltschmidt et al., "Brain synapses contain inducible forms of the transcription factor NF-κB," *Mech. Dev.*, vol. 43, pp. 135-147 (1993).

Kaltschmidt et al., "Inhibition of NF-κB potentiates amyloid β-mediated neuronal apoptosis," *Proc. Natl. Acad. Sci. USA*, vol. 96, pp. 9409-9414 (Aug. 1999).

Kelliher et al., "The Death Domain Kinase RIP Mediates the TNF-Induced NF-κB Signal," *Immunity*, vol. 8, pp. 297-303 (Mar. 1998).

Lallena et al., "Activation of IκB Kinase β by Protein Kinase C Isoforms," *Molecular and Cellular Biology*, vol. 19, No. 3, pp. 2180-2188 (Mar. 1999).

Lassam et al., "Synthesis of DNA, Late Polypeptides, and Infectious Virus by Host-Range Mutants of Adenovirus 5 in Nonpermissive Cells," *Virology*, vol. 87, pp. 463-467 (1978).

Lezoualc'h et al., " High Constitutive NF-κB Activity Mediates Resistance to Oxidative Stress in Neuronal Cells," *The Journal of Neuroscience*, vol. 18, No. 9, pp. 3224-3232 (May 1, 1998).

Levitan et al., "Facilitation of *lin*-12-mediated signaling by *sel*-12, a Caenorhabditis elegans S182 Alzheimer's disease gene,"*Nature*, vol. 377, pp. 351-354 (Sep. 1995).

Levy-Lahad et al., "Candidate Gene for the Chromosome 1 Familial Alzheimer's Disease Locus," *Science*, vol. 269, pp. 973-977 (Aug. 18, 1995).

Li et al., "A Role for 12-lipoxygenase in Nerve Cell Death Caused by Glutathione Depletion," *Neuron*, vol. 19, pp. 453-463 (Aug. 1997).

Liu et al., "Dissection of TNF Receptor 1 Effector Functions: JNK Activation is Not Linked to Apoptosis While NF-κB Activation Prevents Cell Death," *Cell*, vol. 87, pp. 565-576 (1996).

MacDonald et al., "NGF-Resistant PC12 Cell Death Induced by Arachidonic Acid is Accompanied by a Decrease of Active PKC Zeta and Nuclear Factor Kappa B," *Journal of Neuroscience Research*, vol. 57, pp. 219-226 (1999).

March, *Advanced Organic Chemistry: Reactions, Mechanisms and Structure*, 4th Ed., John Wiley & Sons, New York, NY (1992).

Matteucci et al., "Synthesis of Deoxyoligonucleotides on a Polymer Support[1]," *J. Amer. Chem. Soc.*, vol. 103, pp. 3185-3191 (1981).

Matteucci et al., "The Synthesis of Oligodeoxypyrimidines on a Polymer Support," *Tetrahedron Letters*, vol. 21, pp. 719-722 (1980).

McCarthy et al., "RIP2 is a Novel NF-κB-activating and Cell Death-inducing Kinase," *The Journal of Biological Chemistry*, vol. 273, No. 27, pp. 16968-16975 (1998).

Morrison et al., "Chimeric human antibody molecules: Mouse antigen-binding domains with human constant region domains," *Proc. Natl. Acad. Sci. USA*, vol. 81, pp. 6851-6855 (Nov. 1984).

Murayama et al., "Direct association of presenilin-1 with β-catenin," *FEBS Letters*, vol. 433, pp. 73-77 (1998).

Ninomiya-Tsuji et al., "The kinase TAK1 can activate the NIK-1κB as well as the MAP kinase cascade in the IL-1 signaling pathway," *Nature*, vol. 398, pp. 252-256 (Mar. 18, 1999).

Nishimura et al., "Presenilin mutations associated with Alzheimer disease cause defective intracellular trafficking of β-catenin, a component of the presenilin protein complex," *Nature Medicine*, vol. 5, No. 2, pp. 164-169 (Feb. 1999).

Ozes et al., "NF-κB activation by tumour necrosis factor requires the Akt serine-threonine kinase," *Nature*, vol. 401, pp. 82-85 (Sep. 2, 1999).

Pomerantz et al., "NF-κB activation by a signaling complex containing TRAF2, TANK and TBK1, a novel IKK-related kinase," *The EMBO Journal*, vol. 18, No. 23, pp. 6694-6704 (1999).

Quon et al., "Formation of β-amyloid protein deposits in brains of transgenic mice," *Nature*, vol. 352, pp. 239-241 (Jul. 18, 1991).

Riechmann et al., "Reshaping human antibodies for therapy," *Nature*, vol. 332, pp. 323-329 (Mar. 24, 1988).

*Remington's Pharmaceutical Sciences*, 18th Edition, Mack Publishing Co., Easton, PA (1990).

Rogaev et al., "Familial Alzheimer's disease in kindreds with missense mutations in a gene on chromosome 1 related to the Alzheimer's disease type 3 gene," *Nature*, vol. 376, pp. 775-778 (Aug. 31, 1995).

Roperch et al., "Inhibition of presenilin 1 expression is promoted by p53 and p21$^{WAF-1}$ and results in apoptosis and tumor suppression," *Nature Medicine*, vol. 4, No. 7, pp. 835-838 (Jul. 1998).

Sambrook et al., Section 16.32-16.37, *Molecular Cloning: A Laboratory Manual*, New York, Cold Spring Harbor Laboratory Press (1989).

Sanz et al., "The interaction of p62 with RIP links the atypical PKCS to NF-κB activation," *The EMBO Journal*, vol. 18, No. 11, pp. 3044-3053 (1999).

Saura et al., "Evidence that Intramolecular Associations between Presenilin Domains are Obligatory for Endoproteolytic Processing," *The Journal of Biological Chemistry*, vol. 274, No. 20, pp. 13818-13823 (May 14, 1999).

Sherrington et al., "Cloning of a gene bearing missense mutations in early-onset familiar Alzheimer's disease," *Nature*, vol. 375, pp. 754-760 (Jun. 29, 1995).

Singleton et al., *Dictionary of Microbiology and Molecular Biology*, 2nd ed., J. Wiley & Sons, New York, NY (1978 & 1987).

Song et al., "Proteolytic release and nuclear translocation of Notch-1 are induced by presenilin-1 and impaired by pathogenic presenilin-1 mutations," *Proc. Natl. Acad. Sci. USA*, vol. 96, pp. 6959-6963 (Jun. 1999).

Taglialatela et al., "Inhibition of Nuclear Factor Kappa B (NFκB) Activity Induces Nerve Growth Factor-Resistant Appoptosis in PC12 Cells," *Journal of Neuroscience Research*, vol. 47, pp. 155-162 (1997).

Takashima et al., "Presenilin 1 associates with glycogen synthase kinase-3β and its substrate tau," *Proc. Natl. Acad. Sci. USA*, vol. 95, pp. 9637-9641 (1998).

Thinakaran et al., "Evidence that Levels of Presenilins (PS1 and PS2) are Coordinately Regulated by Competition for Limiting Cellular Factors," *The Journal of Biological Chemistry*, vol. 272, No. 45, pp. 28415-28422 (Nov. 7, 1997).

Thinakaran, "The role of presenilins in Alzheimer's disease," *The Journal of Clinical Investigation*, vol. 104, No. 10, pp. 1321-1327 (Nov. 1999).

Thinakaran et al., "Endoproteolysis of Presenilin 1 and Accumulation of Processed Derivatives In Vivo," *Neuron*, vol. 17, pp. 181-190 (Jul. 1996).

Tomita et al., "C Terminus of Presenilin is Required for Overproduction of Amyloidogenic Aβ42 through Stabilization and Endoproteolysis of Presenilin," *The Journal of Neuroscience*, vol. 19, No. 24, pp. 10627-10634 (Dec. 15, 1999).

Urlaub et al., "Isolation of Chinese hamster cell mutants deficient in dihydrofolate reductace activity," *Proc. Natl. Acad. Sci. USA*, vol. 77, No. 7, pp. 4216-4220 (Jul. 1980).

Van Antwerp et al., "Suppression of TNF-α-Induced Apoptosis by NF-κB," *Science*, vol. 274, pp. 787-789 (Nov. 1, 1996).

Wang et al., "TNF- and Cancer Therapy-Induced Apoptosis: Potentiation by Inhibition of NF-κB," *Science*, vol. 274, pp. 784-787 (Nov. 1, 1996).

Wang et al., "Parenteral Formulations of Proteins and Peptides: Stability and Stabilizers," *Journal of Parenternal Science and Technology*, Technical Report No. 10, Supp. 42-2S (1988).

Warzocha et al., "Antisense Strategy: Biological Utility and Prospects in the Treatment of Hematological Malignancies," *Leukemia and Lymphoma*, vol. 24, pp. 267-281 (1997).

Wolozin et al., "Participation of Presenilin 2 in Apoptosis: Enhanced Basal Activity Conferred by an Alzheimer Mutation," *Science*, vol. 274, pp. 1710-1713 (Dec. 6, 1996).

Wooten et al., "Function for NF-κB in Neuronal Survival: Regulation by Atypical Protein Kinase C," *Journal of Neuroscience Research*, vol. 58, pp. 607-611 (1999).

Wooten et al., "Mapping of Atypical Protein Kinase C within the Nerve Growth Factor Signaling Cascade: Relationship to Differentiation and Survival of PC12 Cells," *Molecular and Cellural Biology*, vol. 20, No. 13, pp. 4494-4504 (Jul. 2000).

Wu et al., "Inhibition of NF-κB/Rel induces apoptosis of murine B cells," *The EMBO Journal*, vol. 15, No. 17, pp. 4682-4690 (1996).

Yu et al., "The Presenilin 1 Protein is a Component of a High Molecular Weight Intracellular Complex that Contains β-Catenin," *The Journal of Biological Chemistry*, vol. 273, No. 26, pp. 16470-16475 (1998).

Zapata et al., Engineering linear F(ab')$_2$ fragments for efficient production in *Escherichia coli* and enhanced antiproliferative activity, *Protein Engineering*, vol. 8, No. 10, pp. 1057-1062 (1995).

Zhang et al., "Destabilization of β-catenin by mutations in presenilin-1 potentiates neuronal apoptosis," *Nature*, vol. 395, pp. 698-702 (Oct. 15, 1998).

\* cited by examiner

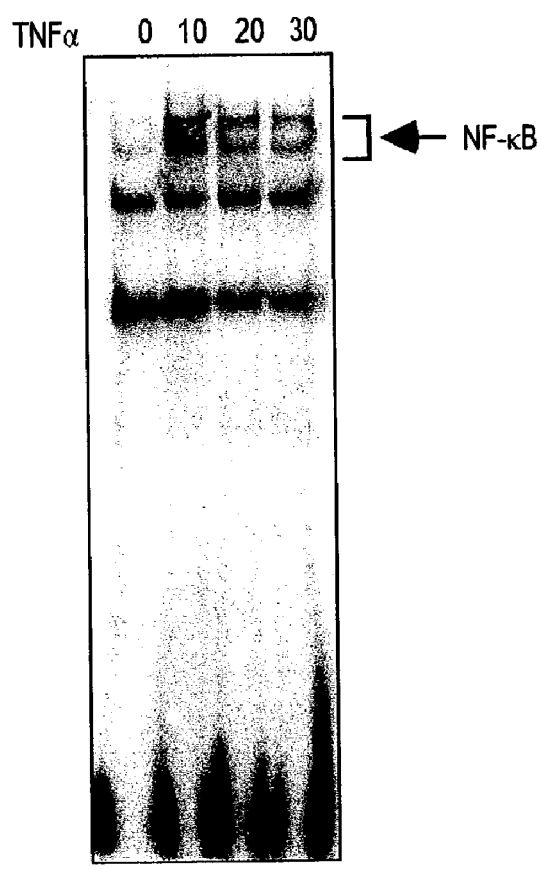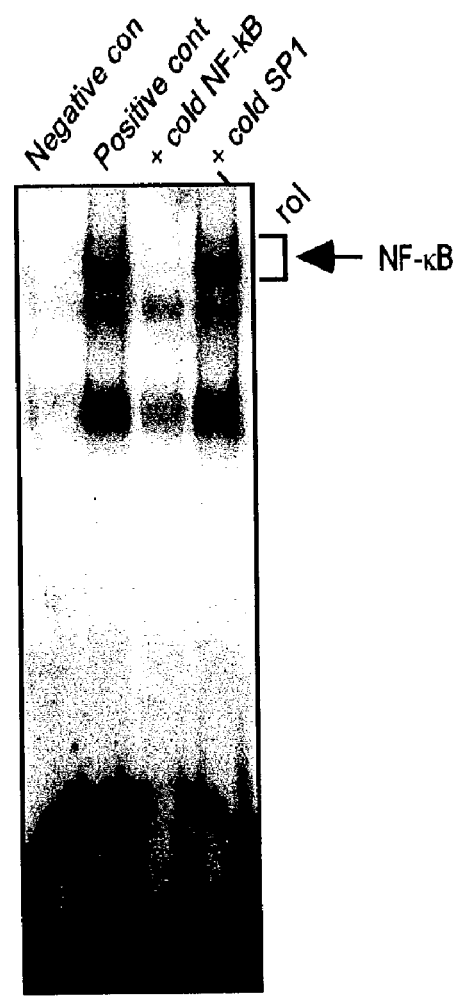
FIG. 6B
FIG. 6C

```
ATGCGCGCCAAGCAGAACCCCCCGGGCCCGGCCCCCCGGGAGGGGGCAGCAGCGACGCCGC
TGGGAAGCCCCCGCGGGGGCTCTGGGCACCCCGGCGGCCGCCGCTGCCAACGAGCTCAACA
ACAACCTCCCGGGCGGCGCGCCGGCCGCACCTGCCGTCCCCGGTCCCGGGGGCGTGAACTGC
GCGGTCGGCTCCGCCATGCTGACGCGGGCGCCCCGGCCCGCGGCCCGCGGCGGTCGGAGGA
CGAGCCCCCAGCCGCCTCTGCCTCGGCTGCACCGCCGCCCCAGCGTGACGAGGAGGAGCCGG
ACGGCGTCCCAGAGAAGGGCAAGAGCTCGGGCCCCAGTGCCAGGAAAGGCAAGGGGCAGATC
GAGAAGAGGAAGCTGCGGGAGAAGCGGCGCTCCACCGGCGTGGTCAACATCCCTGCCGCAGA
GTGCTTAGATGAGTACGAAGATGATGAAGCAGGGCAGAAAGAGCGGAAACGAGAAGATGCAA
TTACACAACAGAACACTATTCAGAATGAAGCTGTAAACTTACTAGATCCAGGCAGTTCCTAT
CTGCTACAGGAGCCACCTAGAACAGTTTCAGGCAGATATAAAAGCACAACCAGTGTCTCTGA
AGAAGATGTCTCAAGTAGATATTCTCGAACAGATAGAAGTGGGTTCCCTAGATATAACAGGG
ATGCAAATGTTTCAGGTACTCTGGTTTCAAGTAGCACACTGGAAAAGAAAATTGAAGATCTT
GAAAAGGAAGTAGTAACAGAAAGACAAGAAAACCTAAGACTTGTGAGACTGATGCAAGATAA
AGAGGAAATGATTGGAAAACTCAAAGAAGAAATTGATTTATTAAATAGAGACCTAGATGACA
TAGAAGATGAAAATGAACAGCTAAAGCAGGAAAATAAAACTCTTTTGAAAGTTGTGGGTCAG
CTGACCAGGTAG
```

FIG. 11A

```
MATGGYRTSSGGGSTTDWKAKRKMRAKNGAGGGSSDAAGKAGAGTAAAAANNNNGGAAAAVG
GGVNCAVGSAMTRAARGRRSDAASASAARDDGVKGKSSGSARKGKGKRKRKRRSTGVVNAAC
DYDDAGKRKRDATNTNAVNDGSSYRTVSGRYKSTTSVSDVSSRYSRTDRSGRYNRDANVSGT
VSSSTKKDKVVTRNRVRMDKMGKKDNRDDDDNKNKTKVVGTRMATGGYRTSSGGGSTTDWKA
KRKMRAKNGAGGGSSDAAGKAGAGTAAAAANNNNGGAAAAVGGGVNCAVGSAMTRAARGRRD
AASASAARDDGVKGKSSGSARKGKGKRKRKR
```

FIG. 11B

```
ATGACAGAGTTACCTGCACCGTTGTCCTACTTCCAGAATGCACAGATGTCTGAG
GACAACCACCTGAGCAATACTGTACGTAGCCAGAATGACAATAGAGAACGGCAG
GAGCACAACGACAGACGGAGCCTTGGCCACCCTGAGCCATTATCTAATGGACGA
CCCCAGGGTAACTCCCGGCAGGTGGTGGAGCAAGATGAGGAAGAAGATGAGGAG
CTGACATTGAAATATGGCGCCAAGCATGTGATCATGCTCTTTGTCCCTGTGACT
CTCTGCATGGTGGTGGTCGTGGCTACCATTAAGTCAGTCAGCTTTTATACCCGG
AAGGATGGGCAGCTAATCTATACCCCATTCACAGAAGATACCGAGACTGTGGGC
CAGAGAGCCCTGCACTCAATTCTGAATGCTGCCATCATGATCAGTGTCATTGTT
GTCATGACTATCCTCCTGGTGGTTCTGTATAAATACAGGTGCTATAAGGTCATC
CATGCCTGGCTTATTATATCATCTATTGTTGCTGTTCTTTTTTTCATTCATT
TACTTGGGGGAAGTGTTTAAAACCTATAACGTTGCTGTGGACTACATTACTGTT
GCACTCCTGATCTGGAATTTTGGTGTGGTGGGAATGATTTCCATTCACTGGAAA
GGTCCACTTCGACTCCAGCAGGCATATCTCATTATGATTAGTGCCCTCATGGCC
CTGGTGTTTATCAAGTACCTCCCTGAATGGACTGCGTGGCTCATCTTGGCTGTG
ATTTCAGTATATGATTTAGTGGCTGTTTTGTGTCCGAAAGGTCCACTTCGTATG
CTGGTTGAAACAGCTCAGGAGAGAAATGAAACGCTTTTTCCAGCTCTCATTTAC
TCCTCAACAATGGTGTGGTTGGTGAATATGGCAGAAGGAGACCCGGAAGCTCAA
AGGAGAGTATCCAAAAATTCCAAGTATAATGCAGAAAGCACAGAAAGGGAGTCA
CAAGACACTGTTGCAGAGAATGATGATGGCGGGTTCAGTGAGGAATGGGAAGCC
CAGAGGGACAGTCATCTAGGGCCTCATCGCTCTACACCTGAGTCACGAGCTGCT
GTCCAGGAACTTTCCAGCAGTATCCTCGCTGGTGAAGACCCAGAGGAAGGGGA
GTAAAACTTGGATTGGGAGATTTCATTTTCTACAGTGTTCTGGTTGGTAAAGCC
TCAGCAACAGCCAGTGGAGACTGGAACACAACCATAGCCTGTTTCGTAGCCATA
TTAATTGGTTTGTGCCTTACATTATTACTCCTTGCCATTTTCAAGAAAGCATTG
CCAGCTCTTCCAATCTCCATCACCTTTGGGCTTGTTTTCTACTTTGCCACAGAT
TATCTTGTACAGCCTTTTATGGACCAATTAGCATTCCATCAATTTTATATCTAG
```

FIG. 12A

MTELPAPLSYFQNAQMSEDNHLSNTVRSQNDNRERQEHNDRRSLGHPEPLSNGRPQGNSRQV
VEQDEEEDEELTLKYGAKHVIMLFVPVTLCMVVVVATIKSVSFYTRKDGQLIYTPFTEDTET
VGQRALHSILNAAIMISVIVVMTILLVVLYKYRCYKVIHAWLIISSLLLLFFFSFIYLGEVF
KTYNVAVDYITVALLIWNFGVVGMISIHWKGPLRLQQAYLIMISALMALVFIKYLPEWTAWL
ILAVISVYDLVAVLCPKGPLRMLVETAQERNETLFPALIYSSTMVWLVNMAEGDPEAQRRVS
KNSKYNAESTERESQDTVAENDDGGFSEEWEAQRDSHLGPHRSTPESRAAVQELSSSILAGE
DPEERGVKLGLGDFIFYSVLVGKASATASGDWNTTIACFVAILIGLCLTLLLLAIFKKALPA
LPISITFGLVFYFATDYLVQPFMDQLAFHQFYI

FIG. 12B

ATGCTCACATTCATGGCCTCTGACAGCGAGGAAGAAGTGTGTGATGAGCGGACGTCCCTAAT
GTCGGCCGAGAGCCCCACGCCGCGCTCCTGCCAGGAGGGCAGGCAGGGCCCAGAGGATGGAG
AGAACACTGCCCAGTGGAGAAGCCAGGAGAACGAGGAGGACGGTGAGGAGGACCCTGACCGC
TATGTCTGTAGTGGGGTTCCCGGGCGGCCGCCAGGCCTGGAGGAAGAGCTGACCCTCAAATA
CGGAGCGAAGCACGTGATCATGCTGTTTGTGCCTGTCACTCTGTGCATGATCGTGGTGGTAG
CCACCATCAAGTCTGTGCGCTTCTACACAGAGAAGAATGGACAGCTCATCTACACGACATTC
ACTGAGGACACACCCTCGGTGGGCCAGCGCCTCCTCAACTCCGTGCTGAACACCCTCATCAT
GATCAGCGTCATCGTGGTTATGACCATCTTCTTGGTGGTGCTCTACAAGTACCGCTGCTACA
AGTTCATCCATGGCTGGTTGATCATGTCTTCACTGATGCTGCTGTTCCTCTTCACCTATATC
TACCTTGGGGAAGTGCTCAAGACCTACAATGTGGCCATGGACTACCCCACCCTCTTGCTGAC
TGTCTGGAACTTCGGGGCAGTGGGCATGGTGTGCATCCACTGGAAGGGCCCTCTGGTGCTGC
AGCAGGCCTACCTCATCATGATCAGTGCGCTCATGGCCCTAGTGTTCATCAAGTACCTCCCA
GAGTGGTCCGCGTGGTCATCCTGGGCGCCATCTCTGTGTATGATCTCGTGGCTGTGCTGTG
TCCCAAAGGGCCTCTGAGAATGCTGGTAGAAACTGCCCAGGAGAGAAATGAGCCCATATTCC
CTGCCCTGATATACTCATCTGCCATGGTGTGGACGGTTGGCATGGCGAAGCTGGACCCCTCC
TCTCAGGGTGCCCTCCAGCTCCCCTACGACCCGGAGATGGAAGAAGACTCCTATGACAGTTT
TGGGGAGCCTTCATACCCCGAAGTCTTTGAGCCTCCCTTGACTGGCTACCCAGGGGAGGGCT
GGAGGAAGAGGAGGAAAGGGGCGTGAAGCTTGGCCTCGGGGACTTCATCTTCTACAGTGTGC
TGGTGGGCAAGGCGGCTGCCACGGGCAGCGGGGACTGGAATACCACGCTGGCCTGCTTCGTG
GCCATCCTCATTGGCTTGTGTCTGACCCTCCTGCTGCTTGCTGTGTTCAAGAAGGCGCTGCC
CGCCCTCCCCATCTCCATCACGTTCGGGCTCATCTTTTACTTCTCCACGGACAACCTGGTGC
GGCCGTTCATGGACACCCTGGCCTCCCATCAGCTCTACATCTGA

FIG. 13A

```
MLTFMASDSEEEVCDERTSLMSAESPTPRSCQEGRQGPEDGENTAQWRSQENEEDGEEDPDR
YVCSGVPGRPPGLEEELTLKYGAKHVIMLFVPVTLCMIVVVATIKSVRFYTEKNGQLIYTTF
TEDTPSVGQRLLNSVLNTLIMISVIVVMTIFLVVLYKYRCYKFIHGWLIMSSLMLLFLFTYI
YLGEVLKTYNVAMDYPTLLLTVWNFGAVGMVCIHWKGPLVLQQAYLIMISALMALVFIKYLP
EWSAWVILGAISVYDLVAVLCPKGPLRMLVETAQERNEPIFPALIYSSAMVWTVGMAKLDPS
SQGALQLPYDPEMEEDSYDSFGEPSYPEVFEPPLTGYPGEELEEEEERGVKLGLGDFIFYSV
LVGKAAATGSGDWNTTLACFVAILIGLCLTLLLLAVFKKALPALPISITFGLIFYFSTDNLV
RPFMDTLASHQLYI
```

FIG. 13B

```
GAATTCGGCACGAGGGGCGCCGCTCGGCTCCCTTCCCGCCCCTGGCTCCCTCCCTCCCTCCCTC
CCTCCTTCTTCTCCCTCCCTCCTGTCCTGGGATTGCCTGGAGCTCCGCACCGCGAGTTTGCCGC
GGCACTTTCCGCGCGGCGGAAGAGCGCGCGCCAGCTTCGGCACACCTGGGAGCCGGATCCCAGC
CCTACGCCTCGTCCCCTACAAGCTCCTCCAAGCCCCGCCGGCTGCTGTGGGAGCGGCGGCCGTC
CCTCTCCTGGAGGTCGTCTCCTGGCATCCTCGGGGCCGCAGGAAGGAAGAGGAGGCAGCGGCCG
GAGCCCTGGTGGGCGGCCTGAGGTGAGAGCCCGACCGGCCCCTTTGGGAAT
```

FIG. 14

```
GAATTCCAGAAGGCAGGAACAGAGAAAGTAGAAGGAAAGTCTTATAAAAGAAAGAGAATAGGCC
AGGCACGGTGGCTCACGCCTCTAATCCCAGCATTTTGGGAGGCTGAGGCAGGTGGATCATGAGG
TCAGGAGTTCAAGACCAACCTGACCAACATGGTGAAGCCCCGTCTCTACTAAAAATACAAAAAT
TAACCAGGCGTGTGTGCCTGTAATCCCAGCTACTCAGGAGGCTGAGGCAGGAGAATCGCTTGAA
CCCGAAAGGTGAAGGTTGCTGTGAGCCTAGATCAGGCCACTGCACTCTGACCTGGGCGACAGAG
CGAGACTCCATGTCAAAGAAAAGAAAGAGGATAAGAAAATTTCCTAACTGGAAGGCAGATAGC
TGATTAAAAGGGTCCACTGACTGCATAACATAATAATGATAAAAGACCAAATCAGAGCATATCT
TCAAGATATTTCAGAGGATCTAAGTAAGAAGATCCAAAAATTTTGAGACAGAAAATACAATGCA
ATCAGAATGCCACTGGTCTTCTAAACAGCAACTCTGGAAACTAGATGATAATAAAGCAATGCCT
TCAAAATTATGAAGGAAATGCTTTCTAACCTAGAGTTCTATGCTCCACCAAACTATTAATCAA
GTATGAAGATAAATTTAAAACATTTTCCAATATGCAAGGTCTCTAAGAATGAGTTATACTATCT
TCAGAATATACTGAGGATATACTCTGCTAAAATGAAGGGGAGAAACAAAAGAGAAAGTATGC
AATTCAGGAAACAAGAAGTCTACAGAGAAATGATTCTCAAGGTGTTAGAGGAGCATAATCCCA
GGATGACCACAAGCAACGAGCCTTAAAATCAGTCCAGATTAGGCCAGGTGCGGTGGCTCACACC
TGTAATCCCAGCACTTTGGGAGGCCAAAGCAGGCTGGTTGCCTGAGCTCAGAAGTTCGAGACCA
GTCTGGGCAACATGGTGAAACCCCGTCTCTACTAAAATACAAAAAATTAGCTGGGCGTGGTGG
CATGTGCCTGTATTCCCAGCTACTCTGGAGGCTGATGCAGGAGAATTGCTTGAACCCAGGAGGC
GGAGGTTGCAGTGAGCCAAGACTGCGCCACTGCACTACAGCCTCACCAACAGAGCGAGACTCCG
TCTCCAAACAAACAAACAAAATCAATCCATATTAAAGCAGGGGATGGAGGGCTCCAGAACAGAT
GTTTCCAAAAGAGAATAGAACTGATAGCTTACCCAATGTGATTAACGTCATTGAGAGGAGGAA
AATTTGAGTATATACTTGTGACTGGTATATAAAAAAATAAGCCGATGATTAAAGAAAAAAAAG
AGGCAAGTTTTAACTGCAGAAAATGGTAAAGACAAAAGGTATAGTTGTGCAACAAGGAAAAC
AGTTGTAAAAAAAAGAAATGCAATCATATACACCACATGACTCAGCTATGAACAGTATTTGTA
TAGTCATAATACTACGGGCGTGTAGGAGTATGAAAAGTATATGTGTGGCCGGGCATGGTGGCTC
ATGCCTGTAATCCCAGAACTTTGGGAGGCCGAGGCGGGTGGATCACGAGGTCAGGAGATCGAGA
TCATCCTGGCTAACACAGTGAAACCCCGTCTCTACTAAAAATGCAAAAAAAAAAAAAAAAAA
AAAAAAATTAGCCGGGCGTGGTGGCAGCCACCTGTAGTCCCAGCTACTCAGGAGGCTGAGGCAG
GAGAATGGCGTGAACCCGGGAGGCGGAGCTTGCAGTGAGCCGAGATCGCGCCACTGCACTCCAG
CCTGGGAGACAGAGCGAGACTCCATCTCAAAAAAAAGAAAAAAAAAGAAAAGAAAAGAAAA
GTATATGTGTTATTAGTGTATTAGAGCTAAATCCTCTTCTATATCTAAAAATGGAAAAATCAAG
ATGTACAATAGCAGATATGCACATAAAAAATAAATATGAAGATCTCTATTAATGGAACCAGTTA
AAAAGTTCAAAGTTTTGGGTAGGGTTTTCAGAATGGATAAGGTAGAGAGGGGATTGCTGTTTTT
TGTTATAATCCTTGTAGAACTAAAGTATGTAATTTTTTATCCTATGCACATATAATATTTGA
TGTTAGAGGATGAATTGCATATGTTCCAGAAATACCTGCATTGAAGGCAAAATGGCTACTTCCC
AATACACTAGCTATCCATACATATAATAATACACTTCCTCAAAATCATTAAGACTAACATCTAG
GTTCACTCTGACATATTTAAATGAATCTGTTTTGTCAGCATTATCATCATATTTCATTTTAT
TATTAAGGGCAAGTGAGTCGCTAAAAATTGGTTATTTTAGGCTAACTCAGAGGTGCTCAACCGG
GGAAGAATTTTATCCCAGGGACCATGTGGCAATGTCACAATACAGGTGGGGGTTTCTTATTGGT
ATCTAATAGGTAGAAGCCAACGATGCTGCTAAACAACCTACAATGGGCAGGACAGCAAAGAATT
ATCCAGCCCCAAATGTAACAGTGCTGAGGTTGAGAAACCAAGCTCCAAGTCTTTGAGGATTATT
TCATCAGAACGCTATACATAAAGATTGATGATATGCAAACATCTTGCAATTTAGGACTGACTCA
GCTAAATACCTCGGTGCAATGTTGGAAGCAGTCTGGCTGTGAAATATATCTTCGGGAATATTGA
GAATGGTAAAGACAAAAGGTATAATAAATGATAATAATAACAAAACACAGAGCTTTGTACCTCA
ATAATCTCTTTCATCCATGGTTCCTAGGGCACTTTATAGACTAATAATACCTACTCTGGTACTC
ACATACCACCTTTTATCTAAGGACTGCAGGCACTTTCACAACACTCTCACGATGCAGGAAGTAT
TATTATCCCCATTTTATATGTAAGTAAACAGAGGCACAAAAGTTAAGCAACTTGCCCAAAGCCA
```

FIG. 15A

```
CACAAGTCAGTAGCAGCCAAAATTCCTGACTCAGAACCTATTAACACTAAGAGAACTGGTCTAA
GCCATGCAGTGATAAATTTATGTGGGGTGTTATCCTAGTTCATTCAAAGTCTATCGTTTTTAGG
CTGATATTGTATATTCAATACCCCATCTGTTATAATTTCCTCTTCTCCCATACACTTCTTAGAG
ACCAAGGACTTTAAGCCCCTAGAAGGGACTATGTTTACTGAGTGCCTTCCTCGAATCAAGCACA
TTTTATGTGCAGTGTCAGTTCTTAAGACAGCTTAAATATAATGTAATTGGGAGGCTGAGAGCAG
GAGAATTGCTTGAACTCAGGAGGCGGAGGTTGCAGTGAGCTGAGATCCCGCCACTGCACTCCAG
CCTGGCGACAGAGCGAGACTCCGCCTCAAAAAAAAAAAAATGTAATTTTGCTGATTTTATAG
TACAGAAAGCTGAGTACCAGATAATGTAAACATGCCCAAGATCTCTCAGCTAGCTGACTATTCC
CTCTTTCCACTATATCCTGCAGCCCTTCCAGGAGAAAAGTCCTCTGATAAGTTACAAAGCATAT
GAATGTGAATACGTTTAATGTCCCAGCCTCCCTTACTCTCCTTAAAACTCAGAAAACAAACTAA
TGAATATGTAATTGAGAAACTTCAGGTGGCACACTGGGGTTGGTACTAGCTTAGGTAAACAGCC
GCTCAGCCTTTTAGACCTATTCCCAACAAAAGCTTTTAATTTTCTAAGGATTTTTCCAGAGCTC
TCGCCATACGTTTCCCACAACAGCCAGACCAAAGACCAAAACTGTCTTTCCCTGAGAAATATAG
AGCATGTGAATCACTTTCTTCTGTTCCCAGTTCTGTGGCAGGCAAACACTGATTGCTCACTCAT
CATGTGCTACCTGGGCAAAACAGGAATATTAAGTAGGAAGAAAGGTTTATGTTAGGTAAGAGCG
TGACTTAGGGCTCTCCTACTTTTTTACAAAATGGAGACCTGGCATTTGTAGCCTCCCACAATGA
TGTGCCCTGACATTACTTGGATATAGAAAGGTCAGTCTTAGGTGCGTCAGTGACAGCCCACCCC
GCTCTGATCCAGAAATTTCAGATGACTTGCATCAGAGGATAAGCCTCTGGCATGTTAATAATGA
AAAAATAGAGACAATCACTGCCCCAGCTCATCTCAAATTAGCATCAGTGCAGGGTTAGTACTTT
GGTAGGGAGCTTTGCTGCTAAATTCATTCTCTGTAAAGAGGAGAGGCAGAGACAGGGTTAAGGG
GAAAACTCCAAGACTGGAATCGCCAATACAATAAACTGTCGAACTGAGTTTTTTCTCCCGCAAC
CCTAAGATACTAGTAAGTCCTTCCTCTTAGCCAACCCTTTTCACCAGGGCACCGCAGTTTTCTT
AGAAGGAGGGTGCTGGGTTTGTCTCAGGTCTTTCTATTCTCCTGCCCGCTGCCCTAGTACATCT
GAAAAGGGAGCAGCGACTAGGAAAAGAGACACGTGGGTATTTTCCCATCCTGTCTAGTCATTCC
CTGAATCATCACAAGTTATCGCACTTTTCCCCTTAGCCAGCAGCGTTCGAGACTTTCTCTCAAA
TAATACGGTCTTGTACTTAAAAGGAAGAGTGGTGGGAGAAGAGAGAGGCGGAGAAGACAAGCAA
GAAGGGCGTGGAGTGCCGTTCCCGCCCCGGAGTCGGAGGCGCCGGGAGGCCGGACGCCGCGAAG
CTGCTAGCCCAGGAATGTGCCGTCTAACTCGCAGGCCGCGGGCGGAGCGCGGCGGGCGCGCTGT
GGTCTGCGGCGGGAGCGGGGCAGAGGACGGCTGGCGCAGGGCAGGCTGCAGCGGCGGGCCGGAC
GCGACGCCGCGCACCTGAGCGCCGGGGCGGGGCGTCAGCGGCCACGACCCTTCCCACCGCGCG
CCGCGCCCCTCGCGCGCCGCCTCGGCCTTTTCCGCTCGTGCTTCGGCGCCGCTCGGCTCCCTTC
CCGCCCCTGGCTCCCTCCCTCCCTCCCTCCTTCTTCTCCCTCCCTCCTGTCCTGGGATTG
CCTGGAGCTCCGCACCGCGAGTTTGCCGCGGCACTTTCCGCGCGGCGGAAGAGCGCGCGCCAGC
TTCGGCACACCTGGGAGCCGGATCCCAGCCCTACGCCTCGTCCCCTACAAGCTCCTCCAAGGTA
AGGCGCTCGCTCACACCCGGTCCTTTCCACGCTCGGCGGGACAGCTGGGTCCCGCCTCCTCTG
CGAACCGGCTAGGAGCTCCGCGCCTCGCCTTGGGAGTGGGGTTGTAGCTGACGGGACCTCGGA
CCGGCGGTGGCTAGAGCGCGGAGCAGGCGATACGACGAGCCGACAGGTGGCGGGTCTAGCCCTA
GTATCTCGACCGCCGCCGGCGCGGACCTTGGTGGGGATGGGGCGGGCGGGCCGACTTGGGGGTG
GGGTCAGTCCTCTCTCCTCCCTTCTAGGGGCGGCGATCGTCGGGGTCCGTACTGTAGGTGCGTG
GGAGAAACTTTGCAGGGTGGGGACCCGGCGGCTGCTGGCCGGTAGTGACTGGTGGGCGCGCTCG
AGGACTCCAAGGGGCGCAGCCCGGGGGCAGACCCTTGGGTCGGGCGGGATCTTACGCTTCCCT
TACCCGCCCCCTTTTGTCTTTCACCTCAGCCCCGCCGGCTGCTGTGGGAGCGGCGGCCGTCCCT
CTCCTGGAGGTCGTCTCCTGGCATCCTCGGGGCCGCAGGAAGGAAGAGGAGGCAGCGGCCGGAG
CCCTGGTGGGCGGCCTGAGGTGAGAGCCCGACCGGCCCCTTTGGGAATATGGCGACCGGTGGCT
ACCGGACCAGCAGCGGCCTCGGCGGCAGCACCACAGACTTCCTGGAGGAGTGGAAGGCGAAACG
CGAGAAGATGCGCGCCAAGCAGAACCCCCGGGCCCGGCCCCCCGGGAGGGGGCAGCAGCGAC
GCCGCTGGGAAGCCCCCGCGGGGGCTCTGGGCACCCCGGCGGCCGC
```

FIG. 15B

METHODS FOR IDENTIFYING INHIBITORS OF NEURONAL DEGENERATION

RELATED APPLICATIONS

This application is a continuation of U.S. application Ser. No. 09/754,949, filed Jan. 4, 2001, which claims the benefit of priority to U.S. Provisional Application No. 60/175,200, filed Jan. 10, 2000, both of which are incorporated by reference in their entirety.

The present invention concerns methods and means for identifying inhibitors of neuronal degeneration, and their use in the treatment of neurodegenerative disorders, such as Alzheimer's disease.

BACKGROUND OF THE INVENTION

Alzheimer's disease is the most common neurodegenerative disorder worldwide. It is characterized by the accumulation of senile plaques in the brains of the affected individuals. The senile plaques consist largely of β-amyloid peptide, derived from proteolytic processing of the β-amyloid precursor protein, β-APP.

While in the majority of cases, Alzheimer's appears to occur as a sporadic disease, in a significant patient population it is genetically inherited as an autosomal dominant trait (familial Alzheimer's disease, FAD). FAD has been determined to be due to mutations in presenilin proteins, PS1 and PS2 (Sherrington et al., Nature 375:754–760 (1995); Levy-Lahad et al., Science 269:973–977 (1995); Rogaev et al., Nature 376:775–778 (1995)). These mutations lead to a gain-of-function which contributes to an early onset and aggressive progression form of Alzheimer's diseases. PS1 and PS2 are ubiquitously expressed as multi-membrane spanning proteins in all mammalian cells examined. The PS proteins display an intracellular localization (both are located in the endoplasmic reticulum (ER) and early Golgi) where they carry out a number of different biological activities, including involvement in cell survival and apoptosis, and specifically Wnt/Wg and Notch signaling.

Numerous reports implicate a role of PS proteins in cell survival and apoptosis. Cells expressing FAD PS appear to be more vulnerable to apoptosis (Wolozin et al., Science 274:1710–1713 (1996)); Guo et al., J. Neurosci. 17:4212–4222 (1997); Deng et al., FEBS Lett. 397: 50–54 (1996)). Likewise, transgenic mice engineered to express FAD PS display a propensity of neuronal death both naturally (Chui et al., Nature Med. 5:560–564 (1999)) and resulting from injury (Gub et al., Nature Med. 5:101–106 (1999)). PS1 is also down-regulated in cell models of p53 mediated apoptosis, again suggesting a critical role for PS in cellular survival (Roperch et al., Nature Med. 4:835–838 (1998)).

PS1 has been observed to physically associate with members of the Wnt/Wg signaling pathway, specifically β-catenin (Yu et al., J. Biol. Chem. 273:16470–16475 (1998); Murayama et al., FEBS Lett. 433:73–77 (1998)) and glycogen synthase kinase 3β (GSK 3β) (Takashima et al., Proc. Natl. Acad. Sci. USA 95:9637–9641 (1998)). Stimulation of the Wnt/Wg pathway transduces an intracellular signal to the nucleus, which activates select genes required for differentiation and/or cell survival. To deliver this signal, GSK 3β is inactivated resulting in the stabilization of β-catenin, followed by translocation of β-catenin to the nucleus where it associates with Tcf/Lef transcription factors to initiate expression of downstream genes. The mechanism by which PS1 affects β-catenin stability is not presently known. However, FAD PS1 reduces both β-catenin stability (Zeng et al., Nature 395:698–702 (1998)) and nuclear translocation (Nishimura et al., Nature Med. 5:164–169 (1999)). FAD PS1 also shows an increased association with GSK 3β as compared to normal PS 1 (Takashima et al., supra).

The role for PS in Notch signaling of cell differentiation is primarily based on genetic evidence. Gene ablation experiments in which PS1 and/or PS2 genes are inactivated results in a developmental lethal phenotype in mouse identical to Notch 1 inactivation (Herreman et al., Proc. Natl. Acad. Sci. USA in press). The genetic homolog of mammalian PS in C. elegans, sel-12, is essential for Notch signaling in this animal (Levitan and Greenwald, Nature 377:351–354 (1995)). Mutations in sel-12 result in Notch signaling defects, which can be rescued by the human PS genes (Baumeister et al., Genes & Function 1:149–159 (1997)). This signaling pathway involves protein processing of Notch where PS appears to mediate this proteolytic step, either directly or indirectly (De Strooper et al., Nature 398:518–522 (1999); Song et al., Proc. Natl. Acad. Sci. USA 96:6959–6963 (1999)).

For further details about the structure and biological role of presenilins see, for example, Haass, Neuron 18:687–690 (1997), Annaert and Strooper, TINS 22:439–444 (1999) and Thinakaran, J. Clin. Invest. 140:1321–1327 (1999).

Another protein that may play a role in the neuronal loss in Alzheimer's disease is Par-4. Par-4, a protein recently implicated as a mediator of prostate cancer, melanoma, and neuronal cell death, has been found to be elevated in vulnerable regions of the Alzheimer's disease brain (Guo et al., Nature Med. 4:957–962 (1998)). Par-4 expression is also elevated in cultured cells expressing FAD PS1 (Guo et al., supra). Inhibition of Par-4 expression or function can prevent neuronal apoptotic cell death induced by β-amyloid or neurotrophic factor withdrawal. In addition, Par-4, has been found to specifically interact with the regulatory domain of atypical protein kinase C subfamily of isoenzymes (aPKCs), which dramatically inhibits their enzymatic activity (Diaz-Meco et al., Cell 86:777–786 (1996)).

The aPKC subfamily has recently been the focus of considerable attention. It is composed of two members, ζPKC and ξ/ζPKC, which appear to be involved in a number of important cellular functions including cell proliferation and survival. The aPKCs selectively bind to, and are inhibited by, Par-4. Consistently, the ectopic expression of Par-4 induces apoptosis in a manner that is dependent on its ability to bind to, and inhibit the aPKCs (Diaz-Meco et al., J. Biol. Chem. 274:19606–19610 (1999)).

While there are numerous factors and pathways that have been implicated in neuronal degeneration, and specifically in Alzheimer's disease, the interaction and relationship of these factors and pathways is not well understood. A better understanding of the cellular mechanisms by which the PS and Par-4 genes exert their biological functions would contribute substantially to our knowledge of the molecular mechanisms causing various neurodegenerative disorders, such as Alzheimer's disease, and is pivotal for the identification and development of drug candidates for the treatment of such diseases.

SUMMARY OF THE INVENTION

The present invention is based on the finding that the PS proteins participate in NF-κB signaling and activation. The invention is further based on the observation that ζPKC is also involved in PS-mediated NF-κB activation. Finally, the invention is based on the finding that Par-4 is a negative regulator of PS-mediated NF-κB activation acting to suppress ζPKC activity. These findings have enabled us to construct a variety of novel screening assays to identify drug candidates for the treatment of neurodegenerative diseases, such as Alzheimer's disease.

In one aspect, the invention concerns a method for identifying inhibitors of neuronal degeneration comprising (a) cotransfecting eukaryotic host cells expressing a presenilin protein (PS), with nucleic acid encoding Par-4, and an NF-κB dependent reporter construct, (b) exposing the cotransfected cells to a candidate molecule, and (c) monitoring the ability of the candidate molecule to induce NF-κB activation. In a particular embodiment, the host cells are exposed to a plurality of candidate molecules and the method is used to select those which induce NF-κB activation.

The host cells may be eukaryotic host cells endogenously expressing a PS protein, and/or cells transfected with DNA encoding a PS protein. The PS protein may, for example, be PS1 or PS2, either normal or FAD. The PS protein may be human. In a preferred embodiment, the host cells are neuronal, e.g. cerebellar granule cells, or organotypic brain cells obtained from a transgenic animal genetically engineered to express a PS protein.

In a preferred embodiment, the NF-κB dependent reporter construct comprises NF-κB-binding consensus sites linked to a luciferase reporter gene. A known inducer of NF-κB activation, such as TNFα may be used as a positive control for NF-κB induction.

The inhibitors of neuronal degeneration identified in accordance with the present invention can be included in pharmaceutical compositions, and administered to patient suffering from or at risk of acquiring a neurodegenerative disease, such as Alzheimer's disease.

In another aspect, the invention concerns a method for identifying inhibitors of neuronal degeneration comprising (a) transfecting eukaryotic host cells endogenously expressing Par-4 and a PS protein with nucleic acid encoding an NF-κB dependent reporter construct, (b) exposing the cotransfected cells to a candidate molecule, and (c) monitoring the ability of the candidate molecule to induce NF-κB activation.

In a further aspect, the invention concerns a method for identifying inhibitors of Par-4 expression or activity comprising (a) transfecting eukaryotic host cells endogenously expressing Par-4 and a presenilin (PS) protein with nucleic acid encoding an NF-κB dependent reporter construct, (b) exposing the transfected cells to a candidate molecule, and (c) monitoring the ability of the candidate molecule to induce NF-κB activation.

In the preceding two aspects of the invention suitable eukaryotic host cells include HeLa cells, and the host cells may be exposed to a plurality of candidate molecules.

In a still further aspect, the invention concerns a method for identifying inhibitors of Par-4 expression or activity comprising (a) transfecting a mammalian cell with nucleic acid comprising a Par-4 promoter region fused to a reporter gene, (b) exposing the cell to a pro-apoptotic agent followed by exposure to a candidate molecule, and (c) monitoring the ability of the candidate molecule to inhibit the activity of the reporter gene. The Par-4 gene is human in one embodiment. In a preferred embodiment, the reporter gene is a luciferase gene, while a suitable cell line is a cell line that endogenously expresses Par-4, such as the HeLa cell line. Preferably, the method is used to screen a plurality of candidate molecules.

In a further aspect, the invention concerns a method for identifying inhibitors of neuronal degeneration comprising (a) exposing eukaryotic host cells expressing presenilin (PS) and Par-4 to a candidate molecule and (b) monitoring the NF-κB DNA binding activity in the cell extract. In a preferred embodiment, the NF-κB DNA binding activity is monitored by electrophoretic mobility shift assay.

In yet a further aspect, the invention concerns a method for identifying inhibitors of neuronal degeneration comprising (a) exposing eukaryotic host cells expressing presenilin (PS) and Par-4 to a candidate molecule and (b) monitoring ζPKC in the cell extract. In a preferred embodiment, ζPKC is monitored by an enzymatic assay.

In another aspect, the invention concerns a method for identifying inhibitors of neuronal degeneration comprising (a) exposing eukaryotic host cells expressing presenilin (PS) and Par-4 to a candidate molecule and (b) monitoring the level of IκB kinase (IKK) phosphorylation. In a preferred embodiment, the level of IκKB kinase (IKK) phosphorylation is measured by metabolic labeling and immunoprecipitation. The immunoprecipitation may be performed with IKK specific antibodies.

In yet another aspect, the invention concerns a method for identifying inhibitors of neuronal degeneration comprising (a) transfecting a mammalian cell with nucleic acid comprising a Par-4 promoter region fused to a reporter gene, (b) exposing the cell to a pro-apoptotic agent followed by exposure to a candidate molecule, and (c) monitoring the ability of the candidate molecule to inhibit the activity of the reporter gene. The reporter gene can be a luciferase gene, while a suitable cell line is a HeLa cell line. Preferably, the method is used to screen a plurality of candidate molecules.

In a different aspect, the invention concerns an isolated polynucleotide molecule comprising a Par-4 promoter region. The Par-4 promoter region may be, for example, from a human Par-4 gene.

The invention also concerns an expression vector comprising a Par-4 promoter region. In one embodiment the expression vector further comprises a heterologous polypeptide, such as a reporter gene, under the control of a Par-4 promoter region. In one embodiment the reporter gene is a luciferase gene. The invention also concerns host cells transformed with such expression vectors.

In a further aspect, the invention concerns a method for producing a heterologous polypeptide by transforming a host cell with a polynucleotide comprising the coding sequence of the polypeptide under control of a Par-4 promoter region and culturing the transformed host cell.

In yet another aspect, the invention concerns a method for identifying inhibitors of neuronal degeneration comprising (a) exposing eukaryotic host cells expressing presenilin (PS) and Par-4 to a candidate molecule, (b) exposing said cell to a pro-apoptotic agent, and (c) monitoring ζPKC in the cell extract. ζPKC may, for example, be monitored by an enzymatic assay.

Another aspect of the invention is a method of inhibiting Par-4 activity in eukaryotic cells comprising introducing into the cells a nucleic acid construct comprising a Par-4 promoter region. The invention also provides a method of preventing neuronal degeneration in a mammal comprising introducing into the mammal a nucleic acid comprising a Par-4 promoter region.

In another embodiment, neuronal degeneration is prevented in a mammal by introducing into the mammal an antisense nucleic acid comprising a sequence complementary to a Par-4 promoter region.

In another aspect the invention concerns inhibitors of neuronal degeneration that are identified through the assays provided.

The invention also concerns a process for obtaining a compound for the treatment of neuronal degeneration in a mammal. The process comprises screening a plurality of compounds for their ability to inhibit Par-4 activity and preparing a pharmaceutical composition comprising one or more of the compounds identified in the screen and a suitable pharmaceutical carrier.

BRIEF DESCRIPTION OF THE DRAWINGS

FIG. 6B shows the results of electrophoretic mobility shift assays indicating that sequence specific NF-κB binding is transiently and maximally enhanced within 10 minutes of treatment with TNFα, thus correlating the association between PS1 and RIP demonstrated in FIG. 6A with TNFα stimulation.

FIG. 6C shows the results of an electrophoretic mobility shift assay.

FIG. 11A shows the nucleotide sequence encoding a human Par-4 protein (SEQ ID NO: 1).

FIG. 11B shows the deduced amino acid sequence of a human Par-4 protein (SEQ ID NO: 2).

FIG. 12A shows the nucleotide sequence encoding a human PS1 protein (SEQ ID NO: 3).

FIG. 12B shows the deduced amino acid sequence of a human PS1 protein (SEQ ID NO: 4).

FIG. 13A shows the nucleotide sequence encoding a human PS2 protein (SEQ ID NO: 5).

FIG. 13B shows the deduced amino acid sequence of a human PS2 protein (SEQ ID NO: 6).

FIG. 14 shows the nucleotide sequence of a human Par-4 5' untranslated region containing transcriptional regulatory elements, including a portion of the promoter sequence (SEQ ID NO: 7).

FIGS. 15A and 15B show the nucleotide sequence of a human Par-4 promoter region and open reading frame (SEQ ID NO: 8). An intron i9s indicated by bold type and the Par-4 protein open reading frame is in bold and underlined.

DETAILED DESCRIPTION OF THE PREFERRED EMBODIMENT

Definitions

Figure 1A:
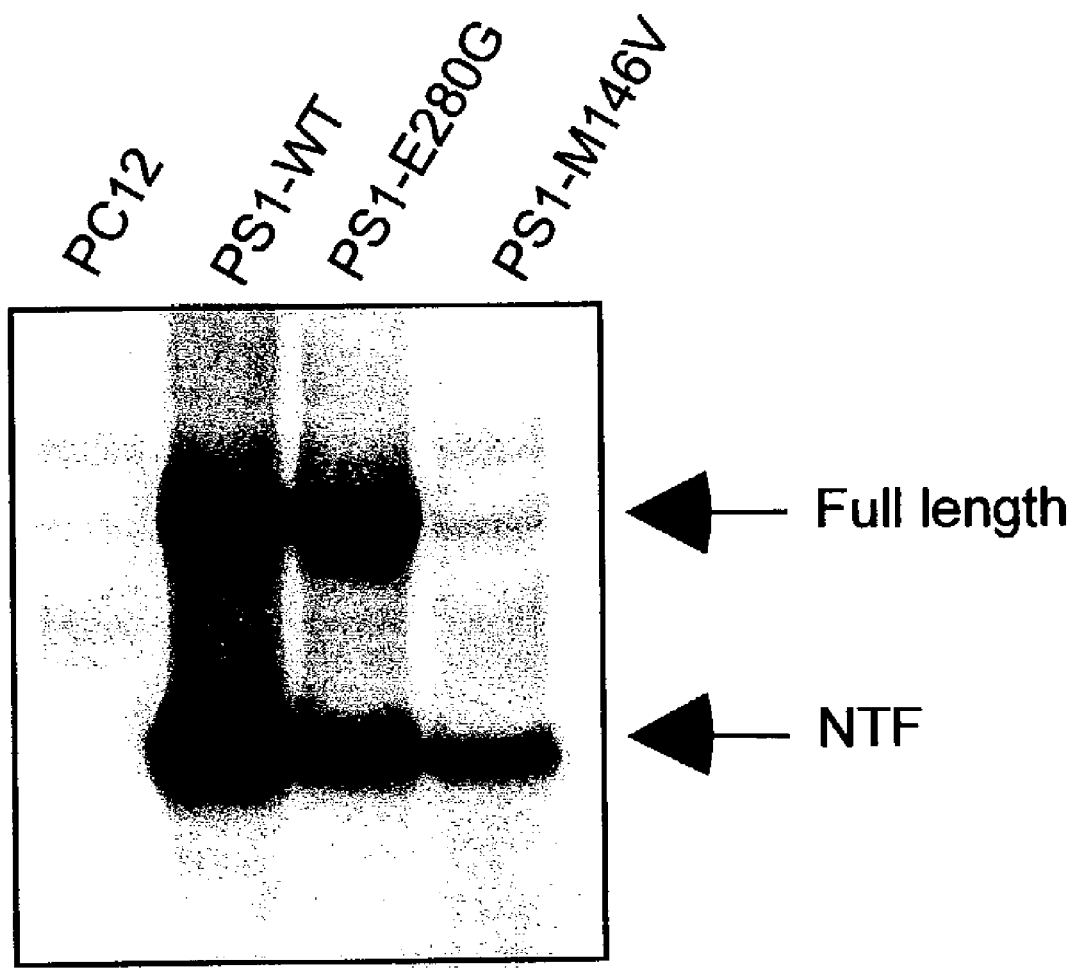
FIG. 1A shows an immunoblot analysis of PS1 protein expression in PC12 stable cell lines.

Unless defined otherwise, technical and scientific terms used herein have the same meaning as commonly understood by one of ordinary skill in the art to which this invention belongs. Singleton et al. (*Dictionary of Microbiology and Molecular Biology,* 2nd ed., J. Wiley & Sons (New York, N.Y. 1994)) and March (*Advanced Organic Chemistry Reactions, Mechanisms and Structure,* 4th ed., John Wiley & Sons (New York, N.Y. 1992)) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

An objective of the present invention is to find inhibitors of neuronal degeneration. The term "neuronal degeneration" is used broadly and refers to any pathological changes in neuronal cells, including, without limitation, death or loss of neuronal cells and any changes that precede cell death. The pathological changes may be spontaneous or may be induced by any event and include, for example, pathological changes associated with apoptosis. The neurons may be any neurons, including without limitation sensory, sympathetic, parasympathetic, or enteric, e.g. dorsal root ganglia neurons, motorneurons, and central neurons, e.g. neurons from the spinal cord. Neuronal degeneration or cell loss is a characteristic of a variety of neurodegenerative disorders.

The terms "neurodegenerative disease" and "neurodegenerative disorder" are used in the broadest sense to include all disorders the pathology of which involves neuronal degeneration and/or disfunction, including, without limitation, peripheral neuropathies, moterneuron disorders, such as amyotrophic lateral sclerosis (ALS), Lou Gehrig's disease, Bell's palsy, and various conditions involving spinal muscular atrophy or paralysis, and other human neurodegenerative diseases, such as Alzheimer's disease, Parkinson's disease, epilepsy, multiple sclerosis, Huntington's chorea, Down's Syndrome, nerve deafness, and Meniere's disease.

"Inhibitors" of neuronal degeneration are molecules, including organic and inorganic small molecules, peptides, proteins, antisense oligonucleotides and antibodies, that are capable of preventing, blocking, arresting, reducing, and/or slowing down the death or degeneration of neuronal cells, in particular neuronal cell death or degeneration that is characteristic of neurodegenerative diseases such as those listed above.

"Inhibitors" of neuronal cell loss are molecules, including organic and inorganic small molecules, peptides, proteins, antisense oligonucleotides and antibodies, that are capable of preventing, blocking, arresting, reducing, and/or slowing down the death of neuronal cells, in particular neuronal cell death that is characteristic of neurodegenerative diseases such as those listed above.

For purposes of this invention, the terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells. It will be understood that, as a result of the degeneracy of the genetic code, a multitude of nucleotide sequences encoding a given polyepeptide may be produced. The present invention specifically contemplates the use of every possible variation of polynucleotide sequences in performing the assays disclosed herein, based upon all possible codon choices. Although nucleic acid molecules which encode the PS or Par-4 proteins or protein fragments herein are preferably capable of hybridizing, under stringent conditions, to a naturally occurring PS or Par-4 gene, it may be advantageous to produce nucleotide sequences which possess a substantially different codon usage. For example, codons may be selected to increase the rate at which expression of the polypeptide occurs in a particular host cell, in accordance with the frequency with which a particular codon is utilized by the host.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

"Antisense oligodeoxynucleotides" or "antisense oligonucleotides" (which terms are used interchangeably) are defined as nucleic acid molecules that can inhibit the transcription and/or translation of target genes in a sequence-specific manner. The term "antisense" refers to the fact that the nucleic acid is complementary to the coding ("sense") genetic sequence of the target gene. Antisense oligonucleotides hybridize in an antiparallel orientation to nascent mRNA through Watson-Crick base-pairing. By binding the target mRNA template, antisense oligonucleotides block the successful translation of the encoded protein. The term specifically includes antisense agents called "ribozymes" that have been designed to induce catalytic cleavage of a target RNA by addition of a sequence that has natural self-splicing activity (Warzocha and Wotowiec, "Antisense strategy: biological utility and prospects in the treatment of hematological malignancies." *Leuk. Lymphoma* 24:267–281 (1997)).

The terms "vector," "polynucleotide vector," "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

An "NF-κB reporter construct" as defined herein is a construct that comprises NF-κB responsive transcriptional regulatory sequences, e.g. promoter sequences, linked to a reporter gene. The reporter gene may be, for example, a luciferase, chloramphenicol acetyltransferase, β-glucuronidase, β-galactosidase, neomycin phosphotransferase, or guanine xanthine phosphoribosyltransferase. In response to NF-κB activation, the NF-κB reporter construct expresses a polypeptide capable of producing a detectable signal.

Similarly, a "Par-4 reporter construct" is defined as a construct that, in response to Par-4 activation, expresses a polypeptide capable of producing a detectable signal.

The term "antibody" is used in the broadest sense and specifically covers monoclonal antibodies (including agonist, antagonist, and neutralizing antibodies), polyclonal antibodies, multi-specific antibodies (e.g., bispecific antibodies), as well as antibody fragments. The monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851–6855 (1984)). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues that are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al. (*Nature,* 321: 522–525 (1986)) and Reichmann et al. (*Nature* 332:323–329 (1988)). The humanized antibody includes a PRIMATIZED® antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8:1057–1062 (1995)); single-chain antibody molecules; and multispecific antibodies formed from antibody fragments.

The "Par-4 promoter region" is used herein to refer to a polynucleotide comprising at least a portion of SEQ ID NO. 8 and capable of functioning as a promoter, corresponding polynucleotide sequences in non-human mammals and variants of such native sequences, so long as they retain the ability to function as a promoter. The variant nucleotide sequences will preferably have at least about 85% nucleotide sequence identity, more preferably at least about 90% nucleotide sequence identity, even more preferably at least about 95% nucleotide sequence identity, most preferably at least about 99% nucleotide sequence identity with the sequence between about nucleotides 1 and 5832 of SEQ ID NO: 8.

"Percent (%) nucleotide sequence identity" is defined herein as the percentage of nucleotides in a candidate sequence that are identical with the nucleotides in the Par-4 promoter sequence, after aligning the sequences and introducing gaps, if necessary, to achieve the maximum percent sequence identity. Alignment for purposes of determining percent nucleic acid sequence identity can be achieved in various ways that are within the skill in the art. These include using publicly available computer software such as BLAST, BLAST-2, ALIGN, ALIGN-2 or MEGALIGN (DNASTAR). The skilled practitioner can determine appropriate parameters for measuring alignment, including any algorithms needed.

"Carrier" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Descrioption of Preferred Embodiments

The nuclear factor kappa B (NF-κB) is a transcription factor that has long been recognized as a central mediator of gene expression induced by pathogens or inflammatory cytokines. More recently, it has been reported that NF-κB can counteract the induction of apoptosis by tumor necrosis factor-α (TNF-α), ionizing radiation, or daunorubicin. See, e.g. Beg et al., *Science* 274:782–784 (1996); Wang et al., *Science* 274:784–787 (1996); van Antwerp et al., *Science* 274:787–789 (1996); Liu et al., *Cell* 87:565–576 (1996); and Wu et al., *EMBO. J.* 15:4682–4690 (1996). According to other reports, insulin-like growth factor-1 (IGF-1) mediated neuroprotection against oxidative stress is associated with NF-κB activation (Heck et al., *J. Biol. Chem.* 274:9828–9835 (1999)). Kaltschmidt et al. found that inhibition of NF-κB potentiates amyloid β mediated neuronal apoptosis (*Proc. Natl. Acad. Sci. USA* 96:9409–9414 (1999)). Highly constitutive NF-κB activity has been described to mediate resistance to oxidative stress in neuronal cells (Lazoualc'h et al., *J. Neurosci.* 18:3224–3232 (1998)). MacDonald et al. (*J. Neurosci Res.* 57:219–226 (1999)) reported that NF-κB, along with protein kinase C zeta (PKCζ), is an essential signaling element for mediating nerve growth factor (NGF)-promoted rescue of neurons from apoptosis. PKCζ has been shown to inactivate I-κBα, a negative regulator of NF-κB (Daiz-Meco et al. *EMBO. J.* 13:2842–2848 (1994)), thereby allowing activation of NF-κB.

The present invention is based on the experimental finding that the presenilin (PS) proteins, which have been suggested to have a critical role in cellular (and in particular neuronal) survival, participate in the molecular pathway mediating NF-κB activation. Although the molecular pathway mediating NF-κB activation is well defined, the participation of PS in this process has not heretofore been described. This finding coupled with the finding that ζPKC is also involved in PS-mediated NF-κB activation, and that Par-4 is a negative regulator of PS-mediated NF-κB activation, acting to suppress ζPKC activity, has led to the development of a variety of screening assays disclosed herein.

The assays of the present invention may be cell-based assays using eukaryotic, preferably mammalian host cells transfected with the desired nucleic acid, e.g. nucleic acid encoding Par-4 and/or a PS protein and an appropriate reporter construct. Alternatively, eukaryotic cells that endogenously express Par-4 and/or PS protein may be used.

Nucleic acid encoding a native human Par-4 protein is known in the art (PCT Publication WO 98/13494, GenBank Accession No: U63809), and is shown in FIG. 11A (SEQ ID NO: 1). The encoded amino acid sequence (SEQ ID NO: 2) is shown in FIG. 11B and the 5' untranslated region of Par-4 including a portion of the promoter sequence is shown in FIG. 14 (SEQ ID NO: 7). Recently we have cloned and sequenced the entire Par-4 promoter region, which is shown in FIG. 15 along with the beginning of the coding region (SEQ ID NO: 8).

A Par-4 promoter region was identified by determining a sequence that could drive expression of a reporter from constructs that operably link a reporter gene to Par-4 sequences (Par-4 promoter-reporter constructs). It was identified using a Par-4 coding region of human origin. Briefly, a Par-4 cDNA clone was isolated and used to generate a radiolabeled probe which was then hybridized to a bacterial artificial chromosome library containing segments of the human genome (Frengen et al., *Genomics* 58:250–253 (1999)). Positive-hybridizing isolates were identified and partial DNA sequence analysis confirmed that they harbored human Par-4 coding sequences. Upon confirmation that the isolates contained Par-4 coding sequence, the coding region was mapped within the isolated segment of DNA by standard mapping procedures involving restriction endonuclease fragmentation and radiolabeled Par-4 hybridization. The regions 5' to the coding domain of three isolates were merged using common restriction endonuclease sites to produce one contiguous piece of DNA containing the human Par-4 promoter. This contig was sequenced out to approximately 5900 base pairs 5' to the initiator methionine of the human Par-4 protein. Using site-directed mutagenesis, a unique restriction site was introduced immediately before the initiator methionine. An expression construct was created that comprised nucleotides 1 through 5744 of SEQ ID NO: 8, linked to a luciferase reporter gene. The expression construct was transiently transfected into mammalian 293HEK cells with Fugene 6 (Becton Dickinson) or an equivalent reagent. Apoptosis was induced in the cells approximately 24 to 72 hours later using an apoptotic stimulus such as etoposide or ceramide. Cell lysates were prepared at various time points following insult and reporter activity assayed appropriately. The ability of the Par-4 promoter region to drive expression of the reporter was observed. Reporter activity was significantly greater from the Par-4 promoter-reporter constructs than that obtained with reporter plasmid lacking the human Par-4 promoter sequence.

Potential regulatory sites are identified by sequence analysis with programs such as FIND PROGRAM (University of Wisconsin Genetics Computer Group Software Program) and TESS (Transcription Element Search Software) using the TRANSFAC database (Research Group/AG Bioinformatik). Potential regulatory sites are confirmed by co-transfecting mammalian cells with a Par-4 promoter-reporter construct and plasmids encoding activators or repressors of a given regulatory element.

At least one intron, identified in bold in FIG. 15, is located in the Par-4 promoter. This intron is located in the 5' untranslated region and was identified by comparing the gene sequence with a Par-4 cDNA sequence.

Based on the identification of the sequence of a Par-4 promoter region, several inhibitors of Par-4 activity and neuronal degeneration were identified. These include a nucleic acid construct comprising a Par-4 promoter region and a nucleic acid construct comprising a sequence complementary to a Par-4 promoter region. Par-4 activity may be inhibited and neuronal degeneration may be prevented in a mammal by introducing into the mammal an effective amount of any of the identified inhibitors.

The cloning of human presenilin-1 (PS1) is described in Sherrington et al., Nature 375:754–760 (1995). The human PS1 nucleotide sequence and deduced amino acid sequence are shown in FIGS. 12A and 12B, SEQ ID NOs: 3 and 4, respectively. The cloning of human presenilin-2 (PS2) is described in Levy-Lahad et al., Science 269:973–977 (1995) and Rogaev et al., Nature 376:775–778 (1995). The human PS2 nucleotide sequence and the deduced amino acid sequence are shown in FIGS. 13A and 13B, SEQ ID NOs: 5 and 6, respectively.

DNA encoding a native polypeptide used in the assays of the present invention, including the human Par-4, PS1 and PS2 polypeptides, can be obtained from cDNA libraries prepared from tissue believed to possess the corresponding mRNA and to express it at a detectable level. For example, a cDNA library can be constructed by obtaining polyadenylated mRNA from a cell line known to express the desired polypeptide, and using the mRNA as a template to synthesize double-stranded cDNA. In the present case, PS1 and PS2 are ubiquitously expressed as multi-transmembrane domain proteins in all mammalian cells examined. Accordingly, the corresponding mRNA can be isolated from a variety of sources. Par-4 is also expressed in a variety of mammalian cells, often along with PS1 and/or PS2. For example, HeLa cells naturally show activated expression of endogenous Par-4, and may serve as a source for Par-4 mRNA.

The polypeptide genes necessary to practice the present invention can also be obtained from a genomic library, such as a human genomic cosmid library.

Libraries, either cDNA or genomic, are screened with probes designed to identify the gene of interest or the protein encoded by it. For cDNA expression libraries, suitable probes include monoclonal and polyclonal antibodies that recognize and specifically bind to a given polypeptide. For cDNA libraries, suitable probes include oligonucleotide probes (generally about 20–80 bases) that encode known or suspected portions of a polypeptide herein, from the same or different species, and/or complementary or homologous cDNAs or fragments thereof that encode the same or a similar gene. Appropriate probes for screening genomic libraries include, without limitation, oligonucleotides, cDNAs, or fragments thereof that encode the same or a similar gene, and/or homologous genomic DNAs or fragments thereof. Screening the cDNA and genomic libraries with the selected probe may be conducted using standard protocols as described, for example, in Chapters 10–12 of Sambrook et al., *Molecular Cloning: A Laboratory Manual*, New York, Cold Spring Harbor Laboratory Press (1989).

According to a preferred method, carefully selected oligonucleotide probes are used to screen cDNA libraries from various tissues, preferably from neuronal tissues. The oligonucleotide sequences selected as probes should be sufficient in length and sufficiently unique and unambiguous that false positives are minimized. The actual sequences can be designed based on regions that have the least codon redundancy. The oligonucleotides may be degenerate at one or more positions. The use of degenerate oligonucleotides is of particular importance where a library is screened from a species in which preferential codon usage is not known.

The oligonucleotides must be labeled such that they can be detected upon hybridization to DNA in the library screened. Preferably, the 5' end of the oligonucleotide is radiolabeled, using ATP (e.g. $\gamma^{32}P$) and polynucleotide kinase. However, other labeling, e.g. biotinylation or enzymatic labeling are also suitable.

Alternatively, to obtain DNA encoding a homologue of a human PS or Par-4 polypeptide in another mammalian species, one only needs to conduct hybridization screening with labeled human DNA or fragments thereof, selected following the principles outlined above, in order to detect clones which contain homologous sequences in the cDNA libraries obtained from appropriate tissues of the particular animal (cross-species hybridization). Full-length clones can then be identified, for example, by restriction endonuclease analysis and nucleic acid sequencing. If full-length clones are not identified, appropriate fragments are recovered from the various clones and ligated at restriction sites common to the fragments to assemble a full-length clone.

cDNAs used in practicing the present invention can also be identified and isolated by other known techniques, such as by direct expression cloning or by using the PCR technique, both of which are well known are described in textbooks, such as those referenced herein.

Once the sequence is known, the nucleic acid can also be obtained by chemical synthesis, following known methods, such as the phosphoramidite method (Beaucage and Caruthers, *Tetrahedron Letters* 22:1859 (1981); Matteucci and Caruthers, *Tetrahedron Letters* 21:719 (1980); and Matteucci and Caruthers, *J. Amer. Chem. Soc.* 103: 3185 (1981)), and the phosphotriester approach (Ito et al., *Nucleic Acids Res.* 10:1755–1769 (1982)).

In order to perform the cell based assays herein, or for introduction into a transgenic animal, cDNA encoding the desired polypeptide of the present invention is inserted into a replicable vector. Suitable vectors are prepared using standard techniques of recombinant DNA technology, and are, for example, described in the textbooks cited above. Isolated plasmids and DNA fragments are cleaved, tailored, and ligated together in a specific order to generate the desired vectors. After ligation, the vector containing the gene to be expressed is transformed into a suitable host cell.

The cell-based assays of the present invention use eukaryotic, preferably vertebrate, more preferably mammalian host cells. Cell cultures derived from multicellular organisms suitable for practicing the present invention include, for example, monkey kidney CV1 cell line transformed by SV40 (COS-7, ATCC CRL 1651); human embryonic kidney cell line 293S (Graham et al, *J. Gen. Virol.* 36:59 (1977)); baby hamster kidney cells (BHK, ATCC CCL 10); Chinese hamster ovary (CHO) cells (Urlaub and Chasin, *Proc. Natl. Acad. Sci. USA* 77:4216 (1980)); monkey kidney cells (CVI-76, ATCC CCL 70); African green monkey cells (VERO-76, ATCC CRL-1587); human cervical carcinoma cells (HeLa, ATCC CCL 2); canine kidney cells (MDCK, ATCC CCL 34); human lung cells (W138, ATCC CCL 75); human liver cells (Hep G2, HB 8065), or PC12 cells.

Cells endogenously expressing Par-4 and/or a PS polypeptide might be preferred in some embodiments. For example, in one embodiment of the present invention, the host cells are primary cultures of rat cerebellar granule neurons prepared from 8-day old Sprague-Dawley rats, essentially as described in Kaltschmidt et al., *Mech. Dev.* 43:135–147 (1993). Neurons dissociated from cerebellum can be plated on plastic dishes coated with poly-L-lysine, and growth in basal modified Eagle's medium containing 10% heat-inactivated fetal calf serum, 25 mM KCl, 1 mM glutamine and 100 µg/ml gentamycin, essentially as described by Heck et al., *J. Biol. Chem.* 274:9828–9835 (1999), or by a modification of this or other methods known in the art. The cerebellar neurons are then transiently transfected with the desired expression construct, for example, as described by Boussif et al., *Proc. Natl. Acad. Sci. USA* 92:7297–7301 (1995), including an appropriate NF-κB dependent reporter gene, e.g. a luciferase gene linked to NF-κB consensus binding sites. Luciferase activity can be monitored, for example, as described in Behl et al., *Endocrinology* 138:101–106 (1997).

In another embodiment, organotypic brain cells are obtained from transgenic mice that have been genetically engineered to express PS1 and/or Par-4. Methods of making transgenic mice are well known in the art.

Genetic information can be transferred into mammalian cells essentially by two types of methods, those that are mediated by virus infection and those based on direct DNA transfer. Direct methods involve the introduction of genetic material (e.g. DNA) into the nucleus of a somatic cell, or the male pronucleus of a fertilized egg, by microinjection. Indirect methods most commonly involve delivery of genetic information by viral vectors, particularly viral RNA vectors. The viral vector systems may use papoviruses, of which Simian Virus 40 (SV40) and polyoma virus are the best studied. Accordingly, suitable promoters for mammalian expression vectors are often of viral origin. In addition to SV40 and polyoma virus, these viral promoters are commonly derived from cytomegolavirus (CMV), and Adenovirus2. The SV40 virus contains two promoters that are termed the early and late promoters. They are both easily obtained from the virus as one DNA fragment that also contains the viral origin of replication (Fiers et al., *Nature* 273:113 (1978)). Smaller or larger SV40 DNA fragments may also be used, provided they contain the approximately 250-bp sequence extending from the HindIII site toward the BglI site located in the viral origin of replication. An origin of replication may be obtained from an exogenous source, such as SV40 or other virus, and inserted into the cloning vector. Alternatively, the host cell chromosomal mechanism may provide the origin of replication. If the vector containing the foreign gene is integrated into the host cell chromosome, the latter is often sufficient.

One of the most commonly used methods of introducing DNA into mammalian cells is the calcium phosphate method (Graham et al., *Virology* 52:546 (1978); Sambrook et al., *supra*, *sections* 16.32–16.37). However, other methods, e.g. lipofection, DEAE-dextran mediated DNA transfection, protoplast fusion, electroporation, polybrene-mediated DNA transfection, red blood cell-mediated transfection, direct microinjection, laser method, and microprojectile-mediated gene transfer etc. are also suitable. These and similar methods are disclosed, for example, in "Methods in Enzymology," Vol. 185, *Gene Expression Technology*, Goeddel, D. V. ed., (1991).

The screening assays of the present invention are preferably amenable to high-throughput screening of chemical libraries, and are particularly suitable for identifying small molecule drug candidates. Small molecules, which are usually less than 10K molecular weight, are desirable as therapeutics since they are more likely to be permeable to cells, are less susceptible to degradation by various cellular mechanisms, and are not as apt to elicit an immune response as proteins. Small molecules include but are not limited to synthetic organic or inorganic compounds, and peptides. Many pharmaceutical companies have extensive libraries of such molecules, which can be conveniently screened by using the assays of the present invention. The assays can be performed in a variety of formats, including biochemical screening assays, protein-protein binding assays, immunoassays, cell-based assays, etc. Such assay formats are well known in the art.

For example, a biochemical assay for identifying inhibitors of Par-4 expression, neuronal apoptosis and neuronal degeneration may be carried out using a Par-4 promoter-reporter construct. A Par-4 promoter region containing the regulatory domains necessary for apoptotic induction is fused to a reporter gene. The reporter gene may be any known in the art, such as luciferase. The Par-4 promoter-reporter construct is transfected into mammalian cells. For example, the Par-4 promoter-reporter construct may be transfected into 293HEK cells using a transfection reagent such as Fugene6 (Becton Dickinson). The cells are then grown for a period of time, preferably 24 hours, and then exposed to a stimulus known to induce apoptosis, such as a pro-apoptotic agent like etoposide or ceramide. The compound to be screened is added to the cells and the cells are incubated for a second period of time, preferably 6 to 24 hours. Cell lysates are then prepared and reporter activity is measured using the appropriate assay. A compound that is observed to decrease induction of reporter activity compared to untreated controls is considered a candidate inhibitor of Par-4 expression and neuronal apoptosis and degeneration. It is anticipated that incubation times, reagent concentrations and other variables will be optimized to produce the most sensitive assay possible.

A high throughput version of this assay may be developed to allow for the rapid screening of thousands of candidate inhibitors. For example, the assay may be scaled down so that it can be carried out in 96 well plates and the cell lysate preparation and reporter activity determination can be carried out robotically.

If a candidate compound is identified in this assay, its inhibitory properties may be confirmed in a secondary assay using neuronal cells. For example, rat PC12 cells and/or human SK-N-MC neuronal cell lines may be transiently transfected with the Par-4 promoter-reporter construct and tested as described above. Alternatively a neuronal cell line may be stably transfected with the reporter construct and used to test the candidate compound.

In addition, a candidate inhibitory compound may be tested in an assay using naïve neuronal cells treated with an apoptotic stimulus. The ability of the candidate compound to inhibit endogenous Par-4 expression compared to untreated cells is observed.

A biochemical assay may also be used to identify inhibitors of neuronal degeneration by screening for antagonists of Par-4 mediated inhibition of PS1 induced NF-κB activation. Several different types of biochemical assay may be used. For example, an NF-κB reporter construct may be transfected into mammalian cells that either endogenously express PS1 and Par-4 or are transfected to express these proteins. The compound to be screened is added to the cells. A compound that increases NF-κB reporter activity compared to control cells is considered a candidate inhibitor of Par-4 activity and neuronal degeneration.

Alternatively, a DNA binding assay known as a gel shift or electrophoretic mobility shift assay (EMSA) may be used. In a typical electrophoretic mobility shift assay, cells endogenously expressing PS1 (wild type or FAD) and Par-4, or transfected to express these proteins, are incubated with a candidate molecule. Nuclear or whole cell extracts are then prepared and incubated with a synthetic, $^{32}$P labeled, double-stranded oligonucleotide containing consensus NF-κB recognition sequence, fractionated on polyacrylamide gel, and autoradiographed. The positive molecules are identified by their ability to stimulate NF-κB DNA binding activity.

Another biochemical assay that can be used for identifying inhibitors of neuronal degeneration is an enzymatic assay to monitor the activity of ξPKC. As described earlier, ξPKC is involved in PS1 induced NF-κB activation. Moreover, Par-4 directly binds to ξPKC and inactivates it, resulting in the inhibition of PS1 induced NF-κB activation. This assay can be conducted by incubating cells expressing PS1 and Par-4 with a candidate molecule, and monitoring ξPKC in the cell extracts. As described earlier, cells expressing exogenously transfected PS1 and Par-4 can also be used for the assay. The assay for monitoring ξPKC is well established (Berra et al. *Mol. Cell. Biol.* 17:4346 (1997); Barradas et al., *EMBO. J.* 18:6362 (1999)). Molecules of interest show an ability to stimulate ξPKC. This assay may also be carried out following exposure to a pro-apoptotic agent. The increased Par-4 expression produced by such an exposure would make the assay more sensitive by increasing the baseline inhibition of ξPKC.

Yet another biochemical assay that is useful for identifying inhibitors of neuronal degeneration is an assay to monitor the level of phosphorylation of IKK (IκB kinase) in extracts prepared from cells treated with a candidate molecule. According to the working hypothesis underlying the current invention, PS1 stimulates ξPKC, which activates IKK by phosphorylation, which in turn phosphorylates and induces degradation of IκB, thus releasing active NF-κB. Thus the phosphorylation status of IκB or IKK can serve as a surrogate marker of NF-κB activation. Monitoring the phosphorylation state of IκB may be difficult due to rapid degradation. However, phosphorylated IKK can be monitored by incubating cells treated with a candidate molecule and metabolically labeled with $^{32}Pi$, immunoprecipitating IKK in the cell extract using IKK specific antibodies, and resolving on SDS-PAGE gel followed by autoradiography. Those molecules that antagonize the inhibitory effect of Par-4 on NF-κB activation are scored based on their ability to increase the level of phosphorylation of IKK.

Once a candidate inhibitor of neuronal degeneration has been identified by the assays of the present invention, it can be further tested by one or more cell survival or viability assays known in the art. These include, but are not limited to, the 3-(4,5-dimethylthiazol-2-yl)-2,5-diphenyl-tetrazolium bromide (MTT) reduction cell viability assay, which is a sensitive first indicator of mitochondrial damage, the trypan blue exclusion assay, and morphological studies. These and similar assays are described, for example, in MacDonald et al., *J. Neurosci. Res.* 57:219–226 (1999), Heck et al., supra, and in the references cited therein.

The toxicity and therapeutic efficacy of identified inhibitors of neuronal degeneration can be determined by standard pharmacological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography.

The inhibitors of neuronal degeneration identified in accordance with the present invention can be formulated as pharmaceutical compositions for use in the treatment of various neurodegenerative diseases, such as Alzheimer's disease. Pharmaceutical compositions can be formulated for a variety of modes of administration, including systemic, localized and topical administration. Techniques and formulations generally may be found in *Remington's Pharmaceutical Sciences*, 18th Edition, Mack Publishing Co. (Easton, Pa. 1990). See also, Wang and Hanson "Parenteral Formulations of Proteins and Peptides: Stability and Stabilizers," *Journal of Parenteral Science and Technology*, Technical Report No. 10, Supp. 42-2S (1988).

A suitable administration format can best be determined by a medical practitioner for each patient individually. The amounts of various compounds for use in the methods of the invention can be determined by standard procedures. Generally, a therapeutically effective amount is between about 100 mg/kg and $10^{-12}$ mg/kg, but will vary depending on the age and size of the patient, and the disease or disorder associated with the patient. Generally, it is an amount between about 0.05 and 50 mg/kg of the individual to be treated. The determination of the actual dose is well within the skill of an ordinary physician.

Further details of the invention are illustrated by the following non-limiting examples.

EXAMPLES

Example 1

PS1 appears to play a critical role in maintaining cell viability. Rat neuronal PC12 cells were stably transfected with cDNA encoding either wild-type human PS1 (PS1-WT) or PS1 with the M146V or E280G mutations seen in FAD (PS51-FAD). The cDNAs encoding full length WT, M146V, or E280G PS1 were engineered for neuronal expression using the neuronal-specific enolase (Quon et al., *Nature* 352:239–241 (1991)). Each construct was co-transfected into PC12 cells with a second plasmid carrying the selectable marker neomycin, using LIPOFECTAMINE (Life Sciences Inc.). After transfection, pools were selected from which individual clones were isolated. Clones were assessed for human PS1 expression, as well as NTF/CTF processing by Western blot analysis. Briefly, monoclonal antibody 3.6.1, specific for human PS1, was prepared by immunizing mice with a synthetic peptide spanning residues 309–331 of PS1 and rat anti-human PS1 antibody was obtained from Chemicon. Equal amounts of total cell proteins (50 μg) were separated by SDS-PAGE, transferred to nitrocellulose membrane and incubated with antibody.

Analysis using mAb 3.6.1 and Rat anti-PS1 (Chemicon) showed that PS1-WT and PS1-FAD mutants expressed at variable levels in the selected lines (FIG. 1A). The position of the PS1 full-length holoprotein (FL) and the ~30 KDa PS1 N-terminal fragment (NTF) are indicated in FIG. 1A.

A set of WT, M146V, and E280G PS1 cell clones were selected based on expression levels of human PS1. Stable PS1 expressing PC12 cells were cultured in DMEM containing 5% fetal calf serum, 10% horse serum and antibiotics (50 units/ml penicillin and 50 µg/ml streptomycin) in the presence of 500 µg/ml Geneticin (Life Technologies). Cell cultures were maintained in a 95% air: 5% $CO_2$ atmosphere. Consistent with previous reports (Guo et al., *Neuroreport* 8:379–383 (1996)), during normal maintenance of these cultures, expression of either PS1-WT or PS1-FAD mutants did not affect cell proliferation or viability.

To determine whether expression of PS1-FAD mutants affected susceptibility to apoptosis, apoptosis was induced by treatment with etoposide (25 µg/ml) or by serum withdrawal for 27 hours. Cell viability was determined by propidium iodide staining and assessed by flow cytometry. Viable or apoptotic cells were distinguished based on morphological alterations typical of adherent cells undergoing apoptosis including becoming rounded, condensed, membrane blebbing and detaching from the culture dish. Briefly, following the induction of apoptosis as indicated in experiments, culture media was collected and the cells were harvested by trypsinization. The cell media and trypsinized cells were centrifuged and washed once in chilled PBS. The cell pellets were re-suspended in 1 ml of staining solution (50 mg/ml-propidium iodide, 20 µg/ml RNase A, 0.6% NP-40, and 0.1% sodium citrate) and incubated on ice for 30 minutes. Cells were then analyzed by flowcytometry (Becton Dickinson). The percentage of apoptotic cells was determined by calculating the percentage of cells with sub-$G_0/G_1$ DNA content.

Figure 1B:
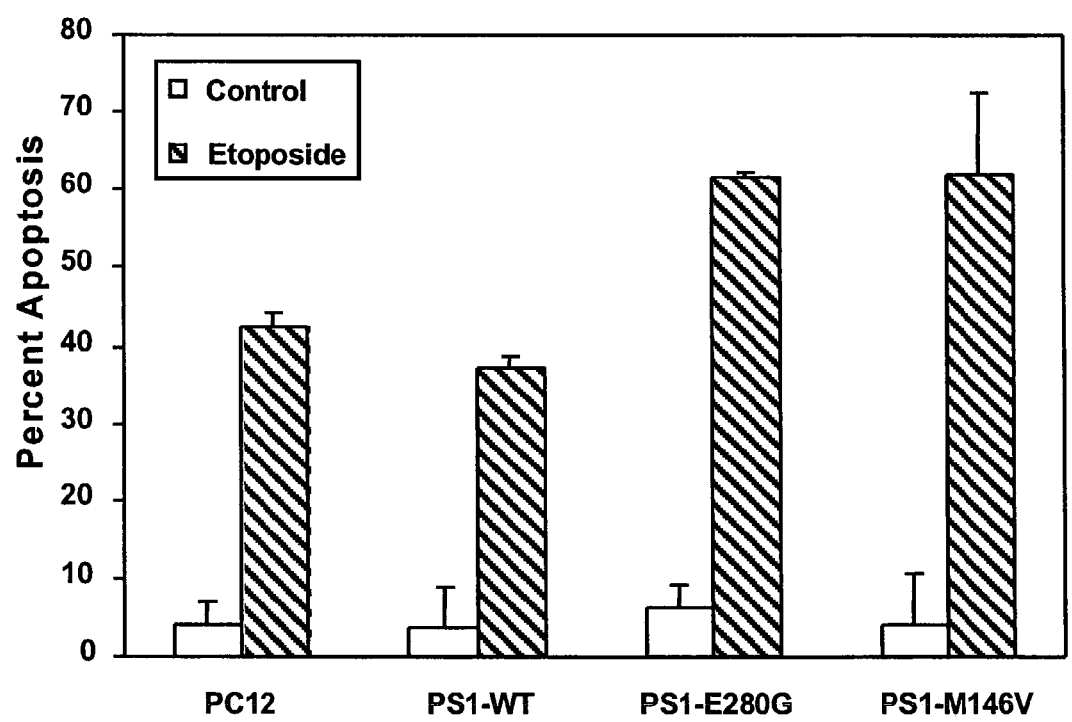
FIG. 1B shows the ability of etoposide treatment to induce apoptosis in PC12 cells stably expressing PS1-WT or PS1-FAD mutant proteins.
Figure 1C:
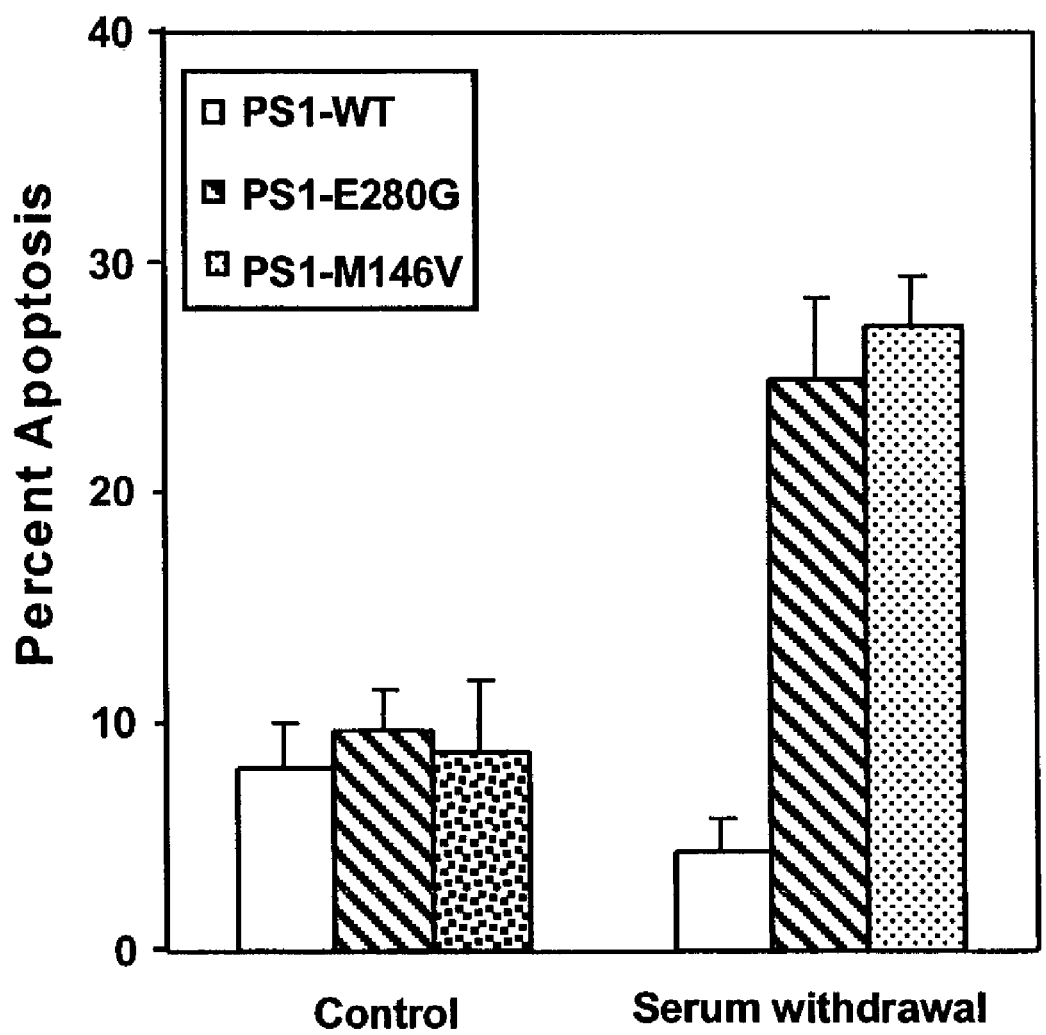
FIG. 1C shows the ability of serum withdrawal to induce apoptosis in PC12 cells stably expressing PS1-WT or PS1-FAD mutant proteins.

Following etoposide treatment, naïve and PS1-WT expressing PC12 cells displayed a progressive increase in the number of apoptotic cells (FIG. 1B). In comparison, PC12 cells expressing PS1-FAD mutants showed a significant enhancement in their susceptibility to etoposide, with increased numbers of apoptotic cells present 12 hours after exposure to etoposide (FIG. 1B). In another set of experiments, cells were induced to undergo apoptosis by serum withdrawal. Again, as assessed by flow cytometry cells expressing PS1-FAD mutants were significantly more sensitive to apoptosis when compared to naïve and PS1-WT expressing cells (FIG. 1C). The propidium iodide profile indicated that serum withdrawal for 27 hours induced apoptosis (sub-$G_0/G_1$) in ~5% of naïve and PS1-WT expressing cells and in ~30% of cells expressing PS1-FAD mutants. Despite the lower levels of PS1-FAD expression compared to PS1-WT, expression levels were sufficient to produce a pro-apoptotic effect.

Figure 1D:
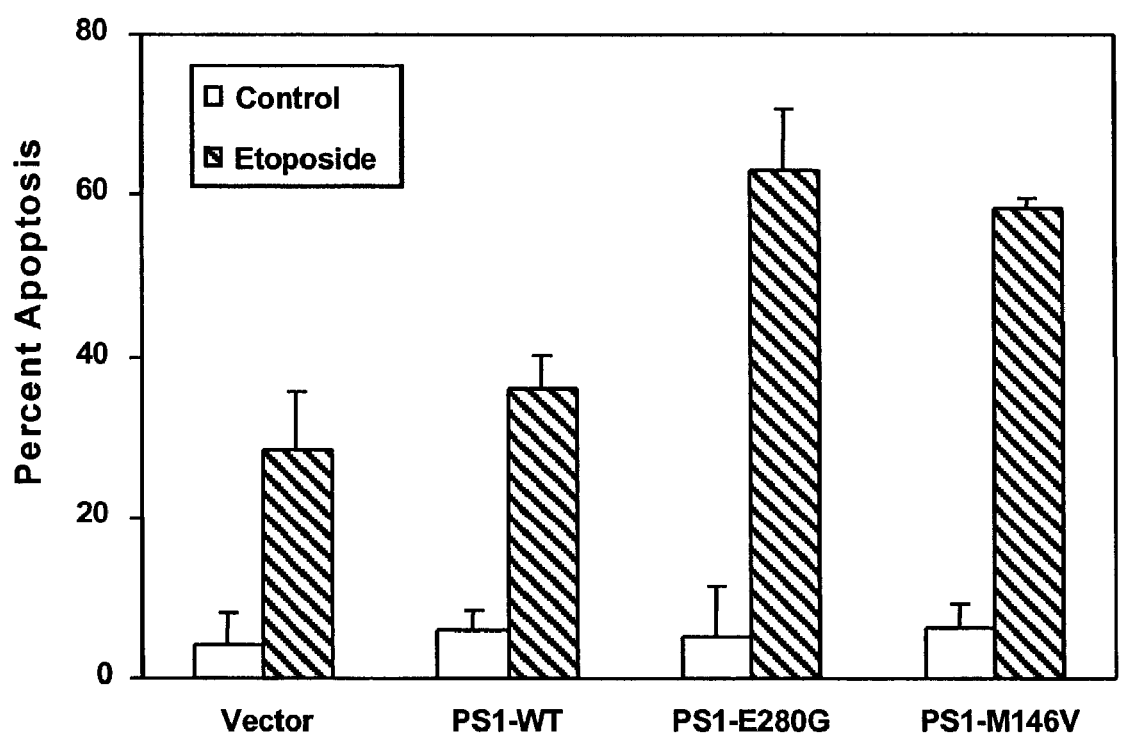
FIG. 1D shows the effect of etoposide treatment on 293HEK cells transiently transfected with PS1-WT or PS1-FAD mutants.

PS1-FAD increased susceptibility to apoptosis was not peculiar to the stably expressing PC12 cells, since a similar phenotype was observed in 293 human embryonic kidney (293HEK) cells transiently expressing PS1-FAD mutants (FIG. 1D). Human 293HEK embryonic kidney cells were transiently transfected by calcium phosphate precipitation. Briefly, $3\times10^5$ 293HEK cells were transfected with 0.01 µg of the β-galactosidase reporter plasmid to indicate transfection plus the test plasmid in six well culture dishes. The PS1-WT and PS1-FAD constructs are described in detail in Example 2. Twenty-four hours post-transfection cells were induced to undergo apoptosis followed by fixation in 0.5% gluteraldehyde and staining with 5-bromo-4-chloro-3-indoyl β-D-galactopyranoside for 2–3 hours. Cells were visualized by phase contrast microscopy. Approximately 300 β-galactosidase-positive cells were assessed from three randomly selected fields from each transfection (n=3), and the mean of these was used to calculate percentage apoptosis. Viable or apoptotic cells were distinguished based on morphological alterations typical of adherent cells undergoing apoptosis including becoming rounded, condensed, membrane blebbing and becoming detached from the culture dish.

It is well documented that upon expression of exogenous PS1, saturable accumulation of exogenous PS1 derivatives is accompanied by a selective compensatory decrease in endogenous PS1 derivatives (Thinakaran et al., *Neuron* 17:181–190 (1996); Thinakaran et al., *J. Biol. Chem.* 272: 28415–28422 (1997); Saura et al., *J. Biol. Chem.* 274: 13818–13823 (1999); and Tomita, et al., *J. Neurosci.* 19:10627–10634 (1999)). In keeping with this model, exogenous expression of PS1-WT does not protect these cells from apoptotic stimuli, presumably due to the saturable accumulation of PS1 derivatives which limits any protective effects of additional PS1 in the 293HEK and PC12 cell systems used. These results suggest an important role for PS1 in maintaining cell viability.

Example 2

In order to investigate a possible role for PS1 in NF-κB activation, an NF-κB dependent luciferase reporter gene plasmid (Stratagene) and increasing concentrations of a wild type PS1 (PS1-WT) expression vector were cotransfected into 293HEK cells. The PS1-WT expression construct plasmid was prepared using pcDNA 3.1 (obtained from Invitrogen) into which the entire coding region for human PS1-WT cDNA was inserted using EcoR1 restriction endonucelase to join the 5' terminus and Kpn1 restriction endonuclease to join the 3' terminus of the PS1-WT sequence. The pcDNA3.1 plasmid utilizes a cytomegalovirus promoter to drive expression of inserted sequences. The NF-κB reporter plasmid was purchased from Stratagene (pNF-uBLuc plasmid #219078–51). 293HEK cells at 80% confluence (~$2\times10^5$ cells per well) in 6 well plates were co-transfected with the plasmids using either Lipofectamine Plus (obtained from Gibco BRL) or the calcium phosphate method of DNA transfection. The PS1-WT plasmid at 0, 0.5, 1.5 and 2.5 µg DNA and 100 ng of NF-κB reporter plasmid DNA were mixed into the transfection vehicle and added to the cells in serum-free medium for 4 hours. After this period, an equal volume of medium containing 10% serum was added and the cultures were incubated overnight before harvesting. To measure luciferase activity, the protocol of Promega was followed. Cell lysates were made with saline washed cells using a 0.2 ml volume of 1× reporter buffer (25 mM Tris-phosphate, 2 mM dithiothreatol, 2 mM 1,2-diaminocyclohexane-N,N,N',N'-tetraacetic acid, 10% glycerol, 1% Trition X-100). Cells were scraped from the well and transferred to a microcentrifuge tube and placed on ice for 10 minutes. The sample was next vortexed and centrifuged at 14,000 rpm for 30 seconds to remove debris. Twenty microliters of the supernatant was mixed with 100 µl of luciferase assay reagent (20 mM Tricine, 1.07 mM $(MgCO_3)_4$ $Mg(OH)_2 5H_2O$, 2.67 mM $MgSO_4$, 0.1 mM EDTA, 33.3 mM dithiolthreatol, 270 µM coenzyme A, 470 µM luciferin, 530 µM ATP) and the reaction was read in a luminometer for 30 seconds.

Figure 2A:
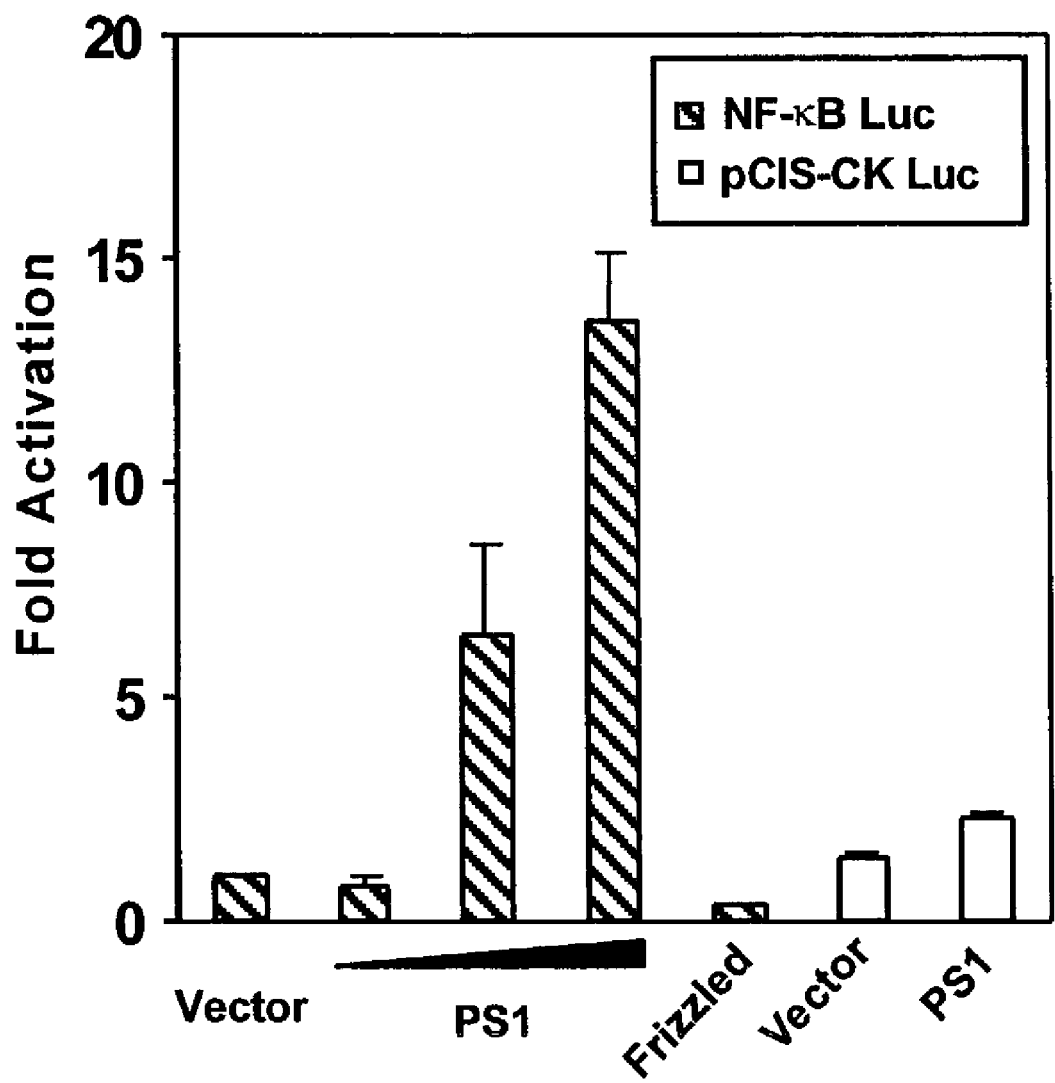
FIG. 2A shows induction of luciferase activity in 293HEK cells as a result of transfection with an NF-κB reporter construct and increasing concentration of PS1. The expression of PS1 activated the reporter in a dose dependent manner. No activation was seen when the reporter construct was replaced with a control construct lacking the NF-κB consensus sequence or with a Frizzled construct encoding another multi-transmembrane domain protein.

As shown in FIG. 2A, the expression of PS1-WT activated the reporter gene in a dose-dependent manner with maximum induction of luciferase activity being 15-fold compared to vector control. No induction of luciferase was observed when a reporter construct lacking the NF-κB consensus sequence (PCIS-CK) was used, indicating that luciferase activity was due to transcriptional activation at the NF-κB binding site (FIG. 2A). As a control for exogenous expression of PS1, 293HEK cells were similarly tested for their response to over-expression of Frizzled, another multi-transmembrane domain protein. In Frizzled transfected cells (1.5 μg) no luciferase activity was detected, indicating that PS1-induced NF-κB activation was not an artifact of over-expressing a large transmembrane protein (FIG. 2A).

Figure 2B:
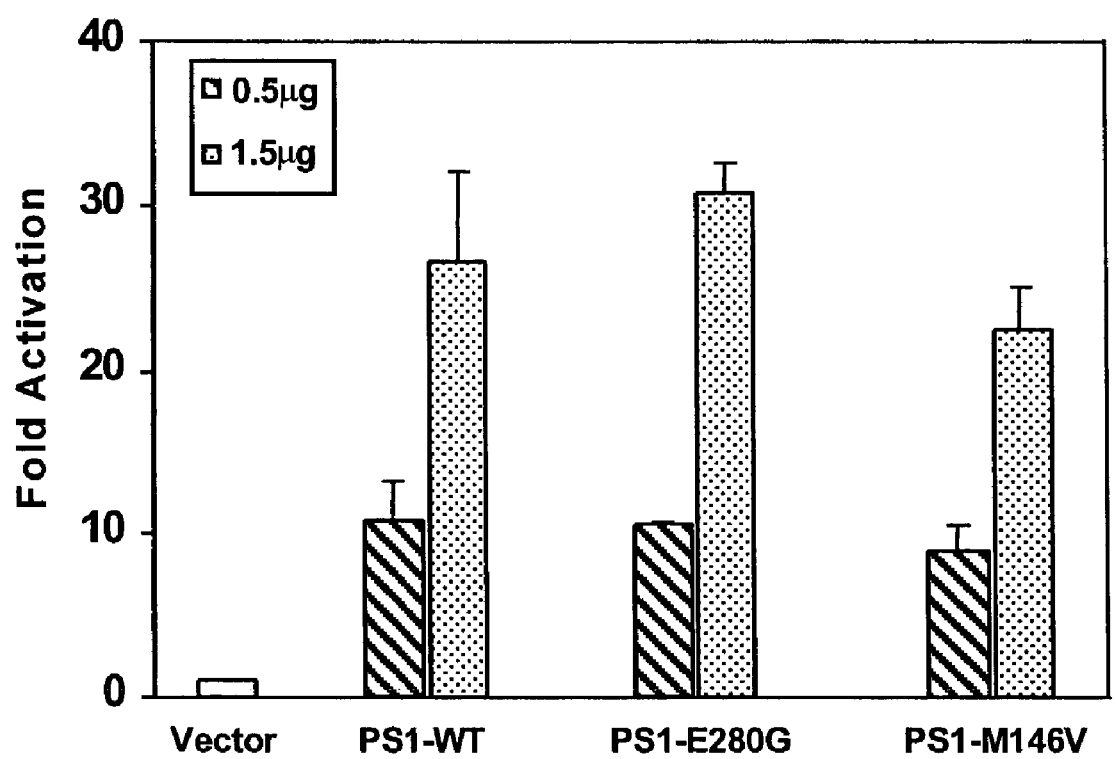
FIG. 2B shows relative luciferase activity as a function of PS1-WT and PS1-FAD concentration in 293HEK cells transfected with the NF-κB dependent luciferase reporter construct. Like PS1-WT, PS1-FAD induced NF-κB activation in a dose dependent manner.

293HEK cell cultures were also transiently transfected with the NF-κB dependent reporter construct as described above (100 ng) and increasing concentrations of PS1-WT and the PS1-FAD mutant (M146V or E280G) expression vectors (0.5 μg, 1.5 μg and 2.5 μg). The PS1-FAD expression plasmid was constructed by subcloning each of the two PS1-FAD coding sequences into pcDNA 3.1 using the same restriction sites as were used for the PS1-WT expression plasmid. PS1-FAD induced NF-κB activation to levels comparable to those of PS1-WT (FIG. 2B), demonstrating that both PS1-WT and PS1-FAD are capable of inducing NF-κB in this assay. As shown in FIG. 2B, the expression of PS1-FAD activated the NF-κB reporter gene in a dose-dependent manner. Importantly, as determined below, NF-κB activity may be compromised in PS1-FAD expressing cells.

Example 3

Several steps in the signaling pathways leading to NF-κB activation are known and many merge at the level of the protein kinase NIK (NF-κB-inducing kinase) (Ninomiya-Tsuji et al., *Nature* 398:252–256 (1999); Ozes et al., *Nature* 401:82–85 (1999); and Pomerantz and Baltimore, *EMBO. J.* 18:6694–6704 (1999)). To define the signaling pathways that couple PS1 to NF-κB activation, the ability of dominant-negative forms of NIK (NIK-DN) and IκB-α (IκB-α-DN; the specific inhibitor of NF-κB) to block PS1-induced NF-κB activation was investigated. The inactive NIK mutant (KK429-430AA) and IκBα mutant (S32A, S36A) are known to behave as dominant-negative inhibitors of both TNFα and IL-1-induced NF-κB activation. Subconfluent cultures of 293HEK cells were transiently transfected with 100 ng of the NF-κB-luciferase reporter gene plasmid, 2.5 μg of PS1-WT and increasing amounts (0.5 μg, 1.5 μg and 2.5 μg) of NIK-DN (gift of Dr. Claudius Vincenz, University of Michigan) or increasing amounts (0.05 μg, 0.1 μg and 0.5 μg) of IκB-α or IκB-α-DN (Clontech). In all experiments cells were harvested 14 to 24 hours post transfection and levels of luciferase activity were determined with the Luciferase Assay System according to manufacturer's directions (Promega). Results are from a representative experiment performed in duplicate with all values expressed relative to that for vector transfected cells, normalized for β-galactosidase expression.

Figure 3A:
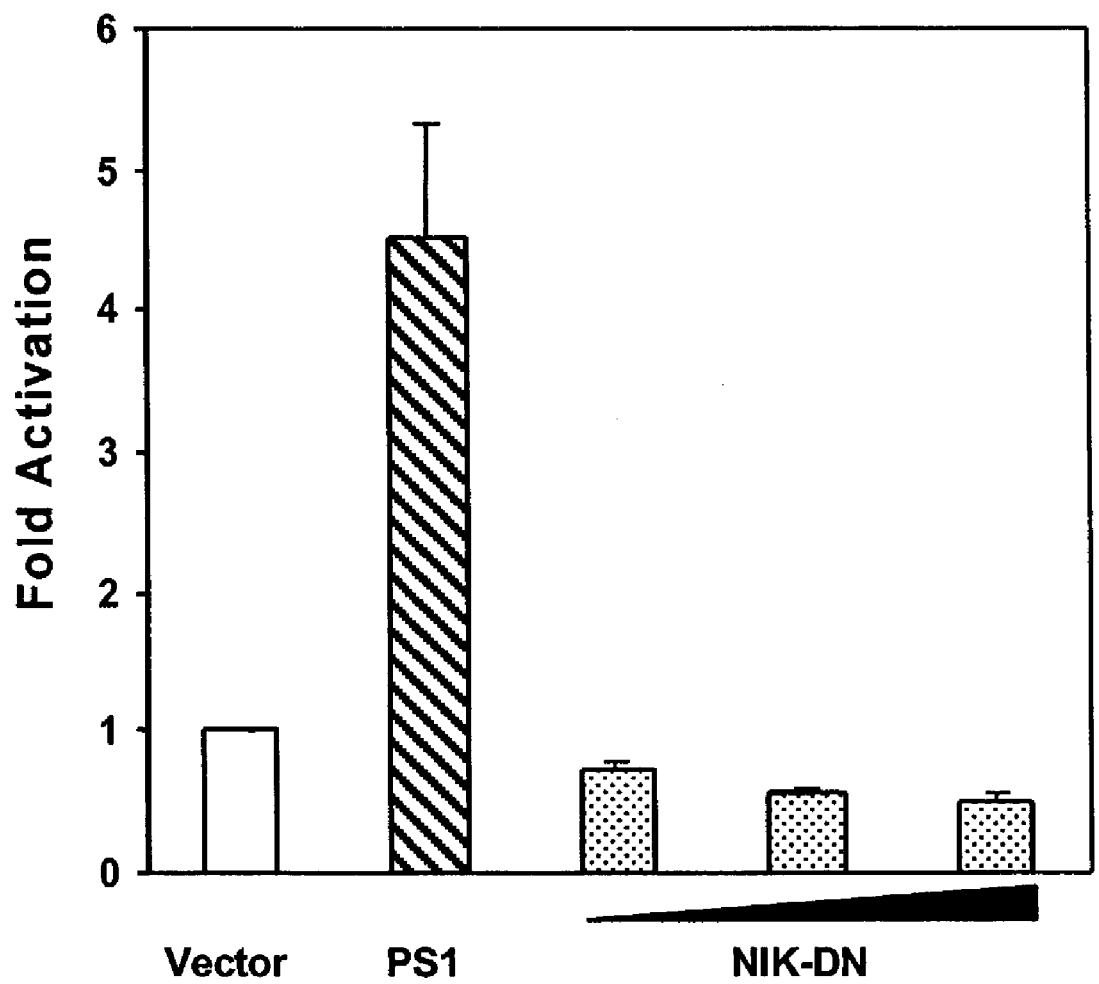
FIG. 3A shows that expression of a dominant negative NIK mutant blocked PS1-mediated activation of NF-κB dependent gene expression.
Figure 3B:
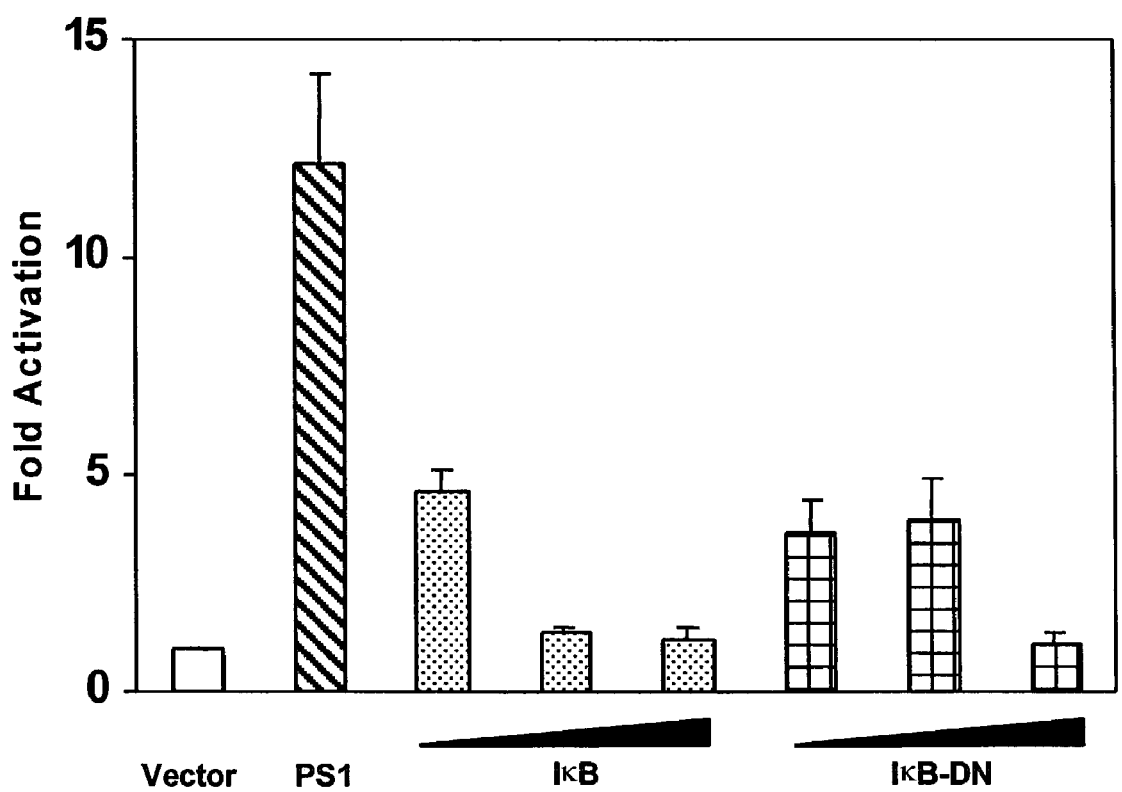
FIG. 3B shows that overexpression of IκB-α or dominant negative IκB-α mutant inhibited PS1-induced NF-κB activation in a dose dependent manner.

Expression of NIK (KK429-430AA) blocked PS1-mediated activation of NF-κB dependent gene expression (FIG. 3A). Furthermore, overexpression of IκB-α or dominant-negative IκB-α (S32A, S36A), inhibited PS1-induced NF-κB activation in a dose dependent manner (FIG. 3B). Taken together, these results indicate that PS1 functions upstream of, or in a parallel pathway to, the NIK-IκBα cascade in mediating NF-κB activation.

Example 4

Figure 4A:
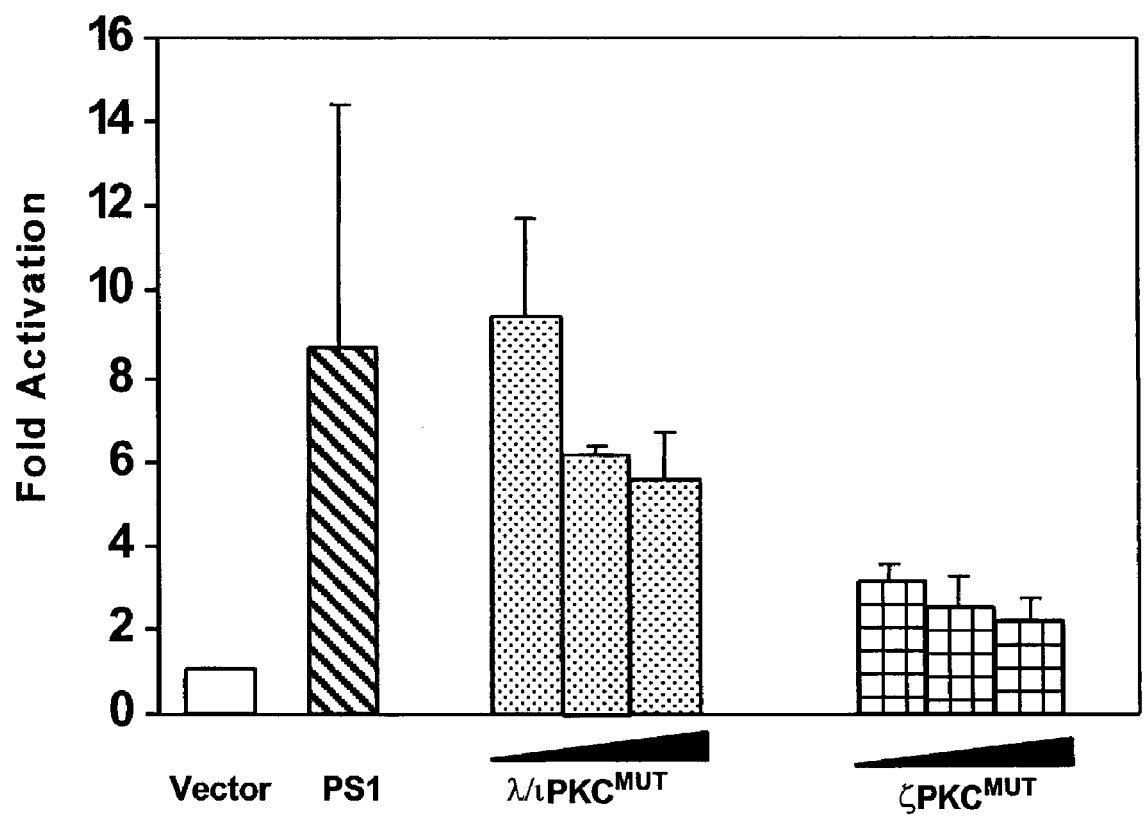
FIG. 4A demonstrates that increasing concentrations of dominant negative forms of the aPKCs, ζPKC-DN and λ/ιPKC-DN, are capable of inhibiting PS-1 induced NF-κB transcription activation. However ζPKC-DN inhibited signaling to a much greater extent and at lower concentrations. These data indicate that PS1 induced NF-κB activation is mediated by ζPKC.

Studies have demonstrated that the atypical PKCs (ζPKC and λ/ιPKC) are stimulated by TNF-α and are required for the activation of NF-κB by TNF-α through a mechanism that involves the phosphorylation of IκB. More recently, it has been demonstrated that both ζPKC and λ/ιPKC directly phopsphorylate IK kinase β (IKKβ) which in turn phosphorylates IκB, resulting in NF-κB activation and transcription regulation (Lallena et al., *Mol. Cell Biol.* 19:2180–2188 (1999)). Over-expression of a ζPKC dominant negative (DN) mutant (kinase inactive) severely impairs the activation of IKKβ in TNF-α stimulated cells. To further characterize PS1-induced NF-κB activation and determine whether the aPKCs are downstream mediators of PS1 induced NF-κB activation, 293HEK cells were cotransfected with PS1-WT (2.5 μg), increasing concentrations of kinase-inactive ζPKC-DN or λ/κ PKC-DN (0.1 μg, 0.25 μg, 0.5 μg; obtained from J. Moscat and described in *Mol. Cell. Biol.* 16:105–114 (1996), and the NF-κB dependent luciferase reporter construct (100 ng). FIG. 4A demonstrates that increasing concentrations of ζPKC-DN dramatically inhibit PS1-mediated NF-κB activation. Interestingly, ζPKC-DN inhibited signaling to a much greater extent than λ/κPKC-DN, which showed significant inhibition only at the higher concentrations (FIG. 4A). These data demonstrate that PS1 induced NF-κB activation is mediated by ζPKC.

Figure 4B:
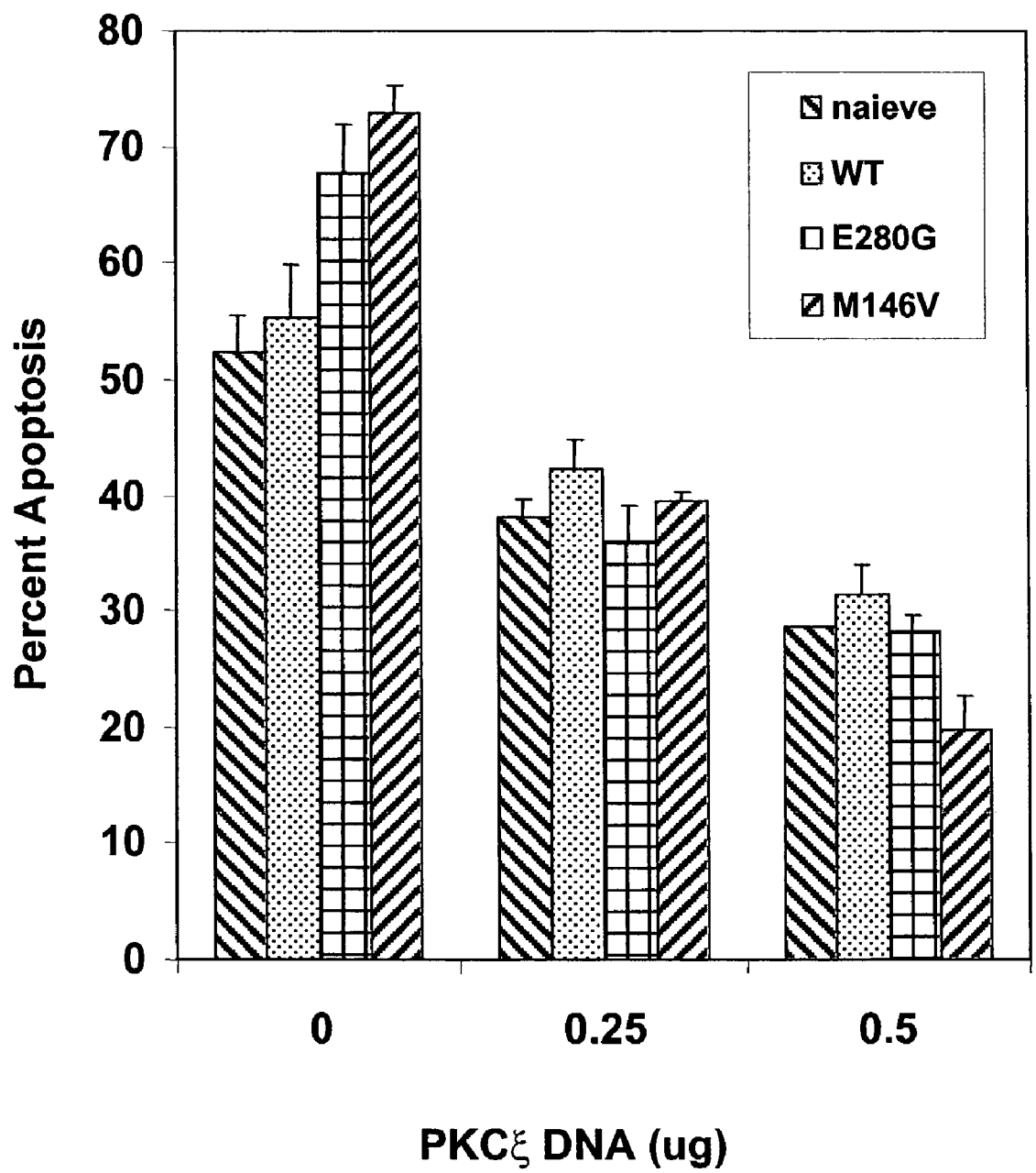
FIG. 4B shows that exogenous ζPKC can rescue 293 cells from apoptotic cell death. The figure also demonstrates that ζPKC can rescue increased vunerability to apoptosis resulting from FAD PS1 expression.

Further evidence that ζPKC is involved in PS1 induced NF-κB activation and subsequent cell survival can be seen in experiments where exogenous ζPKC was found to rescue cells from apoptotic cell death (FIG. 4B). The exogenously expressed ζPKC could rescue cells made more vulnerable to apoptosis by PS1-FAD expression, as well as cells expressing PS1-WT. In these studies, ζPKC was supplied by transient transfection.

Figure 4C:
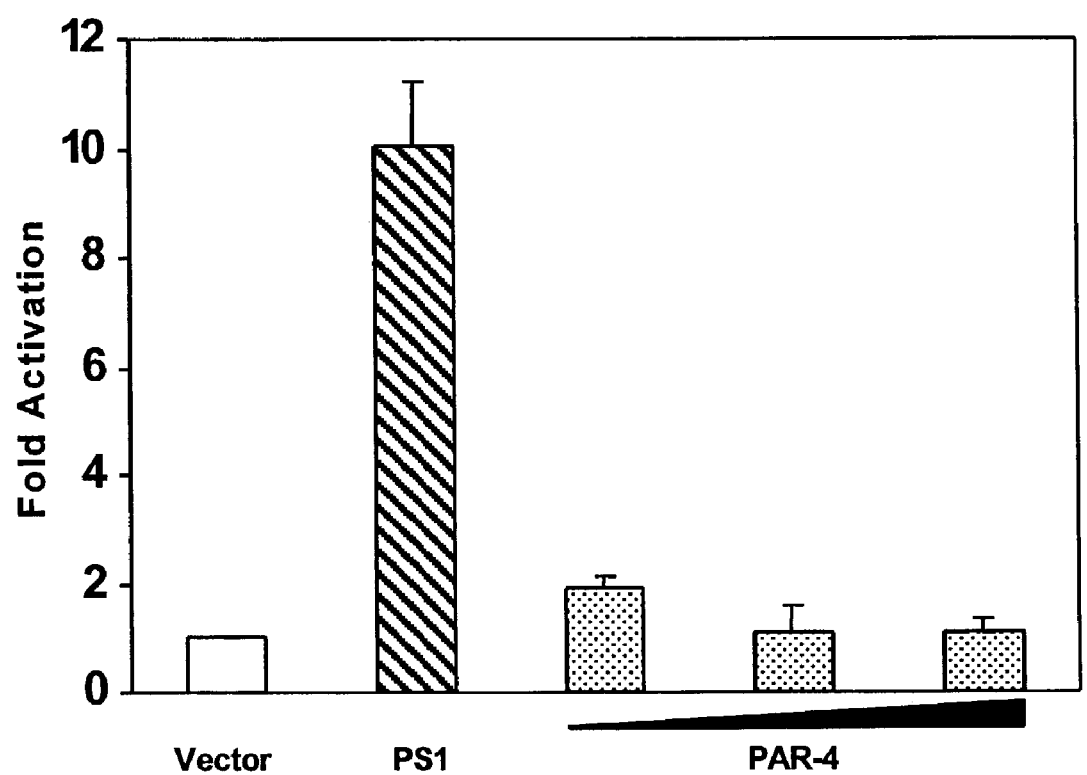
FIG. 4C shows that Par-4 severely abrogates PS1 induced NF-κB activation in 293 human embryonic kidney cells.

To further investigate the involvement of aPKCs in PS1-mediated NF-κB signaling, the ability of the aPKC selective inhibitor, Par-4, to inhibit signaling was tested. Subconfluent cultures of 293HEK cells were transiently transfected with 100 ng of the NF-κB dependent luciferase reporter construct, 2.5 μg of PS1-WT and increasing amounts (0.5 μg, 1 μg and 1.5 μg) of Par-4. Overexpression of Par-4 dramatically inhibited PS1-induced NF-κB activation (FIG. 4C).

Figure 4D:
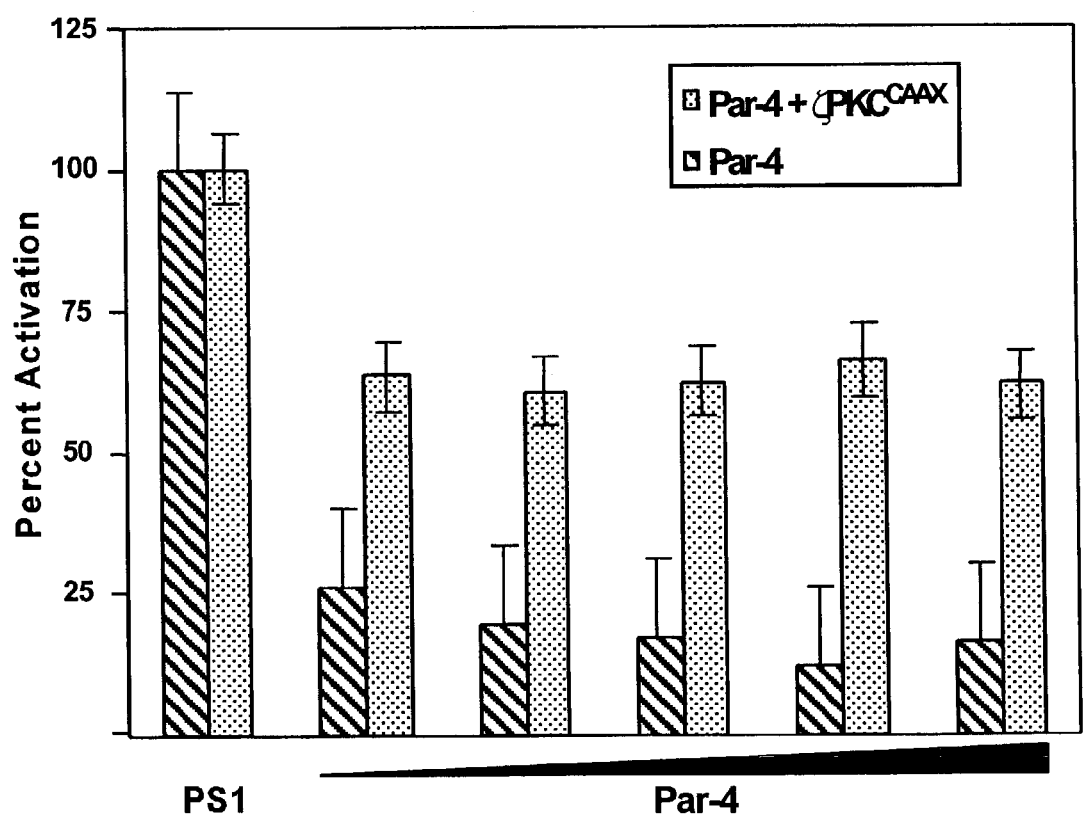
FIG. 4D demonstrates that Par-4 inhibits PS1 induced NF-κB activation through the aPKCs. In the presence of an activated ζPKC mutant, Par-4 showed a significantly reduced ability to inhibit PS1 mediated NF-κB activation.

To demonstrate that Par-4 inhibits PS1-induced NF-κB activation through the aPKCs, an activated ζPKC mutant (ζPKC$^{CAAX}$) (5 μg) was co-transfected with PS1-WT (2.5 μg) and increasing amounts of Par-4 (0.5 μg, 1 μg and 1.5 μg) expression vectors. The data in FIG. 4D clearly indicate that the expression of the ζPKC active mutant inhibits the blockade by Par-4 on PS1-induced NF-κB activation.

Figure 4E:
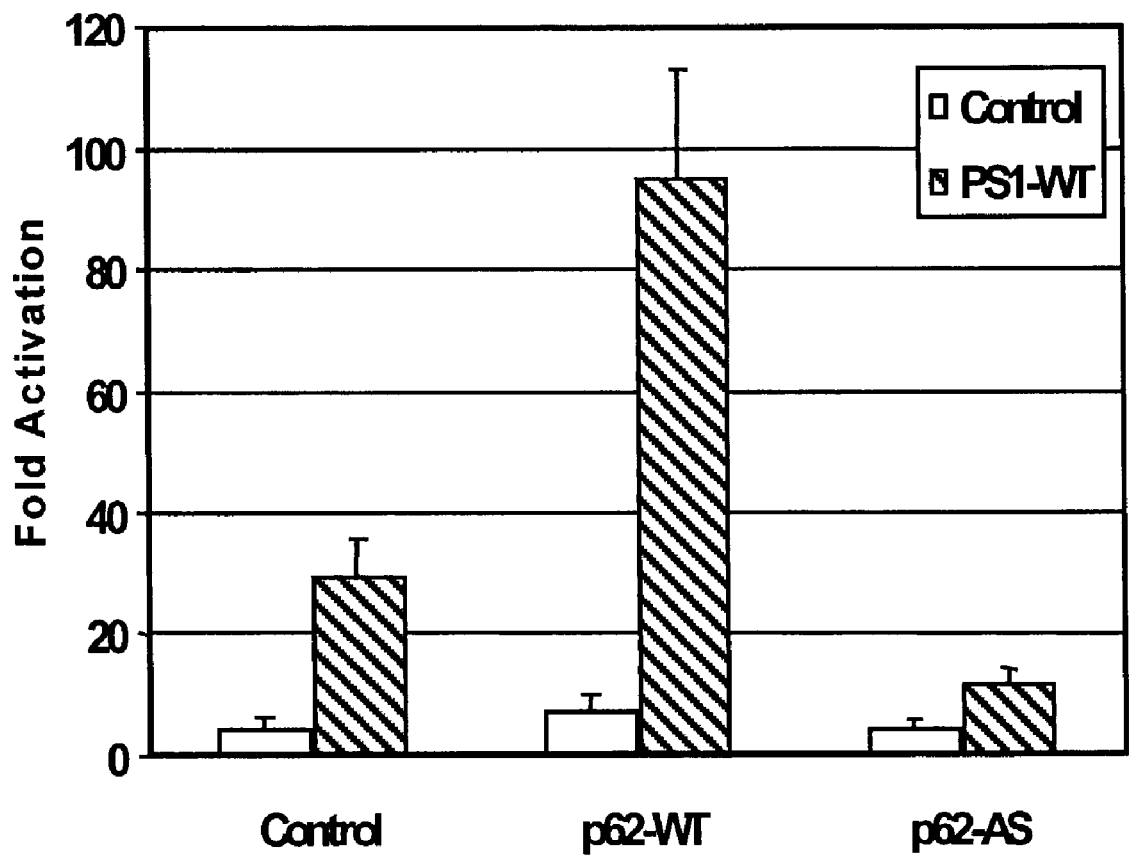
FIG. 4E demonstrates that PS-1 mediated NF-κB activation requires p62 activity. Overexpression of p62 increases the activation of NF-κB by PS1 compared to control levels while expression of an anti-sense p62 construct reduces activation of NF-κB by PS1 to levels below those seen when PS1-WT is transfected alone.

Previous studies have demonstrated that the aPKCs can be activated in response to TNFα and IL-1, and are recruited to the receptor-signaling complex through the specific adapter protein, p62. Therefore, the role of p62 in the activation of NF-κB by PS1 was investigated. Subconfluent cultures of 293HEK cells were transiently transfected with PS1-WT (2.5 μg), 10 ng of the NF-κB reporter gene construct and either 10 μg of a p62 expression construct or 10 μg of a p62 antisense construct (p62$^{AS}$). PS1-induced activation of NF-κB was assessed as above. Significantly, the depletion of endogenous p62 dramatically inhibited the activation of NF-κB by PS1 (FIG. 4E), placing PS1 up-stream of p62 in a NF-κB signaling cascade. Also, increased expression of p62 enhanced the activation of NF-κB by PS1 (FIG. 4E). Collectively, these findings provide strong evidence that PS1-mediated NF-κB activation requires p62 and aPKC activity, which can be inhibited by expression of Par-4, the selective aPKC inhibitor.

Example 5

Understanding the signaling mechanisms utilized by many cell surface receptors to generate cellular responses has lead to the identification of distinct classes of receptor-associated proteins, which couple these receptors to downstream signaling cascades. Following oligomerization of TNFR1 by the trimeric TNF, recruitment of the adapter protein TRADD initiates a NF-κB signaling cascade that absolutely requires the serine-threonine protein kinase REP (Devin et al., *Immunity* 12:419–429 (2000); and Kelliher et al., *Immunity* 8:297–303, (1998)). Recently, it has been shown that the aPKC adapter protein, p62, interacts with RIP and serves to link the aPKCs to the activation of NF-κB by the TNFα signaling pathway (Sanz et al., *EMBO. J.*, 18:3044–3053 (1999)). Consistent with these observations, expression of a p62 antisense plasmid suppresses RIP-induced NF-κB activation (Sanz et al., supra). The results presented in Example 4, demonstrating that a p62 antisense plasmid suppresses PS1-induced NF-κB activation, imply that like RIP, PS1 functions up-stream of p62 in a signaling cascade. Since p62 associates with RIP, the ability of endogenous PS1 to associate with RIP was investigated.

Recruitment of endogenous components of the TNFR-1 signaling complex upon cell stimulation with TNFα has previously been demonstrated (Hsu et al., *Immunity* 4:387–396 (1996); and McCarthy et al., *J. Biol. Chem.* 273:16968–16975 (1998)). To examine the involvement of PS1 in TNFα-induced NF-κB activation, endogenous PS1 was immunoprecipitated at various time points from lysates of TNFα-treated and TNFα-untreated 293HEK cells. The immunoprecipitates were examined by immunoblot with an anti-RIP antibody. Briefly, subconfluent cultures of 293HEK cells were stimulated or not with 40 ng/ml recombinant human TNFα (Calbiochem). Cells were then washed twice with ice cold PBS and lysed in 1 ml of lysis buffer (50 mM HEPES, 150 mM NaCl, 2 mM EDTA, 0.1% Nonidet P-40, 10 mM $Na_3VO_4$, and protease inhibitor mixture (COMPLETE, Boehringer Mannheim). Cells were lysed on ice for 15 minutes then centrifuged at 14,000 rpm for 20 minutes and the supernatants were collected. Lysates were then normalized such that equivalent amount of protein was present in each sample using the bicinchonic acid (BCA) method (Pierce). Lysates were pre-cleared for 2 hours with rabbit pre-immunization serum (5 μg) and 30 μl Protein-G agarose beads (Boehringer Mannheim). The lysates were then immunoprecipitated with 10 μg monoclonal anti-PS1 antibody. The immunoprecipitates were then washed five times in lysis buffer. Samples were resolved on 8% NUPAGE Tris-Glycine gels (Novex), transferred to PVDF membrane (Millipore) and subjected to Western blot analysis with an anti-RIP polyclonal antibody (Sigma).

Figure 5A:
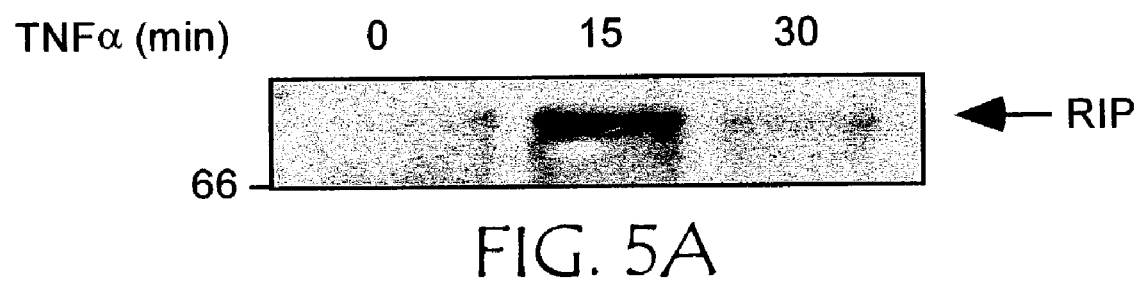
FIG. 5A, upper panel, illustrates that RIP co-immunoprecipitates with PS1 in a TNFα dependent manner, indicating that PS1 is involved in TNFα-induced NF-κB activation. The lower panel shows that the association between PS1 and RIP temporally coincides with activation of NF-κB following stimulation with TNFα as determined by electrophoretic mobility shift assay.

While little association was seen under resting conditions, endogenous RIP reproducibly co-immunoprecipitated with endogenous PS1 in a TNFα dependent manner (FIG. 5A). The association between endogenous PS1 and RIP is rapid and temporally coincides with activation of NF-κB following TNFα stimulation as determined by electrophoretic mobility shift analysis (EMSA) (FIG. 5A lower panel). EMSA was performed as previously described (Wooten et al., *J. Neurosci. Res.* 58:607–611 (1999)). Briefly, treated cells were harvested with cold PBS and washed once in ice-cold PBS. Cell extracts were prepared in high-salt detergent buffer (Totex; 20 mM HEPES, pH 7.9, 350 mM NaCl, 20% Glycerol, 1% NP-40, 1 mM $MgCl_2$, 0.5 mM EGTA, 0.5 mM DTT, 1 mM PMSF and protease inhibitor). Samples were incubated on ice for 30 minutes and were vortexed briefly during incubation, followed by centrifugation at 13,000 g for 5 minutes at 4° C. BCA (Pierce) analysis determined protein concentration of the supernatants, and samples were normalized to equal protein in equal volumes. Activity of NF-κB was determined using 10 μg of protein which was added to a reaction mixture containing 20 μg BSA, 2 μg poly(d(I-C)), 2 μl buffer D (20 mM Hepes, pH 7.9, 20% Glycerol, 100 mM KCl, 0.5 mM EDTA, 0.25% NP-40, 2 mM DTT, 0.1 mM PMSF), 4 μl Buffer F (20% Ficoll 400, 100 mM Hepes, pH 7.9, 300 mM KCl, 10 mM DTT, 0.1% PMSF) and 100,000 c.p.m. of a $^{32}$P-end labeled double stranded oligonucleotide (Promega) containing the κB consensus sequence 5'-AGTTGAGGGGACTTTC-CCAGGC-3' (SEQ ID NO: 9) in a final volume of 20 μl. Samples were incubated at room temperature for 25 minutes. Excess SP-1 (5'-ATTCGATCGGGGCGGGGCGAGC-3' (SEQ ID NO: 10)) or NF-κB oligonucleotides were included as negative controls. Samples were loaded onto a 1 mm 6% tris-glycine gel. The gel was dried and exposed to x-ray film for 24–72 hrs. The specific binding of complexes to the NF-κB oligonucleotide is indicated in FIG. 5A (lower panel).

Figure 5B:
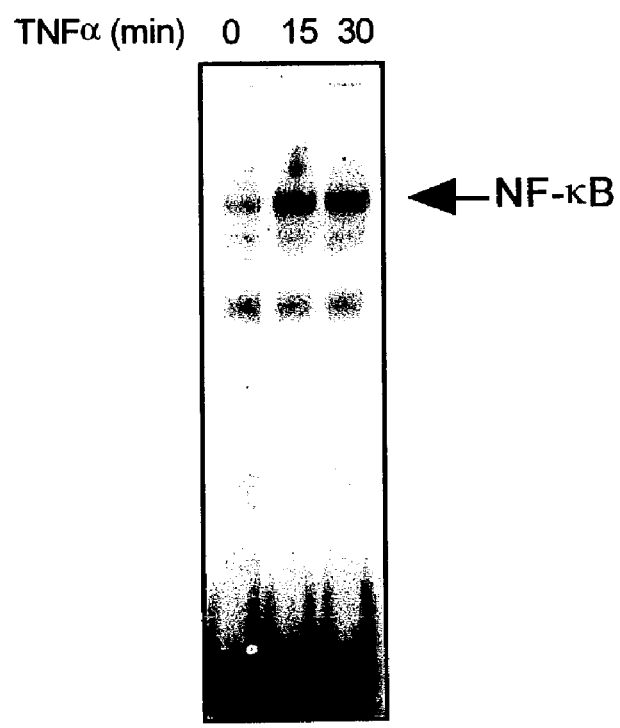
FIG. 5B indicates that PS1-WT has a synergistic effect on TNFα induced NF-κB activation.
Figure 5C:
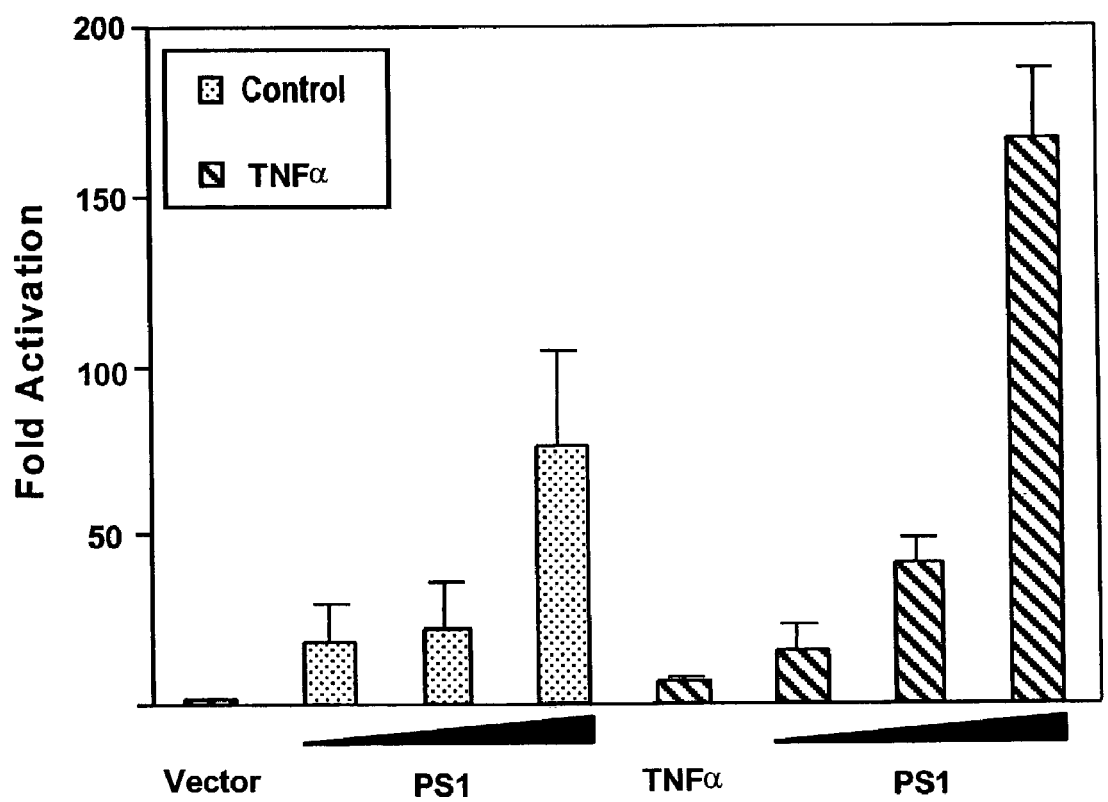
FIG. 5C indicates that like wild type PS1, PS1-FAD mutants synergistically increase TNFα induced NF-κB activation.
Figure 5D:
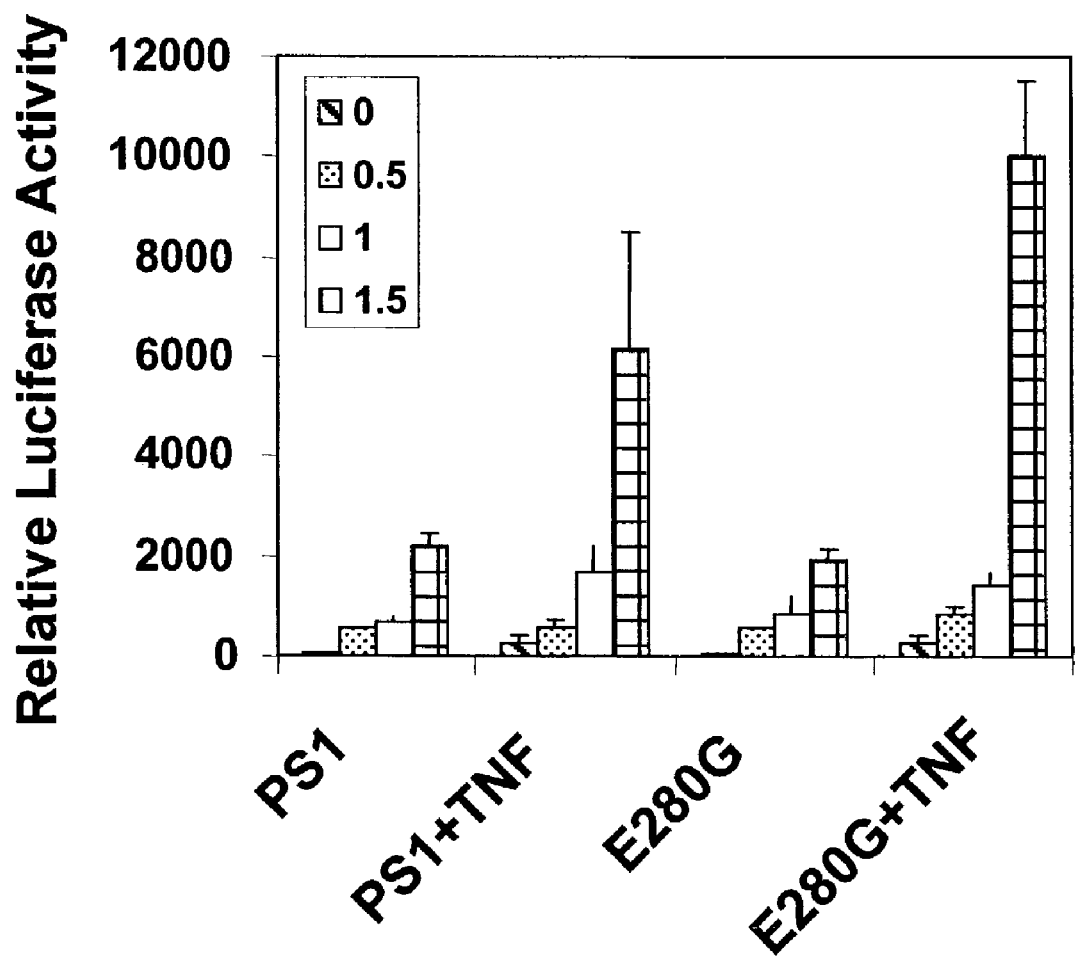
FIG. 5D shows a bar graph indicating relative luciferase activity induced by PS1, PS1+TNFα, E280G, and E280G+TNFα.

TNFα is a well-characterized inducer of NF-κB activation. If PS1 is important in TNFα-induced NF-κB activation, as indicated by inhibition of PS1-induced NF-κB by p62 antisense (FIG. 4E) and the association between endogenous PS1 and RIP (FIG. 5A), increased PS1 expression within the limits of PS1 pool expansion should enhance TNFα-induced signaling pathways that utilize p62 and RIP. To investigate if over-expression of either PS1-WT or PS1-FAD influences TNF-α induced activation of NF-κB, 293HEK cells were transiently transfected with increasing amounts of either the PS1-WT or PS1-FAD expression vector, and the NF-κB dependent luciferase reporter construct. Twenty-four hours post transfection, cells were treated with 40 ng/ml TNF-α for four hours, and then assessed for luciferase activity. Both PS1-WT and PS1-FAD were found to have a synergistic effect on TNF-α induced NF-κB activation as shown in FIGS. 5B and 5C, significantly higher than would be seen if the effect were simply additive.

Although TNF-α is known to induce apoptosis, this cytokine can simultaneously activate NF-κB as a survival signal (reviewed in Ashkenazi and Dixit, *Science* 281: 1305–1308 (1998)). In this context, the synergistic effect seen with PS1 and TNF-α is likely to be a coincident signaling of the NF-κB pathway.

Example 6

The TNFα-dependent interaction between PS1 and RIP in rat primary neuron cultures was investigated. Cortical neuronal cultures were prepared from day 17 embryos of Sprague-Dawley rats, of which non-neuronal cells were less than 10% of the total cortical neuron culture. Standard procedures well known in the art were followed (Li et al, *Neuron* 19:453–463 (1997)). Briefly, cortices were dissected, diced into small pieces, and subjected to treatment with trypsin and Dnase-1. Following dissection, cells were seeded to poly-lysine coated 6 well tissue culture plates (Becton Dickinson) at a density of $1.2 \times 10^6$ cells per well.

Primary cultures were grown in minimal essential medium supplemented with 30 mM glucose, 2 mM glutamine, 1 mM pyruvate and 10% FBS.

Figure 6A:
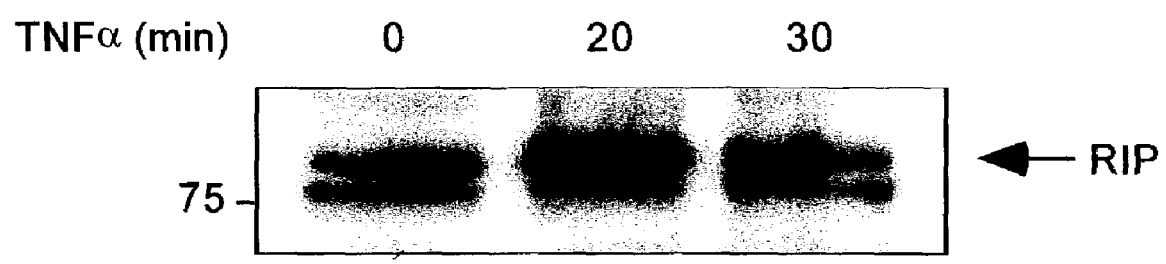
FIG. 6A demonstrates that TNFα treatment enhances the association between PS1 and RIP.

Using antibodies specific for PS1 and RIP, endogenous PS1 was immunoprecipitated at various time points from lysates of TNFα-treated and untreated primary cortical neurons as described above. Subsequent immunoblotting with an antibody specific for RIP (Sigma) revealed TNFα-enhanced association between PS1 and RIP (FIG. 6A). This observation supports the notion that PS1 participates in NF-κB activation through a selective interaction with RIP, an essential TNFR-1 complex component.

The transient association between endogenous PS1 and RIP in primary cortical neurons could be directly correlated with the rapid and transient activation of NF-κB following TNFα stimulation as determined by gel-shift. Electrophoretic mobility shift assays (EMSAs) were carried out as described above using total cell lysates prepared from TNFα-treated cortical neurons and using the light chain κB sequence as the DNA binding probe. Although there was detectable basal level activation, sequence specific NF-κB binding complex was transiently and maximally enhanced within ten minutes of treatment with TNFα and gradually decreased within 30 minutes (FIG. 6B left panel). The validity of the EMSA was demonstrated on addition of 100-fold excess of unlabelled cold NF-κB oligonucleotide which inhibited binding of the upper most pair of band detected in the EMSA (FIG. 6B right panel). These bands were unaffected by inclusion of 100-fold excess of an SP1 oligonucleotide, and omission of cell extract in the binding reaction resulted in an absence of DNA-protein interaction (FIG. 6B right panel). Collectively, these results conclusively demonstrate the concomitant PS1-RIP endogenous association and NF-κB activation in primary cortical neurons.

Example 7

Par-4 expression is enhanced in cells expressing PS1 mutations (PS1-FAD), and specifically inhibits the enzymatic activity of the aPKCs. As demonstrated in FIG. 4C, Par-4 severely abrogated PS1 induced NF-κB activation. The aPKCs are key regulators of NF-κB activity and are negatively regulated by Par-4 (Diaz-Meco et al., *Cell* 86:777–786 (1996)). Together with the evidence presented here that Par-4 impairs PS1-induced NF-κB activation (FIG. 4C), this strongly suggests that increased expression of Par-4, following an apoptotic insult, could be sufficient to inhibit NF-κB survival-signaling, thereby sensitizing PS1-FAD expressing cells to the induction of apoptosis. To address this possibility, Par-4 mRNA levels in the stable PC12 cell lines were determined following exposure to an apoptotic insult. Par-4 mRNA levels were analyzed by quantitative real-time PCR. Briefly, total RNA was analyzed using an ABI Prism™ 7700 Sequence Detection System (PE Applied Biosystems). RNA was extracted and purified from PC12 cell cultures using the RNAqueous kit (Ambion Inc.) according to manufacturer's instructions. Aliquots of RNA (2 μg) were reverse-transcribed using Multiscribe Reverse Transcriptase (PE Applied Biosystems). Sequence-specific primers and probes were designed using Primer Express software (PE Applied Biosystems). The primers and probes for 18S rRNA were: forward 5'-CGGCTACCACATC-CAAGGAA-3' (SEQ ID NO: 11); reverse 5'-GCTGGAAT-TACCGCGGCT-3' (SEQ ID NO: 12); and probe 5'-6FAM-TGCTGGCACCAGACTTGCCCTC-TAMRA-3' (SEQ ID NO: 13). The primers and probes for Par-4 were: forward 5'-CCCAGATCCAGGAACCTCCT-3' (SEQ ID NO: 14); reverse 5'-TTTTGTATCTGCCTGGGACTGTT-3' (SEQ ID NO: 15) and probe 5'-6FAM-CCTGCCCCAGGAC-CCGTCG-TAMRA-3' (SEQ ID NO: 16). For RT-PCR analysis, 1 μl of cDNA was used in a 25 μl reaction mixture in the presence of 200 nM of primers, 100 nM of probe and 0.625 unit of AmpliTaq Gold polymerase. Relative quantitation of Par-4 mRNA and 18S rRNA were calculated using the comparative threshold cycle number for each sample fitted to standard curve. Expression levels for the Par-4 mRNA in each sample were normalized to 18S rRNA.

Figure 7A:
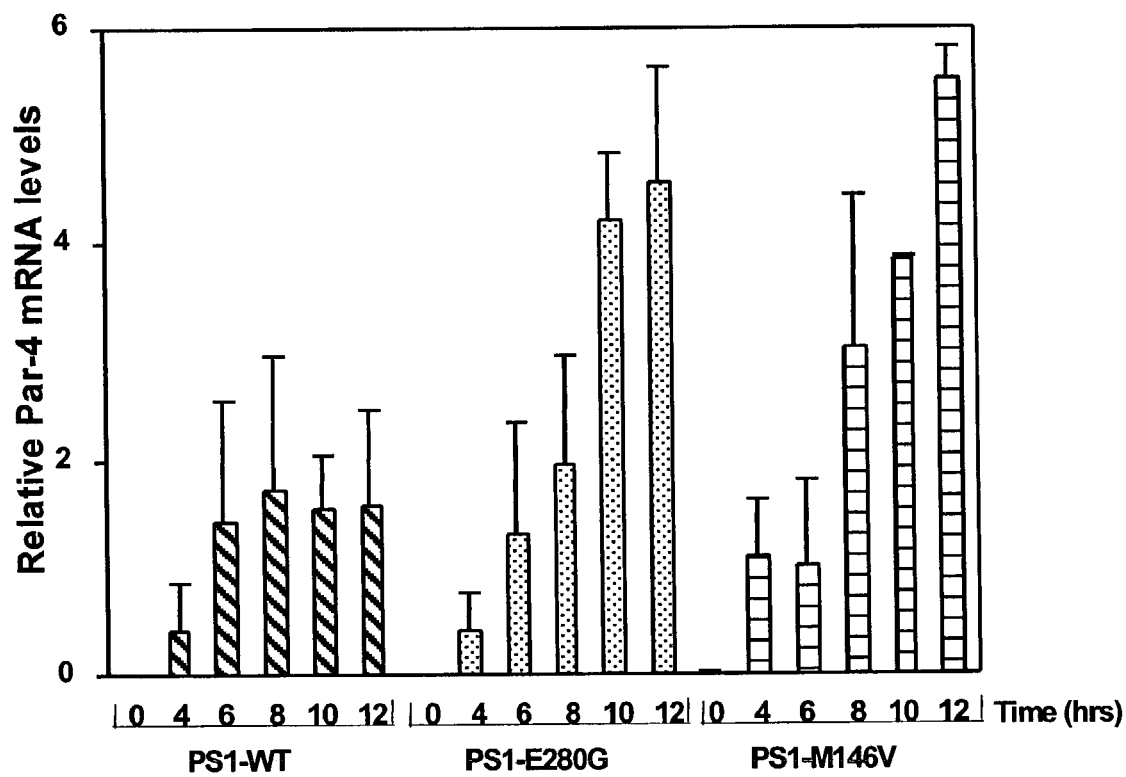
FIG. 7A shows quantitative RT-PCR analysis of Par-4 expression in PC12 cells stably expressing PS1-WT and PS1-FAD mutants following induction of apoptosis. Par-4 mRNA levels increased to a greater extent in the cells expressing PS1-FAD mutants.
Figure 7B:
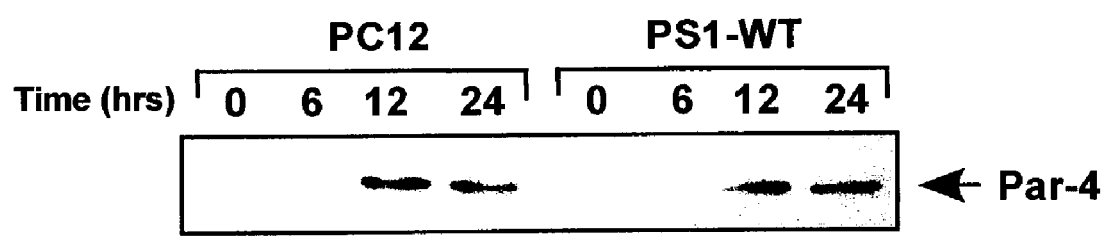
FIG. 7B shows that consistent with the results presented in FIG. 7A, Par-4 protein levels are increased more rapidly and to higher levels in cells expressing PS1-FAD mutant protein when exposed to an apoptotic stimulus.
Figure 7C:
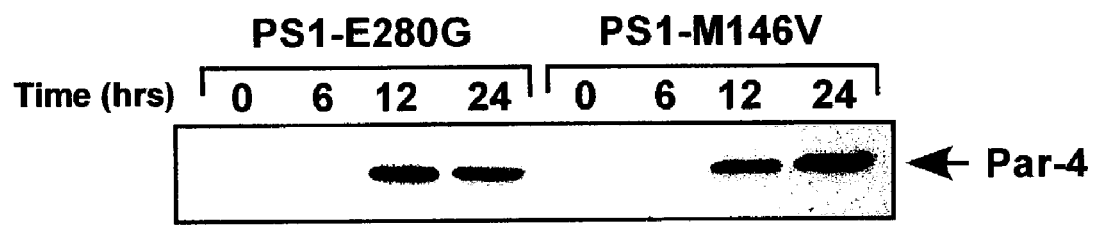
FIG. 7C shows Par-4 protein levels produced over time.

Quantitative RT-PCR analysis showed that Par-4 mRNA levels are increased in PC12 cells stably expressing PS1 following the induction of apoptosis by etoposide (FIG. 7A), while in untreated cells, Par-4 mRNA levels are undetectable. Coincident with the morphological characteristics of apoptosis, Par-4 mRNA levels increased in a time dependent manner following etoposide treatment, starting after 4 hours, and peaking at 6–8 hours in PS1-WT expressing cells. When PC12 cells stably expressing PS1-FAD mutants (M146V or E280G) were exposed to etoposide, Par-4 mRNA levels increased progressively and to greater levels than in cells expressing PS1-WT (FIG. 7A). Consistent with mRNA analysis, when PC12 cells stably expressing either the M146V or E280G PS1 mutation were exposed to etoposide, Par-4 protein levels were increased more rapidly and to higher levels that in naïve or wild-type PS1 expressing cells (FIG. 7B). The increase in Par-4 protein levels coincides with the enhanced susceptibility to apoptosis seen in PS 1-FAD expressing cell lines (FIG. 1B).

Example 8

Regulated activation of NF-κB has been shown to modulate PC12 cell survival, where inhibition of NF-κB blocks survival of PC12 cells and sympathetic neurons (Kaltschmidt et al., *Proc. Natl. Acad. Sci. USA*, 96:9409–9414 (1999); and Taglialatela et al., *J. Neurosci. Res.* 47:155–162 (1997). Further studies have shown that the aPKCs are critical modulators of NF-κB activity and have been shown to enhance PC12 cell survival through a NF-κB dependent pathway (Wooten M. W., et al., *J. Neurosci. Res.* 58:607–611 (1999); and Wooten M. W., et al., *Mol. Cell Biol.* 20:4494–4504 (2000)). Par-4 expression is dramatically induced by pro-apoptotic stimuli where Par-4 mediated apoptosis is dependent on its ability to block aPKC-mediated NF-κB activation (Diaz-Meco et al., *Cell* 86:777–786 (1996)). To test whether increased susceptibility of PS1-FAD cell lines to apoptosis could in part be mediated by reduced NF-κB activity, NF-κB activation following an apoptotic insult in PC12 cell lines stably expressing PS1-WT or PS1-FAD was measured.

Figure 8A:
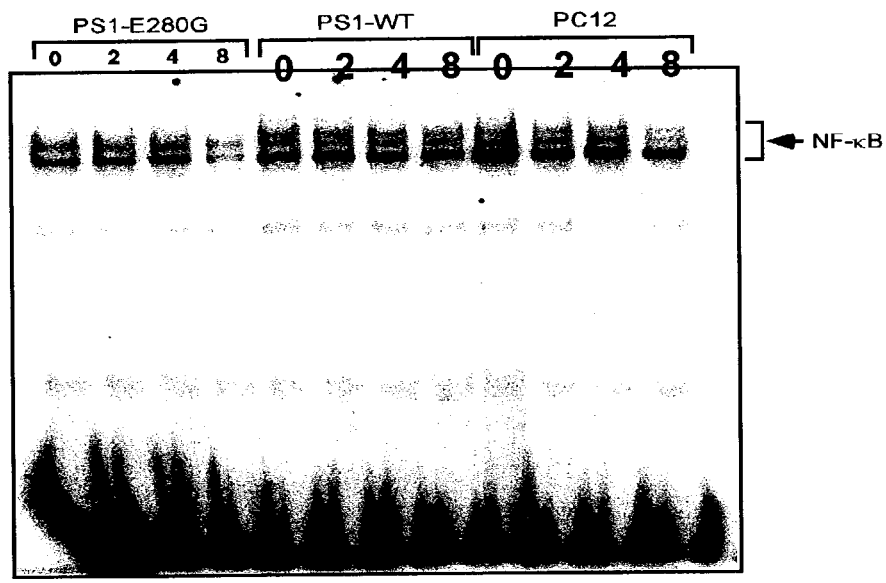
FIGS. 8A and 8B show NF-B activation following an apoptotic insult in PC12 cells stably expressing PS1-WT or PS1-FAD expressing cells showed a significant reduction in specific NF-B binding complex formation following etoposide treatment.
Figure 8B:
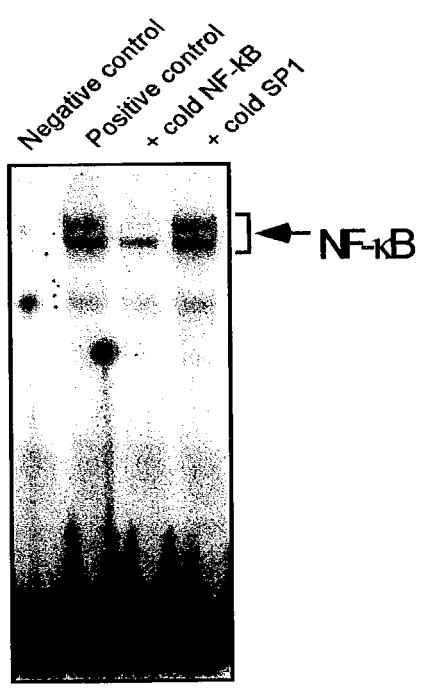

NF-κB activity was measured by EMSA using total cell lysates and the light chain κB sequence as the DNA binding probe as described above. Measurements were conducted with cells under basal conditions and at increasing time points following treatment with etoposide for times known to precede and coincide with the induction of apoptosis (FIG. 8). Analysis was performed using normalized protein concentrations, the same batch of labeled oligonucleotide and exposure to film for the same period of time, to ensure a quantitative measure of differences between the stable cell lines and the parental counterpart. A direct comparison of the DNA binding activity of NF-κB in parental and PS1-WT expressing PC12 cells under non-stimulated basal conditions and etoposide treatment revealed a relatively similar NF-κB complex profile (FIG. 8). In both parental and PS1-WT expressing cells there was a time-dependent reduction in NF-κB active complex following treatment with etoposide. In contrast, the PS1-FAD (E280G) expressing line showed a reproducible reduction in detectable basal level activation and an enhanced reduction in specific NF-κB binding complex formation following etoposide treatment (FIG. 8). In cells expressing PS1-FAD, NF-κB activity was decreased to near undetectable levels at 8 hours post-etoposide treatment (FIG. 8). Significantly, this time-dependent reduction in NF-κB activity, coincided with, and is inversely related to, the enhanced Par-4 expression and occurrence of apoptosis observed in these cultures following etoposide treatment. Competition binding assays with 100-fold excess unlabelled NF-κB or SP1 oligonucleotides confirmed that the migrating complex contained NF-κB (FIG. 8 lower panel). During the course of this experiment etoposide treatment had no effect on SP1 DNA-binding activity, confirming the selectivity for NF-κB activity (Taglialatela et al., *J. Neurosci. Res.* 47:155–162 (1997)).

Example 9

Figure 9A:
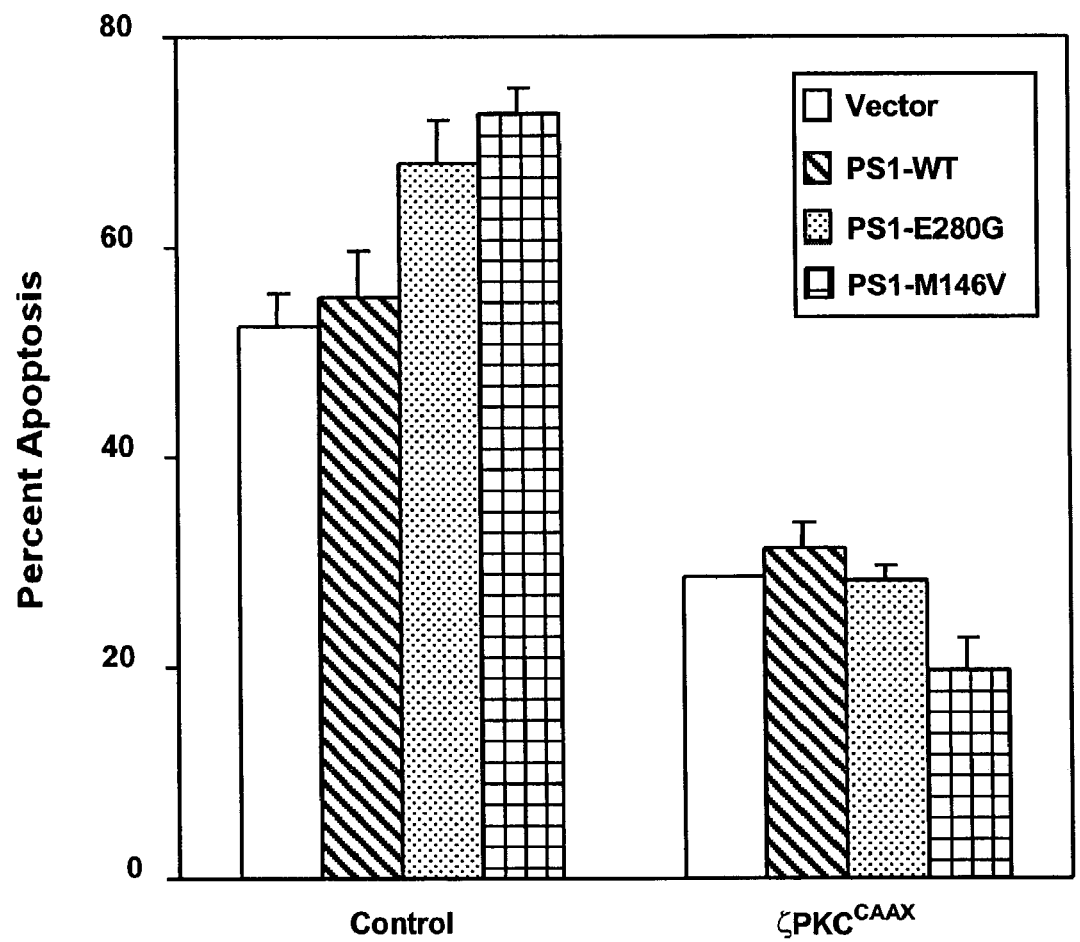
FIG. 9A shows that the expression of a constitutively active ζPKC mutant can prevent the increased susceptibility to apoptosis seen in cells transiently transfected with PS1-FAD mutations.
Figure 9B:
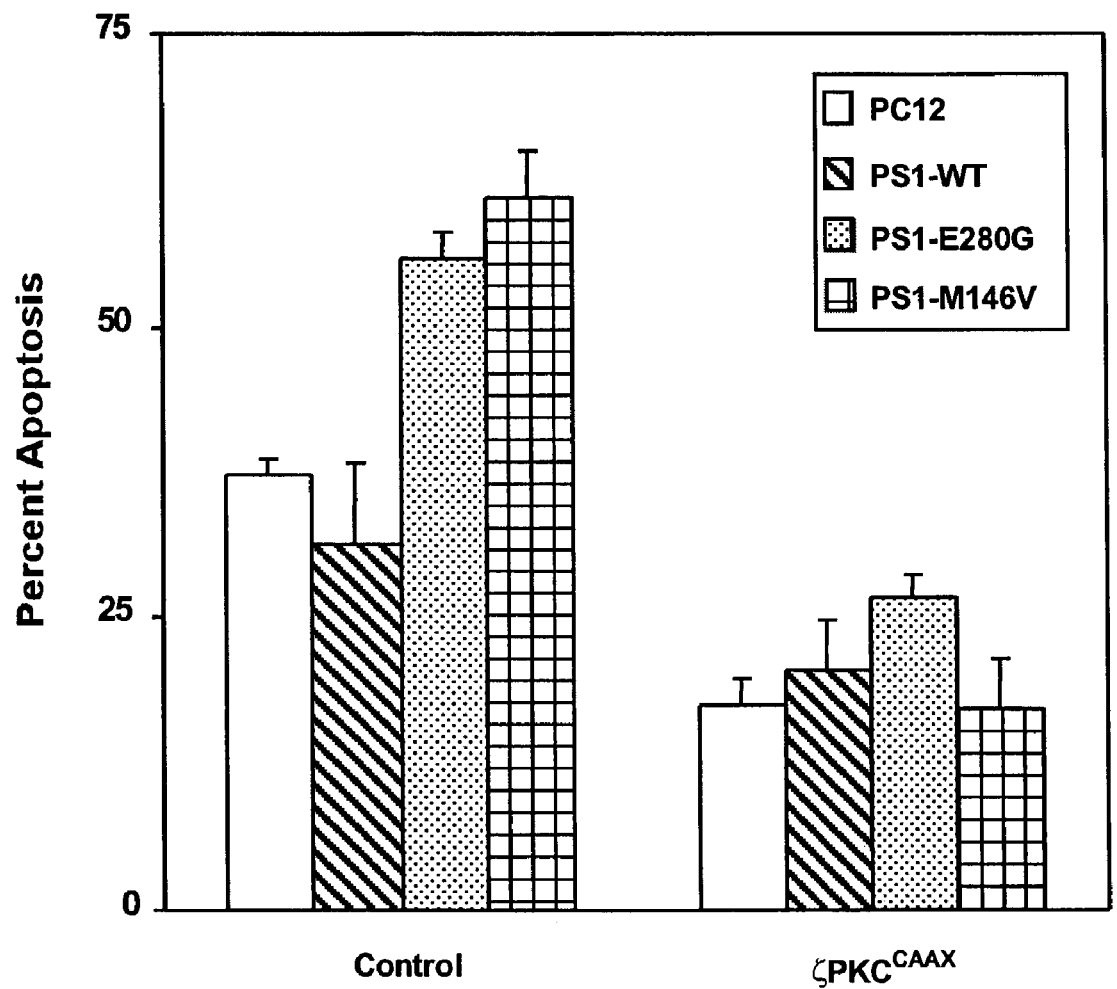
FIG. 9B shows that the expression of a constitutively active ζPKC mutant can prevent the increased susceptibility to apoptosis seen in PC12 cells stably expressing PS1-FAD mutations. This suggests that the increased susceptibility to apoptosis seen in these mutants may require inhibition of aPKC activity.

PS1 and NF-κB activation have been shown to be important mediators of neuronal cell survival. Because Par-4 expression provokes the inhibition of PS1-induced NFκB activation through the aPKC-IκB-α pathway (FIGS. 4A–E), it was determined whether the expression of aPKC was sufficient to prevent the increased susceptibility to apoptosis in cells expressing PS1-FAD mutations. Subconfluent cultures of 293HEK cells were transiently transfected with 1 μg of vector, PS1-WT, PS1-E280G or PS1-M146V either alone or in combination with a constitutively active ξPKC plasmid, ξPKC$^{CAAX}$ together with pGFP as an indicator of transfection. Twenty-four hours post-transfection cells were treated with etoposide (25 μg/ml) and cell viability was determined by morphological evaluation of pGFP positive cells by fluorescent microscopy. Again, cells expressing PS1-FAD mutations demonstrated an increased susceptibility to the induction of apoptosis when compared to PS1-WT expressing cells (FIG. 9A). Interestingly, co-expression of ξPKC$^{CAAX}$ completely inhibited the increased sensitivity to apoptosis associated with the PS1-FAD mutations (FIG. 9A). Similarly, in PC12 cells stably expressing either PS1-WT or PS1-FAD mutants, the expression of ξPKC$^{CAAX}$ dramatically suppressed the increased susceptibility to etoposide in PC12 cells stably expressing PS1-FAD mutants (FIG. 9B). These results indicate that the increased susceptibility to apoptosis associated with PS1-FAD mutations may in part require inhibition of aPKC activity.

Figure 10:
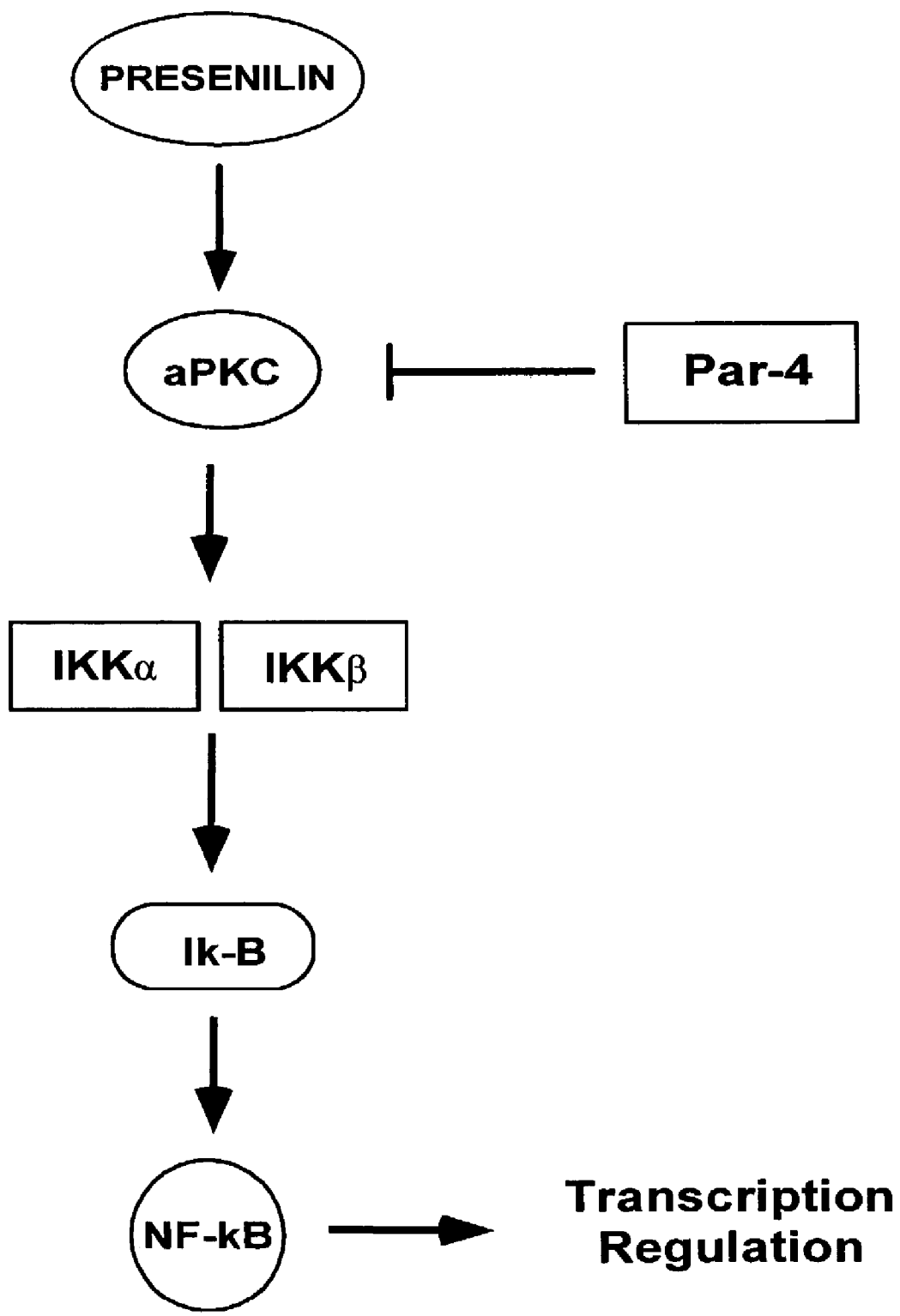
FIG. 10 is a chart illustrating the activation of NF-κB by the atypical protein kinases.

Taken together, the data presented in Examples 1 through 9 strongly suggest that ζPKC and Par-4 are important participants in PS1 mediated NF-κB activation. When paralleled to characteristic events in AD patients, namely, elevated expression of Par-4 and reduced ζPKC activity, mutations in PS-1 may lead to a reduced activation of NF-κB and hence increased susceptibility to apoptosis (see FIG. 10).

All references cited throughout this disclosure, including the examples, and the references cited therein, are hereby expressly incorporated by reference.

What is claimed is:

1. A method for identifying an inhibitor of neuronal degeneration comprising:
   (a) providing eukaryotic host cells expressing a presenilin protein (PS), a prostate apoptosis response-4 (Par-4) polypeptide, and an NF-κB dependent reporter construct;
   (b) exposing the host cells to a candidate molecule;
   (c) monitoring the ability of said candidate molecule to induce NF-κB activation;
   (d) comparing the level of NF-κB activation in the host cells exposed to the candidate molecule to the level of the NF-κB activation in a control sample; and
   (e) identifying the inhibitor of neuronal degeneration when the level of NF-κB activation in the exposed cells is significantly greater than the level of NF-κB activation in the control sample.

2. The method of claim 1, wherein said eukaryotic host cells are mammalian cells endogenously expressing PS.

3. The method of claim 1, wherein said eukaryotic host cells are mammalian cells transfected with nucleic acid encoding PS.

4. The method of claim 3, wherein said PS is PS1.

5. The method of claim 4, wherein said PS1 is human.

6. The method of claim 3, wherein said PS is familial Alzheimer's disease PS (FAD PS).

7. The method of claim 6, wherein said FAD PS is FAD PS1.

8. The method of claim 7, wherein said FAD PS1 is human.

9. The method of claim 1, wherein said eukaryotic host cells are mammalian cells endogenously expressing Par-4.

10. The method of claim 1, wherein said eukaryotic host cells are mammalian cells transfected with nucleic acid encoding Par-4.

11. The method of claim 1, wherein said eukaryotic host cells are neuronal cells.

12. The method of claim 11, wherein said neuronal cells are cerebellar granule cells.

13. The method of claim 11, wherein said neuronal cells are organotypic brain cells obtained from transgenic mice genetically engineered to express human PS1.

14. The method of claim 13, wherein said human PS1 is FAD PS1.

15. The method of claim 1, wherein said NF-κB dependent reporter construct comprises a luciferase reporter gene.

16. The method of claim 15, wherein said NF-κB dependent reporter construct comprises NF-κB-binding consensus sites linked to a luciferase reporter gene.

17. The method of claim 1, wherein the ability of said candidate molecule to induce NF-κB activation is monitored in comparison with a known inducer of NF-κB activation.

18. The method of claim 17, wherein said known inducer of NF-κB activation is TNF-α.

19. The method of claim 1, wherein NF-κB activation is monitored by electrophoretic mobility shift assay.

20. The method of claim 1, further comprising monitoring ξPKC activity in the host cell.

21. The method of claim 20, wherein said ξPKC activity is monitored by an enzymatic assay.

22. The method of claim 1, further comprising monitoring IκB kinase (IKK) phosphorylation.

23. The method of claim 22, wherein the level of IκB kinase (IKK) phosphorylation is measured by immunoprecipitation.

24. The method of claim 1, wherein the host cells are exposed to a plurality of candidate molecules.

* * * * *

SEQUENCE LISTING

```
<160> NUMBER OF SEQ ID NOS: 17

<210> SEQ ID NO 1
<211> LENGTH: 942
<212> TYPE: DNA
<213> ORGANISM: HOMO SAPIEN

<400> SEQUENCE: 1
atgcgcgcca agcagaaccc cccgggcccg gcccccccgg gaggggggcag cagcgacgcc      60 gctgggaagc cccccgcggg ggctctgggc accccggcgg ccgccgctgc caacgagctc     120
aacaacaacc tcccgggcgg cgcgccggcc gcacctgccg tccccggtcc cggggggcgtg     180 aactgcgcgg tcggctccgc catgctgacg cgggcgcccc cggcccgcgg cccgcggcgg     240
tcggaggacg agccccagc cgcctctgcc tcggctgcac cgccgcccca gcgtgacgag      300
gaggagccga acggcgtccc agagaagggc aagagctcgg gccccagtgc caggaaaggc      360 aagggggcaga tcgagaagag gaagctgcgg gagaagcggc gctccaccgg cgtggtcaac      420
atccctgccg cagagtgctt agatgagtac gaagatgatg aagcagggca gaaagagcgg      480
aaacgagaag atgcaattac acaacagaac actattcaga atgaagctgt aaacttacta      540
gatccaggca gttcctatct gctacaggag ccacctagaa cagtttcagg cagatataaa      600
agcacaacca gtgtctctga agaagatgtc tcaagtagat attctcgaac agatagaagt      660
gggttcccta gatataacag ggatgcaaat gtttcaggta ctctggtttc aagtagcaca      720
ctggaaaaga aaattgaaga tcttgaaaag gaagtagtaa cagaaagaca agaaaaccta      780
agacttgtga gactgatgca agataaagag gaaatgattg gaaaactcaa agaagaaatt      840
```

```
gatttattaa atagagacct agatgacata gaagatgaaa atgaacagct aaagcaggaa    900
aataaaactc ttttgaaagt tgtgggtcag ctgaccaggt ag                       942
```

<210> SEQ ID NO 2
<211> LENGTH: 341
<212> TYPE: PRT
<213> ORGANISM: HOMO SAPIEN

<400> SEQUENCE: 2

```
Met Ala Thr Gly Gly Tyr Arg Thr Ser Ser Gly Gly Ser Thr Thr
 1               5                  10                  15

Asp Trp Lys Ala Lys Arg Lys Met Arg Ala Lys Asn Gly Ala Gly
                20                  25                  30

Gly Ser Ser Asp Ala Ala Gly Lys Ala Gly Ala Gly Thr Ala Ala
            35                  40                  45

Ala Ala Asn Asn Asn Asn Gly Ala Ala Ala Val Gly Gly Gly
 50                  55                  60

Val Asn Cys Ala Val Gly Ser Ala Met Thr Arg Ala Ala Arg Gly Arg
 65                  70                  75                  80

Arg Ser Asp Ala Ala Ser Ala Ala Arg Asp Asp Gly Val Lys
                85                  90                  95

Gly Lys Ser Ser Gly Ser Ala Arg Lys Gly Lys Gly Lys Arg Lys Arg
                100                 105                 110

Lys Arg Arg Ser Thr Gly Val Val Asn Ala Ala Cys Asp Tyr Asp Asp
                115                 120                 125

Ala Gly Lys Arg Lys Arg Asp Ala Thr Asn Thr Asn Ala Val Asn Asp
    130                 135                 140

Gly Ser Ser Tyr Arg Thr Val Ser Gly Arg Tyr Lys Ser Thr Thr Ser
145                 150                 155                 160

Val Ser Asp Val Ser Ser Arg Tyr Ser Arg Thr Asp Arg Ser Gly Arg
                165                 170                 175

Tyr Asn Arg Asp Ala Asn Val Ser Gly Thr Val Ser Ser Ser Thr Lys
                180                 185                 190

Lys Asp Lys Val Val Thr Arg Asn Arg Val Arg Met Asp Lys Met Gly
            195                 200                 205

Lys Lys Asp Asn Arg Asp Asp Asp Asn Lys Asn Lys Thr Lys Val
    210                 215                 220

Val Gly Thr Arg Met Ala Thr Gly Gly Tyr Arg Thr Ser Ser Gly Gly
225                 230                 235                 240

Gly Ser Thr Thr Asp Trp Lys Ala Lys Arg Lys Met Arg Ala Lys Asn
                245                 250                 255

Gly Ala Gly Gly Gly Ser Ser Asp Ala Ala Gly Lys Ala Gly Ala Gly
                260                 265                 270

Thr Ala Ala Ala Ala Asn Asn Asn Asn Gly Ala Ala Ala
            275                 280                 285

Val Gly Gly Gly Val Asn Cys Ala Val Gly Ser Ala Met Thr Arg Ala
    290                 295                 300

Ala Arg Gly Arg Arg Asp Ala Ala Ser Ala Ser Ala Ala Arg Asp Asp
305                 310                 315                 320

Gly Val Lys Gly Lys Ser Ser Gly Ser Ala Arg Lys Gly Lys Gly Lys
                325                 330                 335

Arg Lys Arg Lys Arg
            340
```

-continued

<210> SEQ ID NO 3
<211> LENGTH: 1404
<212> TYPE: DNA
<213> ORGANISM: HOMO SAPIEN

<400> SEQUENCE: 3

```
atgacagagt tacctgcacc gttgtcctac ttccagaatg cacagatgtc tgaggacaac      60
cacctgagca atactgtacg tagccagaat gacaatagag aacggcagga gcacaacgac     120
agacggagcc ttggccaccc tgagccatta tctaatggac accccagggt aactcccgg      180
caggtggtgg agcaagatga ggaagaagat gaggagctga cattgaaata tggcgccaag     240
catgtgatca tgctctttgt ccctgtgact ctctgcatgg tggtggtcgt ggctaccatt     300
aagtcagtca gcttttatac ccggaaggat gggcagctaa tctataccc attcacagaa      360
gataccgaga ctgtgggcca gagagccctg cactcaattc tgaatgctgc catcatgatc     420
agtgtcattg ttgtcatgac tatcctcctg gtggttctgt ataaatacag gtgctataag     480
gtcatccatg cctggcttat tatatcatct ctattgttgc tgttcttttt ttcattcatt     540
tacttggggg aagtgtttaa aacctataac gttgctgtgg actacattac tgttgcactc     600
ctgatctgga attttggtgt ggtgggaatg atttccattc actggaaagg tccacttcga     660
ctccagcagg catatctcat tatgattagt gccctcatgg ccctggtgtt tatcaagtac     720
ctccctgaat ggactgcgtg gctcatcttg gctgtgattt cagtatatga tttagtggct     780
gttttgtgtc cgaaaggtcc acttcgtatg ctggttgaaa cagctcagga gagaaatgaa     840
acgcttttc cagctctcat ttactcctca caatggtgt ggttggtgaa tatggcagaa      900
ggagacccgg aagctcaaag gagagtatcc aaaaattcca agtataatgc agaaagcaca     960
gaaagggagt cacaagacac tgttgcagag aatgatgatg cgggttcag tgaggaatgg     1020
gaagcccaga gggacagtca tctagggcct catcgctcta cacctgagtc acgagctgct    1080
gtccaggaac tttccagcag tatcctcgct ggtgaagacc cagaggaaag gggagtaaaa    1140
cttggattgg gagatttcat tttctacagt gttctggttg gtaaagcctc agcaacagcc    1200
agtggagact ggaacacaac catagcctgt ttcgtagcca tattaattgg tttgtgcctt    1260
acattattac tccttgccat tttcaagaaa gcattgccag ctcttccaat ctccatcacc    1320
tttgggcttg ttttctactt tgccacagat tatcttgtac agcctttat ggaccaatta     1380
gcattccatc aattttatat ctag                                          1404
```

<210> SEQ ID NO 4
<211> LENGTH: 467
<212> TYPE: PRT
<213> ORGANISM: HOMO SAPIEN

<400> SEQUENCE: 4

```
Met Thr Glu Leu Pro Ala Pro Leu Ser Tyr Phe Gln Asn Ala Gln Met
  1               5                  10                  15

Ser Glu Asp Asn His Leu Ser Asn Thr Val Arg Ser Gln Asn Asp Asn
             20                  25                  30

Arg Glu Arg Gln Glu His Asn Asp Arg Arg Ser Leu Gly His Pro Glu
         35                  40                  45

Pro Leu Ser Asn Gly Arg Pro Gln Gly Asn Ser Arg Gln Val Val Glu
     50                  55                  60

Gln Asp Glu Glu Glu Asp Glu Glu Leu Thr Leu Lys Tyr Gly Ala Lys
 65                  70                  75                  80
```

-continued

His Val Ile Met Leu Phe Val Pro Val Thr Leu Cys Met Val Val
              85                  90                  95

Val Ala Thr Ile Lys Ser Val Ser Phe Tyr Thr Arg Lys Asp Gly Gln
             100                 105                 110

Leu Ile Tyr Thr Pro Phe Thr Glu Asp Thr Glu Thr Val Gly Gln Arg
             115                 120                 125

Ala Leu His Ser Ile Leu Asn Ala Ala Ile Met Ile Ser Val Ile Val
    130                 135                 140

Val Met Thr Ile Leu Leu Val Leu Tyr Lys Tyr Arg Cys Tyr Lys
145                 150                 155                 160

Val Ile His Ala Trp Leu Ile Ile Ser Ser Leu Leu Leu Phe Phe
                165                 170                 175

Phe Ser Phe Ile Tyr Leu Gly Glu Val Phe Lys Thr Tyr Asn Val Ala
             180                 185                 190

Val Asp Tyr Ile Thr Val Ala Leu Leu Ile Trp Asn Phe Gly Val Val
             195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
             260                 265                 270

Glu Thr Ala Gln Glu Arg Asn Glu Thr Leu Phe Pro Ala Leu Ile Tyr
    275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
             355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
             420                 425                 430

Pro Ala Leu Pro Ile Ser Ile Thr Phe Gly Leu Val Phe Tyr Phe Ala
    435                 440                 445

Thr Asp Tyr Leu Val Gln Pro Phe Met Asp Gln Leu Ala Phe His Gln
    450                 455                 460

Phe Tyr Ile
465

<210> SEQ ID NO 5
<211> LENGTH: 1346
<212> TYPE: DNA

<213> ORGANISM: HOMO SAPIEN

<400> SEQUENCE: 5

```
atgctcacat tcatggcctc tgacagcgag gaagaagtgt gtgatgagcg gacgtccta      60
atgtcggccg agagccccac gccgcgctcc tgccaggagg gcaggcaggg cccagaggat    120
ggagagaaca ctgcccagtg gagaagccag gagaacgagg aggacggtga ggaggaccct    180
gaccgctatg tctgtagtgg ggttcccggg cggccgccag gcctggagga agagctgacc    240
ctcaaatacg gagcgaagca cgtgatcatg ctgtttgtgc ctgtcactct gtgcatgatc    300
gtggtggtag ccaccatcaa gtctgtgcgc ttctacacag agaagaatgg acagctcatc    360
tacacgacat tcactgagga cacaccctcg gtgggccagc gcctcctcaa ctccgtgctg    420
aacaccctca tcatgatcag cgtcatcgtg ttatgaccca tcttcttggt ggtgctctac    480
aagtaccgct gctacaagtt catccatggc tggttgatca tgtcttcact gatgctgctg    540
ttcctcttca cctatatcta ccttggggaa gtgctcaaga cctacaatgt ggccatggac    600
tacccccacc tcttgctgac tgtctggaac ttcggggcag tgggcatggt gtgcatccac    660
tggaagggcc ctctggtgct gcagcaggcc tacctcatca tgatcagtgc gctcatggcc    720
ctagtgttca tcaagtacct cccagagtgg tccgcgtggg tcatcctggg cgccatctct    780
gtgtatgatc tcgtggctgt gctgtgtccc aaagggcctc tgagaatgct ggtagaaact    840
gcccaggaga gaaatgagcc catattccct gccctgatat actcatctgc catggtgtgg    900
acggttggca tggcgaagct ggaccctcc tctcagggtg ccctccagct ccctacgac    960
ccggagatgg aagaagactc ctatgacagt tttggggagc cttcataccc cgaagtcttt   1020
gagcctccct tgactggcta cccaggggag ggctggagga agaggaggaa agggcgtga   1080
agcttggcct cggggacttc atcttctaca gtgtgctggt gggcaaggcg ctgccacgg   1140
gcagcgggga ctggaatacc acgctggcct gcttcgtggc catcctcatt ggcttgtgtc   1200
tgaccctcct gctgcttgct gtgttcaaga aggcgctgcc cgccctcccc atctccatca   1260
cgttcgggct catcttttac ttctccacgg acaacctggt gcggccgttc atggacaccc   1320
tggcctccca tcagctctac atctga                                         1346
```

<210> SEQ ID NO 6
<211> LENGTH: 448
<212> TYPE: PRT
<213> ORGANISM: HOMO SAPIEN

<400> SEQUENCE: 6

```
Met Leu Thr Phe Met Ala Ser Asp Ser Glu Glu Val Cys Asp Glu
 1               5                  10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
               100                 105                 110
```

-continued

| | | | | | | | | | | | |
|---|---|---|---|---|---|---|---|---|---|---|---|
|Thr|Glu|Lys|Asn|Gly|Gln|Leu|Ile|Tyr|Thr|Thr|Phe|Thr|Glu|Asp|Thr|
| |115| | | |120| | | |125| | |

Pro Ser Val Gly Gln Arg Leu Leu Asn Ser Val Leu Asn Thr Leu Ile
    130             135             140

Met Ile Ser Val Ile Val Val Met Thr Ile Phe Leu Val Val Leu Tyr
145             150             155             160

Lys Tyr Arg Cys Tyr Lys Phe Ile His Gly Trp Leu Ile Met Ser Ser
                165             170             175

Leu Met Leu Leu Phe Leu Phe Thr Tyr Ile Tyr Leu Gly Glu Val Leu
            180             185             190

Lys Thr Tyr Asn Val Ala Met Asp Tyr Pro Thr Leu Leu Leu Thr Val
        195             200             205

Trp Asn Phe Gly Ala Val Gly Met Val Cys Ile His Trp Lys Gly Pro
    210             215             220

Leu Val Leu Gln Gln Ala Tyr Leu Ile Met Ile Ser Ala Leu Met Ala
225             230             235             240

Leu Val Phe Ile Lys Tyr Leu Pro Glu Trp Ser Ala Trp Val Ile Leu
                245             250             255

Gly Ala Ile Ser Val Tyr Asp Leu Val Ala Val Leu Cys Pro Lys Gly
            260             265             270

Pro Leu Arg Met Leu Val Glu Thr Ala Gln Glu Arg Asn Glu Pro Ile
        275             280             285

Phe Pro Ala Leu Ile Tyr Ser Ser Ala Met Val Trp Thr Val Gly Met
290             295             300

Ala Lys Leu Asp Pro Ser Ser Gln Gly Ala Leu Gln Leu Pro Tyr Asp
305             310             315             320

Pro Glu Met Glu Glu Asp Ser Tyr Asp Ser Phe Gly Glu Pro Ser Tyr
                325             330             335

Pro Glu Val Phe Glu Pro Pro Leu Thr Gly Tyr Pro Gly Glu Glu Leu
            340             345             350

Glu Glu Glu Glu Glu Arg Gly Val Lys Leu Gly Leu Gly Asp Phe Ile
        355             360             365

Phe Tyr Ser Val Leu Val Gly Lys Ala Ala Ala Thr Gly Ser Gly Asp
370             375             380

Trp Asn Thr Thr Leu Ala Cys Phe Val Ala Ile Leu Ile Gly Leu Cys
385             390             395             400

Leu Thr Leu Leu Leu Leu Ala Val Phe Lys Lys Ala Leu Pro Ala Leu
                405             410             415

Pro Ile Ser Ile Thr Phe Gly Leu Ile Phe Tyr Phe Ser Thr Asp Asn
            420             425             430

Leu Val Arg Pro Phe Met Asp Thr Leu Ala Ser His Gln Leu Tyr Ile
        435             440             445

<210> SEQ ID NO 7
<211> LENGTH: 371
<212> TYPE: DNA
<213> ORGANISM: HOMO SAPIEN

<400> SEQUENCE: 7
gaattcggca cgaggggcgc cgctcggctc ccttcccgcc cctggctccc tccctccctc       60
cctccctcct tcttctccct ccctcctgtc ctgggattgc ctggagctcc gcaccgcgag      120
tttgccgcgg cactttccgc gcggcggaag agcgcgcgcc agcttcggca cacctgggag      180
ccggatccca gccctacgcc tcgtccccta caagctcctc caagcccgc cggctgctgt       240

-continued

| gggagcggcg gccgtccctc tcctggaggt cgtctcctgg catcctcggg gccgcaggaa | 300 |
| ggaagaggag gcagcggccg gagccctggt gggcggcctg aggtgagagc ccgaccggcc | 360 |
| cctttgggaa t | 371 |

<210> SEQ ID NO 8
<211> LENGTH: 5870
<212> TYPE: DNA
<213> ORGANISM: HOMO SAPIEN
<220> FEATURE:
<221> NAME/KEY: CDS
<222> LOCATION: (5832)...(5935)
<220> FEATURE:
<221> NAME/KEY: intron
<222> LOCATION: (5214)...(5690)

<400> SEQUENCE: 8

| gaattccaga aggcaggaac agagaaagta gaaggaaagt cttataaaag aaagagaata | 60 |
| ggccaggcac ggtggctcac gcctctaatc ccagcatttt gggaggctga ggcaggtgga | 120 |
| tcatgaggtc aggagttcaa gaccaacctg accaacatgg tgaagccccg tctctactaa | 180 |
| aaatacaaaa attaaccagg cgtgtgtgcc tgtaatccca gctactcagg aggctgaggc | 240 |
| aggagaatcg cttgaacccg aaaggtgaag gttgctgtga gcctagatca ggccactgca | 300 |
| ctctgacctg ggcgacagag cgagactcca tgtcaaagaa aaagaaagag gataagaaaa | 360 |
| tttcctaact ggaaggcaga tagctgatta aaagggtcca ctgactgcat aacataataa | 420 |
| tgataaaaga ccaaatcaga gcatatcttc aagatatttc agaggatcta agtaagaaga | 480 |
| tccaaaaatt ttgagacaga aaatacaatg caatcagaat gccactggtc ttctaaacag | 540 |
| caactctgga aactagatga taataaagca atgccttcaa aattatgaag gaaaatgctt | 600 |
| tctaacctag agttctatgc tccaccaaac tattaatcaa gtatgaagat aaatttaaaa | 660 |
| cattttccaa tatgcaaggt ctctaagaat gagtttatact atcttcagaa tatactgagg | 720 |
| atatactctg ctaaaatgaa ggggagaaac aaaaagagaa agtatgcaa ttcaggaaac | 780 |
| agaagtcta cagagaaaat gattctcaag gtgttagagg agcataatcc caggatgacc | 840 |
| acaagcaacg agccttaaaa tcagtccaga ttaggccagg tgcggtggct cacacctgta | 900 |
| atcccagcac tttgggaggc caaagcaggc tggttgcctg agctcagaag ttcgagacca | 960 |
| gtctgggcaa catggtgaaa cccccgtctc tactaaaata caaaaaatta gctgggcgtg | 1020 |
| gtggcatgtg cctgtattcc cagctactct ggaggctgat gcaggagaat tgcttgaacc | 1080 |
| caggaggcgg aggttgcagt gagccaagac tgcgccactg cactcagcc tcaccaacag | 1140 |
| agcgagactc cgtctccaaa caaacaaaca aaatcaatcc atattaaagc agggatgga | 1200 |
| gggctccaga acagatgttt ccaaaaagag aatagaacta atagcttacc caatgtgatt | 1260 |
| aacgtcattg agaggaggaa aatttgagta tatacttgtg actggtatat aaaaaaataa | 1320 |
| gccgatgatt aaagaaaaaa aagaggcaa gttttaactg cagaaaaatg gtaaagacaa | 1380 |
| aaggtatagt tgtgcaacaa ggaaaaacag ttgtaaaaaa aagaaatgc aatcatatac | 1440 |
| accacatgac tcagctatga acagtatttg tatagtcata atactacggg cgtgtaggag | 1500 |
| tatgaaaagt atatgtgtgg ccgggcatgg tggctcatgc ctgtaatccc agaactttgg | 1560 |
| gaggccgagg cgggtggatc acgaggtcag gagatcgaga tcatcctggc taacacagtg | 1620 |
| aaaccccgtc tctactaaaa atgcaaaaaa aaaaaaaaa aaaaaaaaa attagccggg | 1680 |
| cgtggtggca gccacctgta gtcccagcta ctcaggaggc tgaggcagga gaatggcgtg | 1740 |
| aacccgggag gcggagcttg cagtgagccg agatcgcgcc actgcactcc agcctgggag | 1800 |

```
acagagcgag actccatctc aaaaaaaaag aaaaaaaaa gaaaagaaa agaaaagtat    1860
atgtgttatt agtgtattag agctaaatcc tcttctatat ctaaaaatgg aaaaatcaag    1920
atgtacaata gcagatatgc acataaaaaa taaatatgaa gatctctatt aatggaacca    1980
gttaaaaagt tcaaagtttt gggtagggtt ttcagaatgg ataaggtaga gagggattg    2040
ctgttttttg ttataatcct tgtagaacta agtatgtaa ttttttatc ctatgcacat    2100
ataatatttt gatgttagag gatgaattgc atatgttcca gaaatacctg cattgaaggc    2160
aaaatggcta cttcccaata cactagctat ccatacatat aataatacac ttcctcaaaa    2220
tcattaagac taacatctag gtttcactct gacatattta aatgaatctg tttttgtcag    2280
cattatcatc atatttcatt ttattattaa gggcaagtga gtcgctaaaa attggttatt    2340
ttaggctaac tcagaggtgc tcaaccgggg aagaatttta tcccagggac catgtggcaa    2400
tgtcacaata caggtggggg tttcttattg gtatctaata ggtagaagcc aacgatgctg    2460
ctaaacaacc tacaatgggc aggacagcaa agaattatcc agccccaaat gtaacagtgc    2520
tgaggttgag aaaccaagct ccaagtcttt gaggattatt tcatcagaac gctatacata    2580
aagattgatg atatgcaaac atcttgcaat ttaggactga ctcagctaaa tacctcggtg    2640
caatgttgga agcagtctgg ctgtgaaata tatcttcggg aatattgaga atggtaaaga    2700
caaaaggtat aataaatgat aataataaca aaacacagag ctttgtacct caataatctc    2760
tttcatccat ggttcctagg gcactttata gactaataat acctactctg gtactcacat    2820
accaccttt atctaaggac tgcaggcact ttcacaacac tctcacgatg caggaagtat    2880
tattatcccc attttatatg taagtaaaca gaggcacaaa agttaagcaa cttgcccaaa    2940
gccacacaag tcagtagcag ccaaaattcc tgactcagaa cctattaaca ctaagagaac    3000
tggtctaagc catgcagtga taaatttatg tggggtgtta tcctagttca ttcaaagtct    3060
atcgttttta ggctgatatt gtatattcaa taccccatct gttataattt cctcttctcc    3120
catacacttc ttagagacca aggactttaa gcccctagaa gggactatgt ttactgagtg    3180
ccttcctcga atcaagcaca ttttatgtgc agtgtcagtt cttaagacag cttaaatata    3240
atgtaattgg gaggctgaga gcaggagaat tgcttgaact caggaggcgg aggttgcagt    3300
gagctgagat cccgccactg cactccagcc tggcgacaga gcgagactcc gcctcaaaaa    3360
aaaaaaaaat gtaattttg ctgattttat agtacagaaa gctgagtacc agataatgta    3420
aacatgccca agatctctca gctagctgac tattccctct ttccactata tcctgcagcc    3480
cttccaggag aaaagtcctc tgataagtta caaagcatat gaatgtgaat acgtttaatg    3540
tcccagcctc ccttactctc cttaaaactc agaaaacaaa ctaatgaata tgtaattgag    3600
aaacttcagg tggcacactg gggttggtac tagcttaggt aaacagccgc tcagcctttt    3660
agacctattc ccaacaaaag cttttaattt tctaaggatt ttttccagagc tctcgccata    3720
cgtttcccac aacagccaga ccaaagacca aaactgtctt tccctgagaa atatagagca    3780
tgtgaatcac tttcttctgt tcccagttct gtggcaggca acactgatt gctcactcat    3840
catgtgctac ctgggcaaaa caggaatatt aagtaggaag aaaggtttat gttaggtaag    3900
agcgtgactt agggctctcc tactttttta caaaatggag acctggcatt tgtagcctcc    3960
cacaatgatg tgccctgaca ttacttggat atagaaaggt cagtcttagg tgcgtcagtg    4020
acagcccacc ccgctctgat ccagaaattt cagatgactt gcatcagagg ataagcctct    4080
ggcatgttaa taatgaaaaa atagagacaa tcactgcccc agctcatctc aaattagcat    4140
```

-continued

```
cagtgcagcg ttagtacttt ggtagggagc tttgctgcta aattcattct ctgtaaagag    4200
gagaggcaga gacagggtta aggggaaaac tccaagactg aatcgccaa tacaataaac     4260
tgtcgaactg agttttttct cccgcaaccc taagatacta gtaagtcctt cctcttagcc    4320
aaccctttc accagggcac cgcagttttc ttagaaggag ggtgctgggt ttgtctcagg     4380
tctttctatt ctcctgcccg ctgcctagt acatctgaaa agggagcagc gactaggaaa    4440
agagacacgt gggtattttc ccatcctgtc tagtcattcc ctgaatcatc acaagttatc    4500
gcacttttcc ccttagccag cagcgttcga gactttctct caaataatac ggtcttgtac    4560
ttaaaaggaa gagtggtggg agaagagaga ggcggagaag acaagcaaga agggcgtgga    4620
gtgccgttcc cgccccggag tcggaggcgc cgggaggccg gacgccgcga agctgctagc    4680
ccaggaatgt gccgtctaac tcgcaggcc cgggcggagc gcggcgggcg cgctgtggtc    4740
tgcggcggga gcggggcaga ggacggctgg cgcagggcag gctgcagcgg cgggccggac    4800
gcgacgccgc gcacctgagc gccggggcg ggcgtcagc ggccacgacc cttcccaccg     4860
cgcgccgcgc ccctcgcgcg ccgcctcggc cttttccgct cgtgcttcgg cgccgctcgg    4920
ctcccttccc gccctggct ccctcccctcc ctccctccct ccttcttctc cctccctcct    4980
gtcctgggat tgcctggagc tccgcaccgc gagtttgccg cggcacttc cgcgcggcgg     5040
aagagcgcgc gccagcttcg gcacacctgg gagccggatc ccagccctac gcctcgtccc    5100
ctacaagctc ctccaaggta aggcgctcgc tcacacccgg tcctttccac gctcggcggg    5160
acagctgggt ccccgcctcc tctgcgaacc ggctaggagc tccgcgcctc gccttgggag    5220
tggggttgta gctgacgggg acctcggacc ggcggtggct agagcgcgga gcaggcgata    5280
cgacgagccg acaggtggcg ggtctagccc tagtatctcg accgccgccg cgcgggacct    5340
tggtggggat ggggcgggcg ggccgacttg ggggtggggt cagtcctctc tcctcccttc    5400
tagggcggc gatcgtcggg gtccgtactg taggtgcgtg ggagaaactt tgcagggtgg    5460
ggacccggcg gctgctggcc ggtagtgact ggtgggcgcg ctcgaggact ccaagggcg     5520
cagcccgggg gcagacccctt gggtcgggcg gggatcttac gcttccctta cccgccccct    5580
tttgtctttc acctcagccc cgccggctgc tgtgggagcg gcggccgtcc ctctcctgga    5640
ggtcgtctcc tggcatcctc ggggccgcag gaaggaagag gaggcagcgg ccggagccct    5700
ggtgggcggc ctgaggtgag agcccgaccg gcccctttgg gaatatggcg accggtggct    5760
accggaccag cagcggcctc ggcggcagca ccacagactt cctggaggag tggaaggcga    5820
aacgcgagaa gatgcgcgcc aagcagaacc ccccgggccc ggccccccg               5870
           Met Arg Ala Lys Gln Asn Pro Pro Gly Pro Ala Pro Pro
            1               5                  10
```

<210> SEQ ID NO 9
<211> LENGTH: 34
<212> TYPE: PRT
<213> ORGANISM: HOMO SAPIEN

<400> SEQUENCE: 9

Met Arg Ala Lys Gln Asn Pro Pro Gly Pro Ala Pro Pro Gly Gly Gly
 1               5                  10                  15

Ser Ser Asp Ala Ala Gly Lys Pro Pro Ala Gly Ala Leu Gly Thr Pro
            20                  25                  30

Ala Ala

<210> SEQ ID NO 10
<211> LENGTH: 22

```
<212> TYPE: DNA
<213> ORGANISM: Artificial Sequence
<220> FEATURE:
<223> OTHER INFORMATION: Synthetic Oligonucleotide

<400> SEQUENCE: 10
agttgagggg actttcccag gc                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
attcgatcgg ggcggggcga gc                                              22

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
cggctaccac atccaaggaa                                                 20

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
gctggaatta ccgcggct                                                   18

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
tgctggcacc agacttgccc tc                                              22

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
cccagatcca ggaacctcct                                                 20

<210> SEQ ID NO 16
<211> LENGTH: 23
<212> TYPE: DNA
<213> ORGANISM: Artificial Sequence
<220> FEATURE:
<223> OTHER INFORMATION: Synthetic Oligonucleotide
```

```
<400> SEQUENCE: 16
ttttgtatct gcctgggact gtt                                             23

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 17
cctgccccag gacccgtcg                                                  19
```